(12) United States Patent
Marto et al.

(10) Patent No.: US 9,678,083 B2
(45) Date of Patent: Jun. 13, 2017

(54) PROTECTED AMINE LABELS AND USE IN DETECTING ANALYTES

(75) Inventors: Jarrod A. Marto, Wayland, MA (US); Scott B. Ficarro, Melrose, MA (US); Manor Askenazi, Arlington, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 13/501,940

(22) PCT Filed: Oct. 14, 2010

(86) PCT No.: PCT/US2010/052731
§ 371 (c)(1),
(2), (4) Date: Jun. 25, 2012

(87) PCT Pub. No.: WO2011/047192
PCT Pub. Date: Apr. 21, 2011

(65) Prior Publication Data
US 2012/0258886 A1    Oct. 11, 2012

Related U.S. Application Data

(60) Provisional application No. 61/278,953, filed on Oct. 14, 2009.

(51) Int. Cl.
| | |
|---|---|
| *C07D 295/24* | (2006.01) |
| *C40B 40/04* | (2006.01) |
| *G01N 27/62* | (2006.01) |
| *G01N 33/68* | (2006.01) |
| *C07D 207/40* | (2006.01) |
| *C07D 207/404* | (2006.01) |
| *C07D 249/18* | (2006.01) |
| *C07D 253/08* | (2006.01) |
| *C07D 471/04* | (2006.01) |

(52) U.S. Cl.
CPC ....... *G01N 33/6848* (2013.01); *C07D 207/40* (2013.01); *C07D 207/404* (2013.01); *C07D 249/18* (2013.01); *C07D 253/08* (2013.01); *C07D 471/04* (2013.01); *G01N 2458/15* (2013.01); *G01N 2560/00* (2013.01); *Y10T 436/145555* (2015.01)

(58) Field of Classification Search
CPC ............................... C07F 295/24; C40B 40/04
USPC ......................................................... 506/15
See application file for complete search history.

(56) References Cited

U.S. PATENT DOCUMENTS

| | | | |
|---|---|---|---|
| 2004/0068094 A1* | 4/2004 | Borromeo et al. | 530/317 |
| 2005/0164182 A1* | 7/2005 | Pickering | C07H 19/06 435/6.11 |
| 2007/0048752 A1* | 3/2007 | Yan et al. | 435/6 |

FOREIGN PATENT DOCUMENTS

| | | | |
|---|---|---|---|
| JP | 2005121380 A | | 5/2005 |
| WO | 2005068446 A1 | | 7/2005 |
| WO | WO 2005068446 A1 | * | 7/2005 |
| WO | WO-2007/012849 | | 2/2007 |
| WO | WO 2007012849 A2 | * | 2/2007 |
| WO | WO-2008/110581 | | 9/2008 |
| WO | WO 2008110581 A2 | * | 9/2008 |
| WO | WO 2009060071 A1 | * | 5/2009 |
| WO | WO-2009/141310 | | 11/2009 |
| WO | WO 2010008159 A2 | * | 1/2010 |

OTHER PUBLICATIONS

Cherevin et al., N-Trifluoroacetyl-beta-alanine in the Synthesis of Carnosine, Russian J. Chem., 2007, 77(9), 1576-1579.*
Dayon et al., Relative Quantification of Proteins in Human Cerebrospinal Fluids by MS/MS Using 6-Plex Isobaric Tags, Anal. Chem., 2008, 80, 2921-2931.*
Seo et al., MAss-Balanced 1H/2H Isotope Dipeptide Tag for Simultaneous Protein Quantification and Identification, Anal. Chem., 2008, 80, 6145-6153.*
Dolusic et al., Biotinylated Indoles as Probes for Indole-Binding Proteins, Bioconjugate Chem., 2001, 12, 152-162.*
Turecek, Mass Spectromety in Coupling with Affinity Capture-Release and Isotope-Coded Affinity Tags for Quantitative Protein Analysis, J. Mass Spectrometry, 2002, 37, 1-14.*
Dass, C; Chapter 6, Organic and Inorganic Mass Spectrometry, Fundamentals of Contemporary Mass Spectrometry, 2007, 195-261.*
Dass, C.; Forematter, Fundamentals of Contemporary Mass Spectrometry, 2007, 1-3.*
Seebach et al., Isotopically Labelled and Unlabelled beta-Peptides with Geminal Dimethyl Substitution in 2-Position of Each Residue: Synthesis and NMR Investigation in Solution and in the Solid State, Helvetica Chimica Acta, 2002, 85, 2877-2917.*
Levina et al., Oligonucleotide Derivatives Bearing Reactive and Stabilizing Groups Attached to C5 of Deoxyuridine, Bioconjugate Chem., 1993, 4, 319-325.*
Yates et al., Proteomics By Mass Spectrometry: Approaches, Advances, and Applications, Annu. Rev. Biomed. Eng., 2009, 11, 49-79.*
Bantscheff et al., Quantitative Mass Spectrometry in Proteomics: A Critical Review, Anal. Bioanal. Chem., 2007, 389, 1017-1031.*
Ficarro et al., Improved Electrospray Ionization Efficiency Compensates for Diminished Chromatographic Resolution and Enables Proteomics Analysis of Tyrosine Signaling in Embryonic Stem Cells, Anal. Chem. 2009, 81, 3440-3447.*
Viner et al., "Quantification of post-translationally modified peptides of bovine alpha-crystallin using tandem mass tags and electron transfer dissociation", Journal of Proteomics, vol. 72, No. 5, pp. 874-885 (2009).

(Continued)

*Primary Examiner* — Amy M Bunker
(74) *Attorney, Agent, or Firm* — Mintz Levin Cohn Ferris Glovsky and Popeo, P.C.

(57) ABSTRACT

The invention is directed towards novel amino acid based compounds, which may be isotopically enriched, and methods of use of such compounds for characterizing one or more molecules of a sample by mass spectrometry, the method comprising: (a) reacting the one or more molecules with the compound; and (b) characterizing the one or more molecules by mass spectrometry.

4 Claims, 49 Drawing Sheets

(56) References Cited

OTHER PUBLICATIONS

Supplemental European Search Report mailed Jul. 29, 2013 in corresponding European Patent Application No. 10824121.7.
Mass-Balanced 1H/2H Isotope Dipeptide Tag for Simultaneous Protein Quantitation and Identification, Anal. Chem., vol. 80, No. 16, pp. 6145-6153 (2008).
Ross et al., "Mulitplexed Protein Quantitation in *Saccharomyces cerevisiae* Using Amine-reactive Isobaric Tagging Reagents", Molecular & Cellular Proteomics, vol. 3, No. 12, pp. 1154-1169 (2004).
Dayon et al., "Relative Quantification of Proteins in Human Cerebrospinal Fluids by MS/MS Using 6-Plex Isobaric Tags", Anal. Chem., vol. 80, No. 8, pp. 2921-2931 (2008).

\* cited by examiner

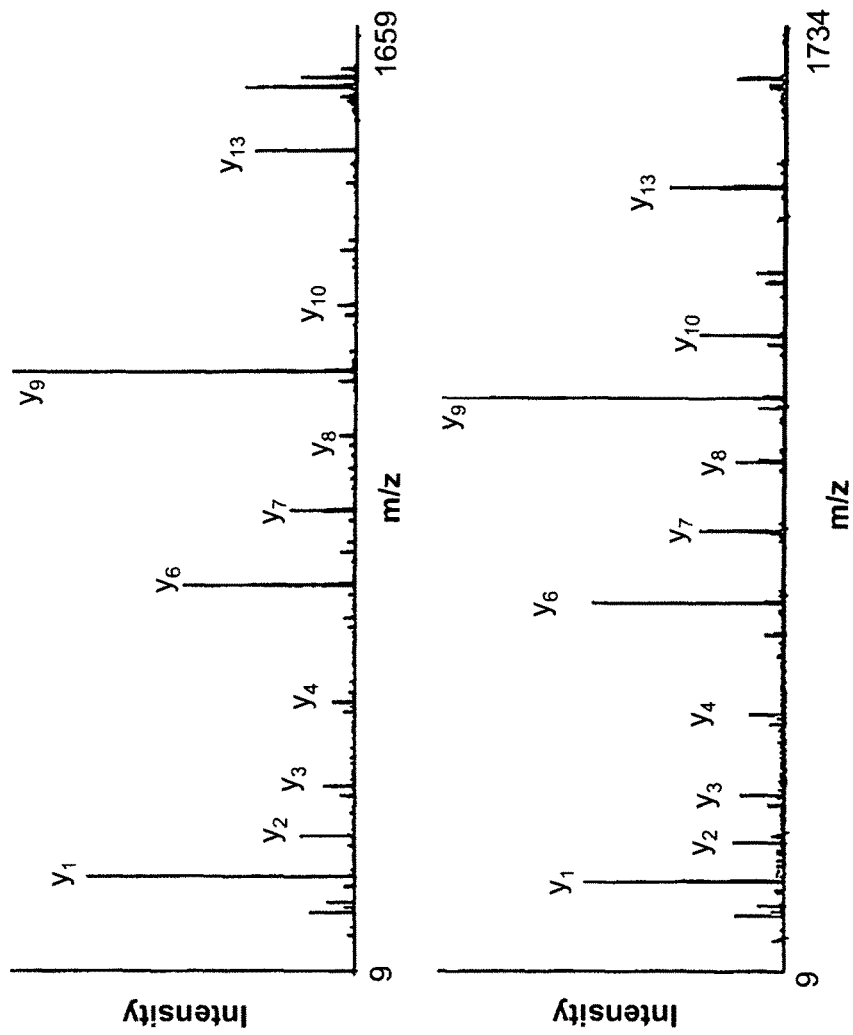

FIG. 12A
*Ala PAL*
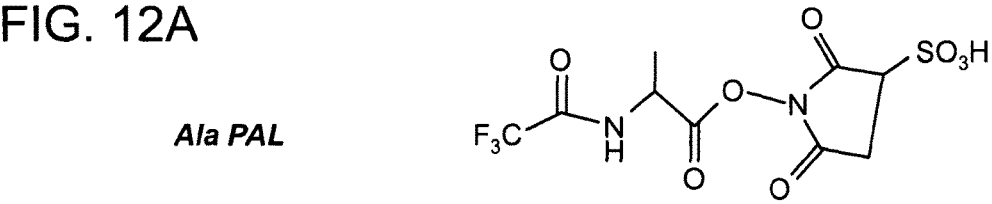
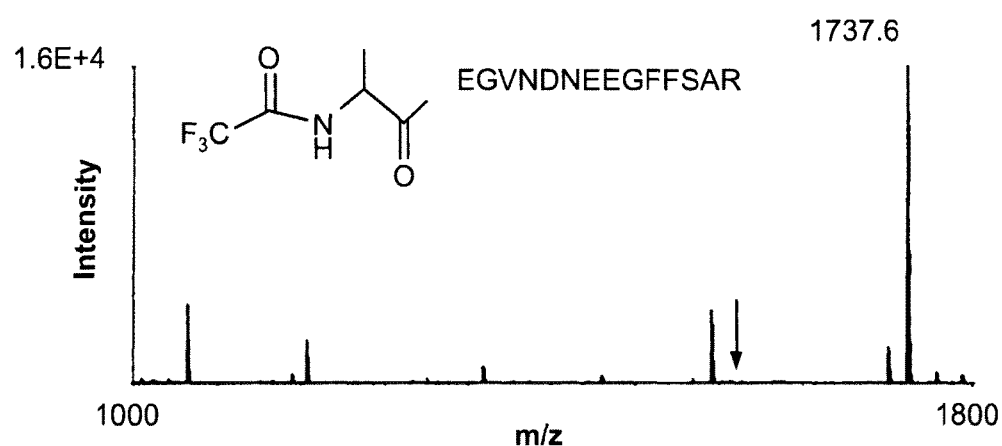
FIG. 12B
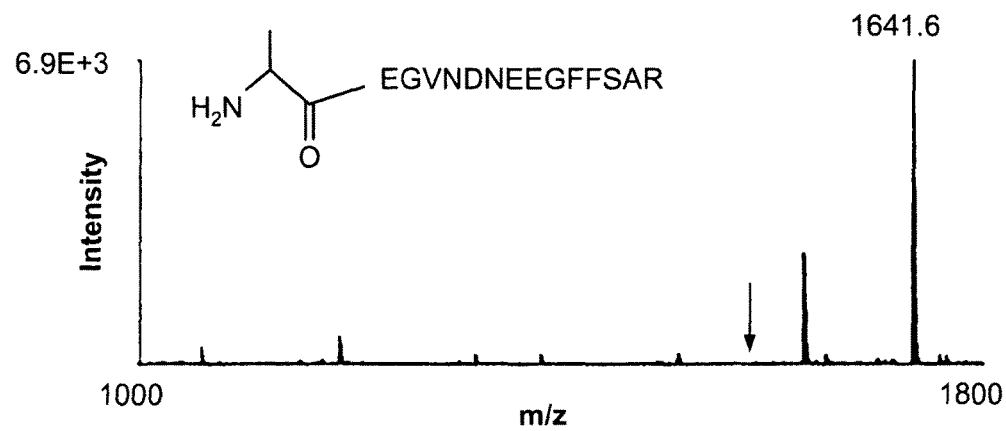

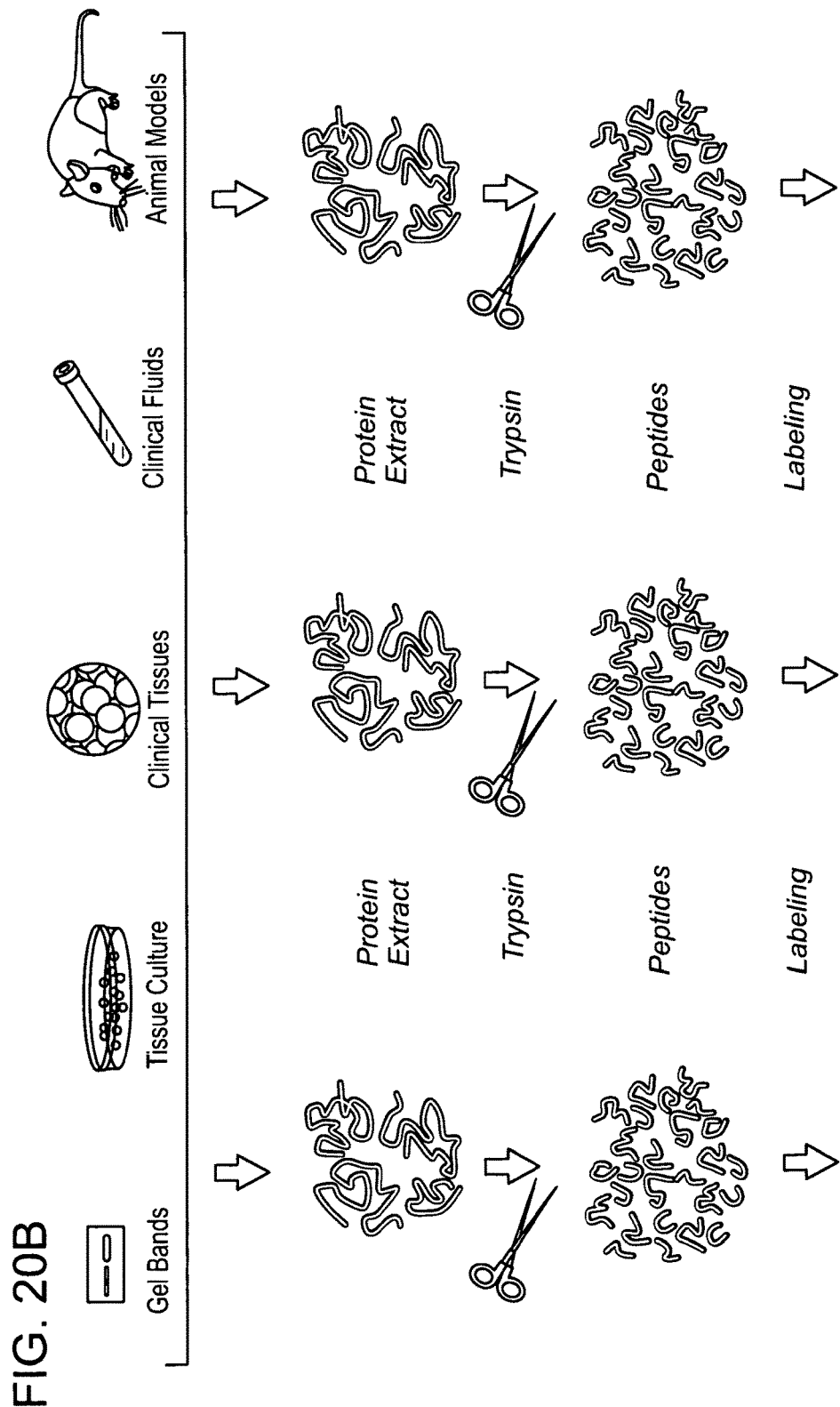

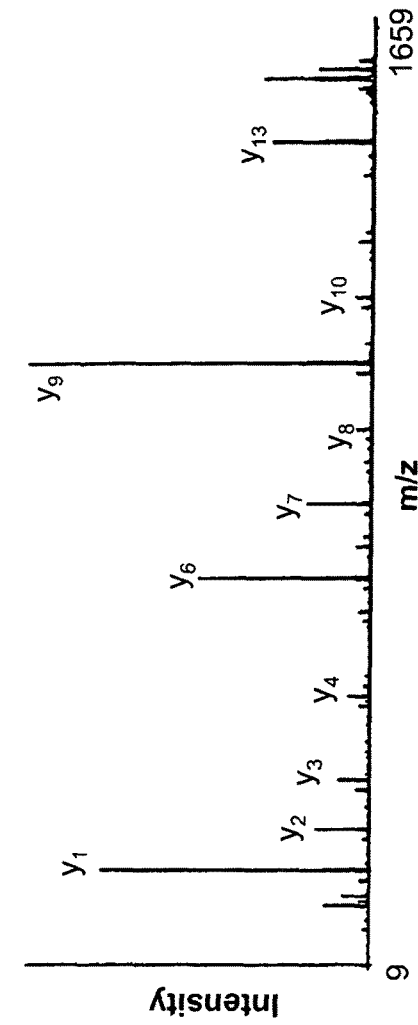
FIG. 22A
*MS/MS Unlabeled*
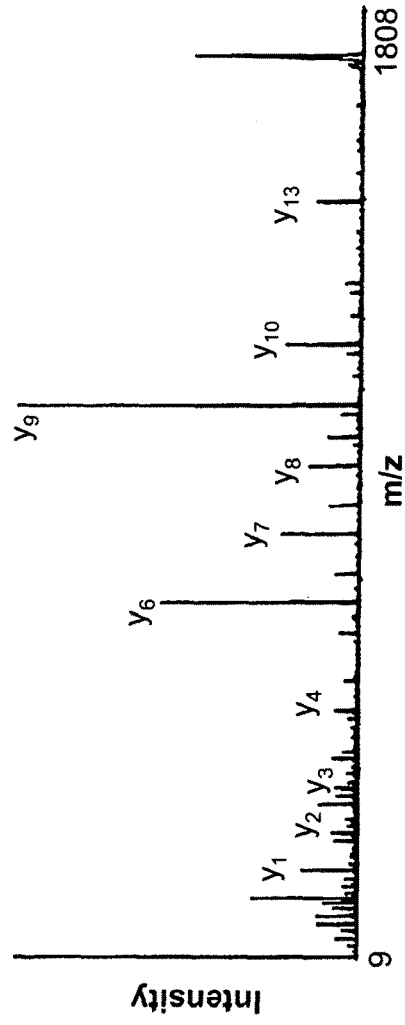
FIG. 22B
*MS/MS Light*

*MS/MS Light-Heavy*

*MS/MS Heavy-Heavy*

FIG. 27 Table 1

| Protein | Actual Ratio | Average Measured Ratio | Error | Standard Deviation | CV |
|---|---|---|---|---|---|
| BSA | 1:1 | 1.1:1 | 9% | 0.15 | 14% |
| Ovalbumin | 3:1 | 2.6:1 | 17% | 0.069 | 18% |
| Beta galactosidase | 1:2 | 1:2.4 | 20% | 0.29 | 12% |
| Beta lactoglobulin | 1:5 | 1:5.8 | 16% | 0.97 | 17% |

FIG. 28 Table 2

| Chemical Label | Number of Samples | Net Mass Added per Reactive Site | Quant Mode | Reactive Site |
|---|---|---|---|---|
| ICAT | 2 | 227, 236 | MS | Cysteine |
| MCAT | 2 | 140, 144 | MS | 1°Amine |
| iTRAQ (4-plex) | 4 | 144 | MS/MS | 1°Amine |
| iTRAQ (8-plex) | 8 | 304 | MS/MS | 1°Amine |
| TMT (2-plex) | 2 | 224, 225 | MS | 1°Amine |
| TMT (6-plex) | 6 | 229 | MS/MS | 1°Amine |
| ICPL (4-plex) | 4 | 106, 110, 112, 116 | MS | 1°Amine |
| β-Ala PAL | 2 | 71, 75 | MS | 1°Amine |
| β-Ala$_2$ PAL | 3 | 141, 145, 149 | MS | 1°Amine |
| β-Ala$_3$ PAL | 4 | 141, 145, 149, 153 | MS | 1°Amine |
| β-Ala$_3$ PAL | 7 | 211, 215, 219, 223, 227, 231, 235 | MS | 1°Amine |
| Gly$^2$ Lys PAL HR | 2 | 246 | MS and MS/MS | 1°Amine |

PROTECTED AMINE LABELS AND USE IN DETECTING ANALYTES

CROSS-REFERENCE TO RELATED APPLICATIONS

This application is a 35 U.S.C. §371 U.S. national entry of International Application PCT/US2010/052731 (WO 2011/047192) having an International filing date of Oct. 14, 2010 which claims the benefit of and priority to U.S. Provisional Patent Application No. 61/278,953, filed Oct. 14, 2009, the contents of which are incorporated herein by reference in their entirety.

TECHNICAL FIELD

The invention is directed towards novel amino acid based compounds, which may be isotopically enriched, and methods of use of such compounds for characterising one or more molecules of a sample by mass spectrometry, the method comprising: (a) reacting the one or more molecules with the amino acid based compound; and (b) characterising the one or more molecules by mass spectrometry.

BACKGROUND OF THE INVENTION

Collective developments in mass spectrometry, separations, enrichment techniques, and related sample processing and data analysis have shifted the experimental focus of proteomics applications from simple protein catalogs to construction of dynamic networks, whereby changes in protein expression and post-translational modification status are monitored as a function of biological state (disease, oxidative stress, etc.) or perturbation (injury, drug treatment, etc.). The ability to quantitatively monitor proteins directly, rather than biological surrogates such as mRNA, and then use these data in models that support predictions in the context of cellular physiology will have a profound impact on human health.

Although quantitative proteomics is still considered an emerging technology with respect to instrumentation and standardization general trends have nonetheless emerged. For example, comparison of cellular proteomes was traditionally performed with two dimensional gel electrophoresis (2DGE) (Gygi, S. P., et al. *Proc Natl Acad Sci USA* 97, 9390-9395 (2000); O'Farrell, P. H. *J Biol Chem* 250, 4007-4021 (1975)). Despite high resolving power, this technique suffers from limited dynamic range, incompatibility with membrane and basic proteins, and low throughput (Baggerman, G., et al. *Comb Chem High Throughput Screen* 8, 669-677 (2005); Wolff, S. et al. *Mol Cell Proteomics* 5, 1183-1192 (2006)). In addition, relative quantification of proteins is usually performed with image analysis software, and hence gel-to-gel variability can yield unacceptably high errors. Recently, LC-MS/MS approaches that utilize stable isotope dilution have been developed for quantitative proteomics, and these methods are collectively displacing 2DGE as the technique of choice for comparison of protein expression and post-translational modification status (Bantscheff, M., et al. *Anal Bioanal Chem* 389, 1017-1031 (2007); Pan, S. et al. *Methods Mol Biol* 367, 209-218 (2007); Gevaert, K. et al. *PROTEOMICS* 8, 4873-4885 (2008)). Proteins or peptides can be labeled with stable isotopes of hydrogen, oxygen, carbon, and/or nitrogen. After labeling, samples are mixed and analyzed by LC-MS/MS and relative abundances determined from the measured ratios of peptide precursors (MS scan) or fragments (MS/MS scan).

As reviewed recently by Pan and Aebersold, stable isotope labeling schemes for quantitative proteomics may be conveniently divided into three classes: (i) metabolic, (ii) enzymatic, and (iii) chemical (Pan, S. et al. *Methods Mol Biol* 367, 209-218 (2007)). The former is typically referred to as SILAC or stable incorporation of labeled amino acids in culture (Ong, S. E. et al. *Mol Cell Proteomics* 1, 376-386 (2002); Veenstra, T. D., et al. *J Am Soc Mass Spectrom* 11, 78-82 (2000)). In this strategy, cells are cultured in normal media or media that contains amino acids enriched with stable isotopes of carbon, nitrogen, or oxygen. After several passages, heavy amino acids are metabolically incorporated into cellular proteins at a level >95%. Because light and heavy cell cultures are combined just prior to lysis, no bias due to sample handling is introduced during subsequent processing steps. Relative quantification is based on measured ratios of peptide precursor abundances in MS scans. Recent reports have extended the concept of metabolic labeling to facilitate quantitative analysis of proteins in animal models (Krüger, M. et al. *Cell* 134, 353-364 (2008); McClatchy, D. B., et al. *J Proteome Res* 6, 2005-2010 (2007); McClatchy, D. B., et al. *Genome Res* 17, 1378-1388 (2007)). Enzymatic incorporation of stable isotopes during protein digestion is another strategy commonly used for quantitative proteomics (Mirgorodskaya, O. A. et al. *Rapid Commun Mass Spectrom* 14, 1226-1232 (2000); Yao, X., et al. *Anal Chem* 73, 2836-2842 (2001)). In this approach protein samples are digested in buffers formulated in either normal ($H_2^{16}O$) or heavy ($H_2^{18}O$) aqueous solutions. Hydrolysis of amide bonds at lysine and arginine (in the case the enzyme trypsin) leads to incorporation of oxygen atoms from water at newly formed peptide C-termini. Relative quantification is based on measured ratios of peptide precursor abundances in MS scans. Unfortunately incorporation of $^{18}O$ is often incomplete, leading to the appearance of doublets that contain one or two $^{18}O$ atoms, respectively, in peptides digested in heavy water.

Chemical labels are synthesized de novo to meet specific physiochemical characteristics, and hence represent the most versatile class of compounds for quantitative proteomics. These reagents can be broadly characterized by their (i) target site for derivatization, (ii) elemental composition of heavy isotopes, (iii) impact on peptide gas phase basicity, (iv) incorporation of affinity tag for enrichment, (v) compatibility with, and quantitative readout in, MS and MS/MS scans, and (vi) compatibility with typical sample processing protocols in proteomics. Each of these properties must be carefully considered during the design of a labeling strategy to maximize analytical figures of merit for the final reagent. For example, the original ICAT reagent targeted free thiol groups in cysteine side chains and included a biotin affinity tag for efficient enrichment of cysteine-containing peptides. However, stable isotopes of deuterium constituted the mass tag, and hence the light and heavy labeled peptides did not co-elute under typical reversed phase chromatographic conditions used in LC-MS/MS. In addition, the relatively large linker scaffold was prone to fragmentation under typical MS/MS conditions, complicating interpretation of peptide sequence data. The ICAT reagent was subsequently re-designed to include $^{13}C$ as the mass tag and a cleavable linker to improve overall performance, although in general this reagent is only applicable to quantification of cysteine-containing proteins (Li, J., et al. *Mol Cell Proteomics* 2, 1198-1204 (2003)).

Similarly, a host of reagents have been developed that target peptide N- and C-termini; details are thoroughly discussed in a recent review by Leitner and Lindner (Leitner, A. & Lindner, W. *J Chromatogr B Analyt Technol Biomed Life Sci* 813, 1-26 (2004)). For example, carboxyl-directed tags will target the side chains of acidic amino acids, in addition to the peptide C-terminus. In practice, the ubiquitous use of trypsin for digestion, results in peptides with an indeterminate number of acidic residues, and hence labeling sites. Conversely the use of reagents that target primary amines generally yields peptides with three or fewer labels. However, the activated esters that are commonly used to target primary amines are unstable in aqueous conditions, and hence use of these reagents often requires organic solvents that must be removed via lyophilization or vacuum centrifugation prior to LC-MS analysis. In addition many of these compounds act as acetylating reagents, reducing the gas phase basicity of peptide primary amines, and leading to a concomitant reduction in ionization efficiency. Quarternary amines can also be used to affix a permanent charge at primary amines; but often these reagents adversely affect fragmentation of peptides under low-energy MS/MS conditions, leading to a reduction in peptide and protein identification.

Despite the limitations described above, the physiochemical properties of small molecule labels can in principle be fine-tuned for optimum performance in quantitative proteomics. The ideal reagent would selectively target peptide side chains or termini, provide rapid and complete derivatization, maintain overall gas phase basicity of peptides, introduce at least a 4-Da mass difference via stable isotopes that do not inductively shift peptide chromatographic elution time with respect to the light counterparts, support labeling of proteins or peptides derived from a wide range of biological samples, and maintain peptide fragmentation patterns typically observed with low-energy MS/MS activation schemes.

SUMMARY OF THE INVENTION

In one aspect, the invention provides a compound of formula I:

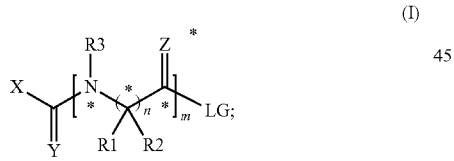

(I)

or a salt thereof,
wherein,
Z* is independently, $^{16}O$ or $^{18}O$ or S;
Y is independently O, S, NH, or N-alkyl;
LG is independently —OH, substituted hydroxyl, wherein the substituted hydroxyl comprises an in-situ activation agent for coupling (e.g. PyBOP/HOBt);
or LG is selected from the following:

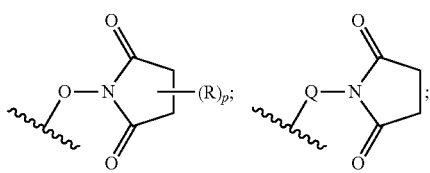

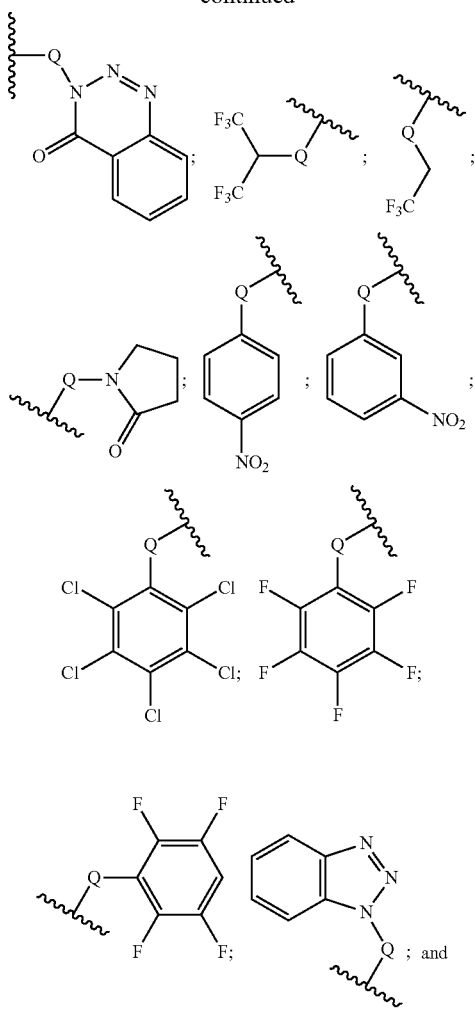

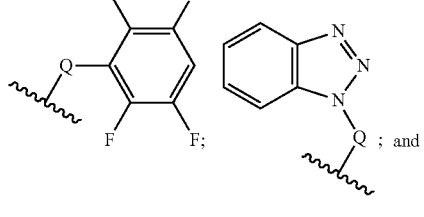

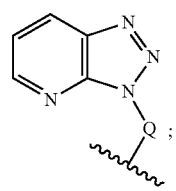

each Q is independently O or S;

each R is independently H, alkyl, aryl, heteroaryl, cycloalkyl, heterocycloalkyl, O-alkyl, N-alkyl-alkyl, S-alkyl, or $SO_3H$, each of which may be optionally substituted;

each X is independently alkyl, heteroalkyl, perfluoroalkyl, haloalkyl, cycloalkyl, heterocycloalkyl, aryl, heteroaryl, O-alkyl, O-cycloalkyl, O-haloalkyl, or $N(R_3)(R_4)$, or $N(R_3)CO(R_4)$, each of which may be optionally substituted;

each $R_3$ is independently H, alkyl, or together with $R_1$ or $R_2$, may form a cycloalkyl or heterocycloalkyl ring;

$R_1$ and $R_2$ are each independently H, alkyl, aryl, or haloalkyl, or a side chain or protected side chain of any of the naturally or unnaturally occurring amino acids, each of which may be optionally substituted;

or $R_2$ is

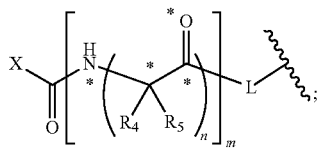

wherein L is $N(R_6)$, where $R_6$ is alkyl, heteroalkyl, haloalkyl, cycloalkyl, heterocycloalkyl, aryl, heteroaryl, each of which may be further substituted;

each $R_4$ and $R_5$ is independently alkyl, heteroalkyl, haloalkyl, cycloalkyl, heterocycloalkyl, aryl, heteroaryl, or a side chain of any of the naturally or unnaturally occurring amino acids, each of which may be further substituted;

each n is independently 1 or 2;
each m is independently 1, 2, 3, or 4;
p is 1, 2, 3, or 4; and
each * represents $^{12}C$, $^{13}C$, $^{14}N$, $^{15}N$, $^{16}O$ or $^{18}O$.

In another aspect, the invention provides a method for characterising one or more molecules of a sample by mass spectrometry, the method comprising: (a) reacting the one or more molecules with a compound of formula I; and (b) characterising the one or more molecules by mass spectrometry.

In another aspect, the invention provides a method for characterising one or more molecules of a sample by mass spectrometry, the method comprising: (a) reacting the one or more molecules with two or more compounds of formula I; and (b) characterising the one or more molecules by mass spectrometry.

DESCRIPTION OF THE DRAWINGS

FIG. 12. MALDI MS spectra of the peptide Glu-Fib (EGVNDNEEGFFSAR) labeled with the light form of Ala PAL, before (A) and after (B) deprotection. Vertical arrow indicates m/z value for unlabeled peptide.

FIG. 27. Table 1. Two solutions were prepared, each containing four standard proteins (bovine serum albumin, beta galactosidase, ovalbumin, and beta lactoglobulin) in ratios listed in Table 1.

FIG. 28. Table 2 provides a brief comparison of PAL with several commercially available labels for quantitative proteomics applications.

DETAILED DESCRIPTION OF THE INVENTION

Figure 1:
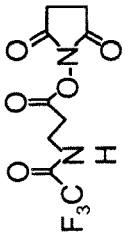
FIG. 1. The PAL strategy leverages chemical building blocks from three classes. Amino acids (middle) serve as mass tag scaffolds and may include stable heavy isotopes of carbon, nitrogen, oxygen, sulfur, and hydrogen. Free amines of the molecular scaffold are protected with chemically reversible (left, top) or irreversible (left, bottom) moieties. The latter contain nitrogen centers to support efficient ionization under typical electrospray- or MALDI-based mass spectrometry analysis. Protected mass tags are activated (right) at the C-terminus using one of several amine-directed esters.
Figure 1:
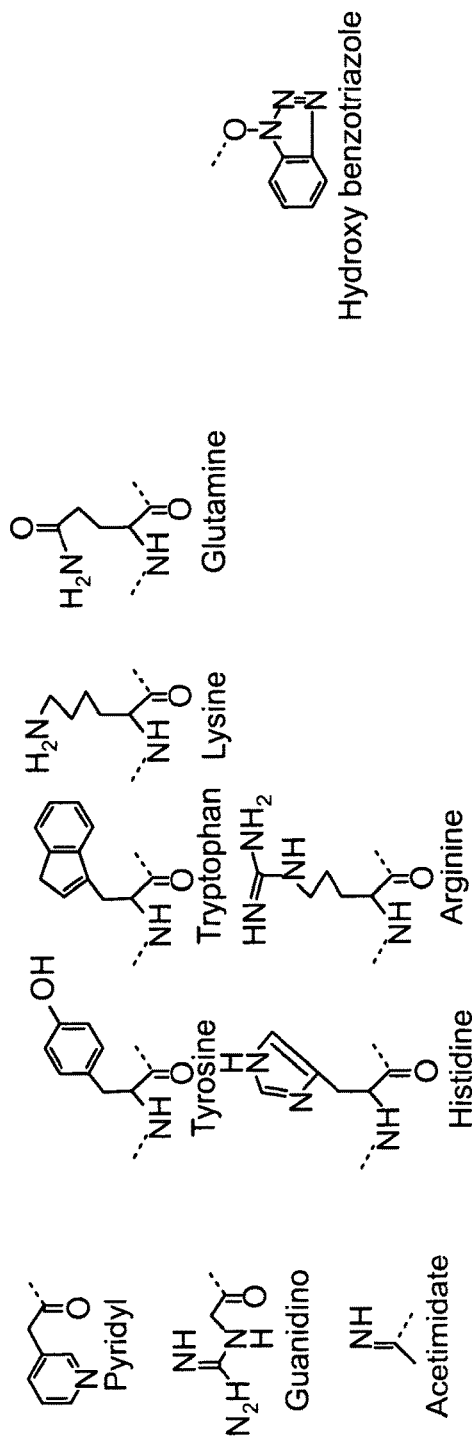

The disclosure herein overcomes the limitations described above by developing labels based on economical, readily available starting materials, and that provide a flexible molecular architecture.

Definitions

Listed below are definitions of various terms used to describe this invention. These definitions apply to the terms as they are used throughout this specification and claims, unless otherwise limited in specific instances, either individually or as part of a larger group.

As used herein, the terms "analyte" or "molecule in a sample" refer to a molecule of interest that may be determined. Non-limiting examples of analytes can include, but are not limited to, proteins, peptides, nucleic acids (both DNA or RNA), carbohydrates, lipids, steroids and/or other small molecules with a molecular weight of less than 1500 daltons. The source of the analyte, or the sample comprising the analyte, is not a limitation as it can come from any source. The analyte or analytes can be natural or synthetic. Non-limiting examples of sources for the analyte, or the sample comprising the analyte, include but are not limited to cells or tissues, or cultures (or subcultures) thereof. Non-limiting examples of analyte sources include, but are not limited to, crude or processed cell lysates, body fluids, tissue extracts or cell extracts.

Still other non-limiting examples of sources for the analyte include but are not limited to fractions from a separations process such as a chromatographic separation or an electrophoretic separation. Body fluids include, but are not limited to, blood, urine, feces, spinal fluid, cerebral fluid, amniotic fluid, lymph fluid or a fluid from a glandular secretion.

Processed cell lysate refers to the cell lysate that is treated, in addition to the treatments needed to lyse the cell, to thereby perform additional processing of the collected material. For example, the sample can be a cell lysate comprising one or more analytes that are peptides formed by treatment of the total protein component of a crude cell lysate with a proteolytic enzyme to thereby digest precursor protein or proteins.

As used herein, "fragmentation" refers to the breaking of a covalent bond. As used herein, "fragment" refers to a product of fragmentation (noun) or the operation of causing fragmentation (verb). It is well accepted that the mass of an atom or molecule can be approximated, often to the nearest whole number atomic mass unit or the nearest tenth or hundredth of an atomic mass unit.

As used herein, "nominal mass" refers to the nearest integer mass of the most abundant isotope of an element. For example the nominal masses of oxygen and nitrogren are 16 and 14, respectively. Similarly, the nominal mass of a molecule is the sum of the nominal masses of the individual elements. The "average mass" refers to the abundance-weighted mass across all stable isotopes of a given element. The average mass of a molecule is then the sum of the average masses of the individual elements. The "monoisotopic mass" of a molecule is the mass represented by the sum of the lowest mass isotopes of all constituent elements in the molecule. For peptides, the monoisotopic mass is typically comprised of the stable isotopes: carbon-12, hydrogen-1, oxygen-16, nitrogen-14, sulfur-32, and phosphorus-31. Those skilled in the art will recognize that the interplay between the natural distribution of stable heavy isotopes and the range of mass resolving power available on different mass spectrometers will impact how reagents are designed for use in quantitative proteomics studies. For example, individual isotopes of a molecule may not be resolved on a low performance mass spectrometer; that is, they will appear as a single peak centered near the molecule's average mass. However, on a high resolution instrument, one will observe the monoisotopic peak along with several higher mass isotopes, each separated from its lower mass neighbor by one mass-to-charge unit. Because the first stable heavy isotope of carbon, with mass of 13, has a natural abundance of approximately 1% relative to carbon 12, one typically sees several isotopes in a high resolution mass spectrum of biomolecules, whereby the so-called isotope cluster extends over 3-5 mass-to-charge units, depending on the mass of the analyte. As a result, use of a combination of stable isotopes that yield a minimum of a 4 dalton mass shift allows relative quantitation of biomolecules on both low- and high-resolution mass spectrometers. Experienced practioners will also readily appreciate that distinct mass defects associated with constituent elements of biomolecules results in isotopic fine structure within the heavy isotope peaks that is visible on ultrahigh resolution mass spectrometers. For example, the abundant isotopes of oxygen have masses of 15.9949 and 17.9992, while the abundant isotopes of carbon have masses of 12.00000 and 13.00336, and the abundant isotopes of nitrogen have masses of 14.0031 and 15.0001, respectively. Hence, if one uses the $^{18}$O isotope in one chemical tag of a set, the additional 2 mass units (over the isotope of oxygen having a mass of 15.9949) can, for example, be compensated for in a different chemical tag of the set comprising $^{16}$O by incorporating, elsewhere in the tag, two carbon $^{13}$C atoms, instead of two $^{12}$C atoms, two $^{15}$N atoms, instead of two $^{14}$N atoms or even one $^{13}$C atom and one $^{15}$N atom, instead of a $^{12}$C and a $^{14}$N, to compensate for the $^{18}$O. In this way the two different chemical stages of the set will have the same nominal mass, but their lowest mass isotopes (apparent monoisotopic species) will appear as a single peak in low- and high-resolution mass spectra. However, under ultrahigh resolution conditions, each of the lowest mass isotopes for different chemical tags comprising the set will be detected as a distinct peak in the mass spectrum.

As used herein, "isotopically enriched" refers to a compound (e.g. labeling reagent or chemical tag) that has been enriched synthetically with one or more heavy atom isotopes (e.g. stable isotopes such as Deuterium, $^{13}$C, $^{15}$N, $^{18}$O, $^{37}$Cl or $^{81}$Br). Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass.

As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "chemical tag", "mark" and derivatives of these terms, are interchangeable and refer to a moiety suitable to mark, or that has marked, an analyte for determination.

As used herein, "natural isotopic abundance" refers to the level (or distribution) of one or more isotopes found in a compound based upon the natural abundance of an isotope or isotopes in nature.

The term "alkyl," as used herein, refers to saturated, straight- or branched-chain hydrocarbon moieties containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl moieties include, but are not limited to, methyl, ethyl, propyl, isopropyl, n-butyl, tert-butyl, neopentyl, n-hexyl, heptyl, octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl moiety.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen in a given structure with the specified substituent group. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,
—OH, protected hydroxy,
—$NO_2$, —CN,
—$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino,
—O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl,
—C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl,
—$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl,
—$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH— aryl, —OCONH— heteroaryl, —OCONH— heterocycloalkyl,
—NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$— aryl, —$NHCO_2$— heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, —$NHC(S)NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)

NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH— aryl, —SO$_2$NH— heteroaryl, —SO$_2$NH— heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

The term "sample" as used herein refers to biomolecules to be analyzed by the methods and reagents of this invention. The term "subject" as used herein refers to an organism from which biomolecules are derived. Subjects can be prokaryotes or eukaryotes. When the subject is a human, the subject may be referred to herein as a patient.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein.

Compounds of the Invention

In one aspect, the invention provides a compound of formula I:

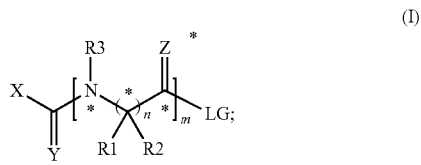

(I)

or a salt thereof,
wherein,

Z* is independently, $^{16}$O or $^{18}$O or S;

Y is independently O, S, NH, or N-alkyl;

LG is independently —OH, substituted hydroxyl, wherein the substituted hydroxyl comprises an in-situ activation agent for coupling (e.g. PyBOP/HOBt);

or LG is selected from the following:

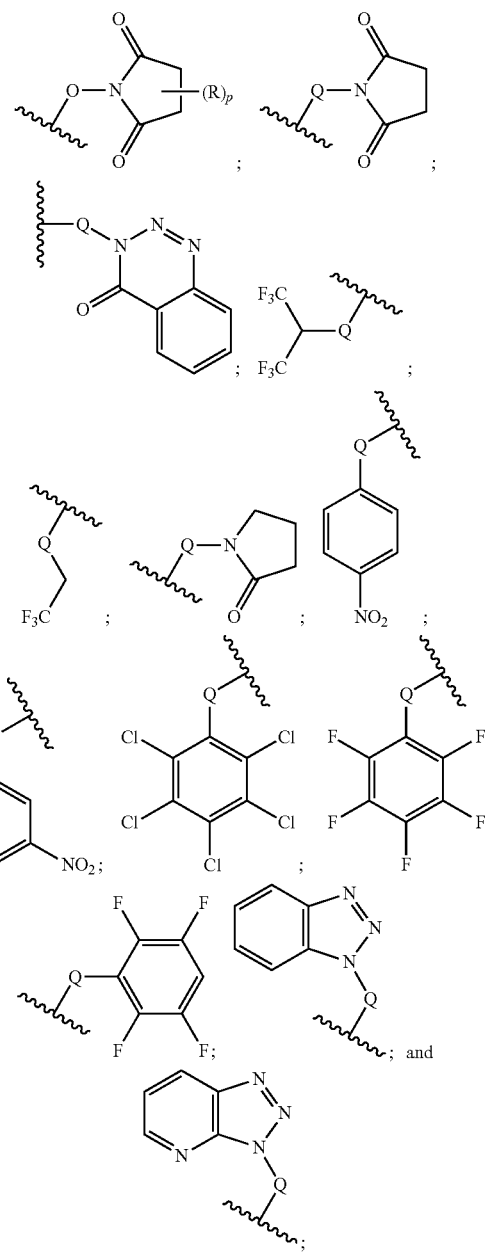

each Q is independently O or S;

each R is independently H, alkyl, aryl, heteroaryl, cycloalkyl, heterocycloalkyl, O-alkyl, N-alkyl-alkyl, S-alkyl, or SO$_3$H, each of which may be optionally substituted;

each X is independently alkyl, heteroalkyl, perfluoroalkyl, haloalkyl, cycloalkyl, heterocycloalkyl, aryl, heteroaryl, O-alkyl, O-cycloalkyl, O-haloalkyl, or N(R$_3$)(R$_4$), or N(R$_3$)CO(R$_4$), each of which may be optionally substituted;

each R$_3$ is independently H, alkyl, or together with R$_1$ or R$_2$, may form a cycloalkyl or heterocycloalkyl ring;

R$_1$ and R$_2$ are each independently H, alkyl, aryl, or haloalkyl, or a side chain or protected side chain of any of the naturally or unnaturally occurring amino acids, each of which may be optionally substituted;

or R$_2$ is

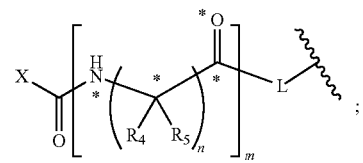

wherein L is N(R$_6$), where R$_6$ is alkyl, heteroalkyl, haloalkyl, cycloalkyl, heterocycloalkyl, aryl, heteroaryl, each of which may be further substituted;

each R$_4$ and R$_5$ is independently alkyl, heteroalkyl, haloalkyl, cycloalkyl, heterocycloalkyl, aryl, heteroaryl, or a side chain of any of the naturally or unnaturally occurring amino acids, each of which may be further substituted;

each n is independently 1 or 2;
each m is independently 1, 2, 3, or 4;
p is 1, 2, 3, or 4; and
each * represents $^{12}$C, $^{13}$C, $^{14}$N, $^{15}$N, $^{16}$O or $^{18}$O.

In one embodiment, Y is O and each X is independently alkyl, perfluoroalkyl, or O-alkyl, each of which may be optionally substituted.

In a further embodiment, each alkyl or O-alkyl is substituted by heterocycloalkyl, aryl, heteroaryl, or amino, each of which may be further substituted.

In another embodiment, X is

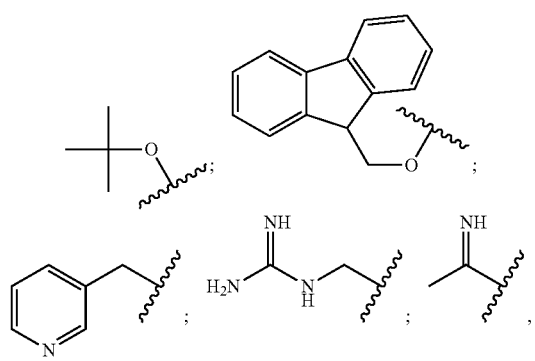

or CF$_3$, each of which may be further substituted.

In certain embodiments, R$_1$ and R$_2$ are each independently H, optionally substituted alkyl, or R$_2$ is

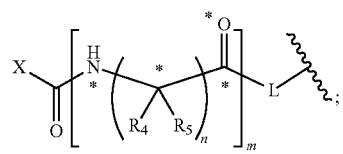

wherein L is N(R$_6$), where R$_6$ is alkyl, heteroalkyl, haloalkyl, cycloalkyl, heterocycloalkyl, aryl, heteroaryl, each of which may be further substituted.

In a further embodiment, R$_1$ and R$_2$ are each independently substituted with OR$_7$, SR$_7$, N(R$_7$)(R$_8$), C(O)R$_9$, optionally substituted aryl, or optionally substituted heteroaryl;

wherein each R$_7$ is independently H, alkyl, or aryl;
R$_8$ is H, alkyl, or aryl; and
R$_9$ is OH, NH$_2$, O-alkyl, NH-alkyl, or N-alkyl-alkyl;

In a further embodiment, each R$_1$ is independently H, methyl, i-propyl, s-butyl, i-butyl,

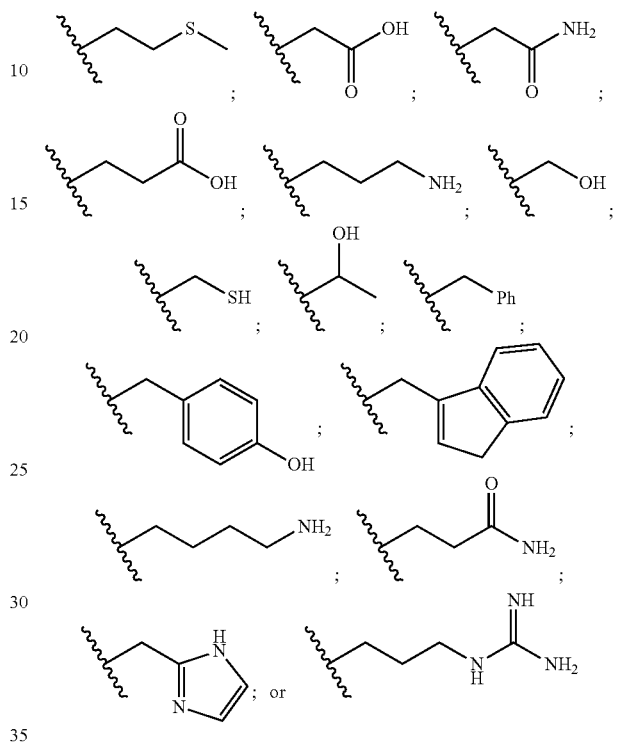

In certain embodiments, all * represent $^{12}$C, $^{14}$N, or $^{16}$O. In certain embodiments, at least two of * is $^{13}$C or $^{15}$N. In certain embodiments, at least four of * are $^{13}$C or $^{15}$N. In certain embodiments, any * is $^{13}$C, $^{15}$N, or $^{18}$O.

In certain embodiments, 2 of * are $^{15}$N. In certain embodiments, 2 of * are $^{13}$C.

In certain embodiments, X is

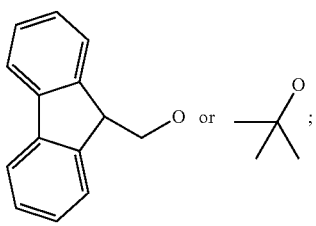

Y and Z are O;
R$_1$, R$_2$ and R$_3$ are —H;
m=2 and n=1; and
LG is selected from the group consisting of:

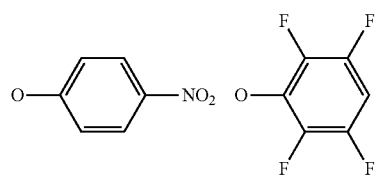

In another embodiment, the invention provides a compound of formula II:

(II)

wherein,
X is alkyl, heteroalkyl, perfluoroalkyl, or haloalkyl;
$R_1$ and $R_2$ are each independently H or alkyl;
or $R_2$ is wherein L is $N(R_6)$, where $R_6$ is alkyl, heteroalkyl, haloalkyl, cycloalkyl, heterocycloalkyl, aryl, heteroaryl, each of which may be further substituted;
each R is independently H, OH, or $SO_3H$;
n is 1 or 2;
m is 1, 2, 3, or 4;
p is 1, 2, 3, or 4; and
each * represents $^{12}C$, $^{13}C$, $^{14}N$, $^{15}N$, $^{16}O$ or $^{18}O$.

In one embodiment, X is $CF_3$, and each $R_1$ and $R_2$ are H.
In another embodiment, all * represent all * represent $^{12}C$, $^{14}N$ or $^{16}O$.
In certain embodiments, at least two of * is $^{13}C$ or $^{15}N$.
In various embodiments, at least four of * are $^{13}C$, $^{15}N$ or $^{18}O$.

In another embodiment, the invention provides a compound of formula II-a:

(II-a)

wherein,
X is alkyl, heteroalkyl, or haloalkyl;
$R_1$ and $R_2$ are each independently H or alkyl;
or $R_2$ is wherein L is $N(R_6)$, where $R_6$ is alkyl, heteroalkyl, haloalkyl, cycloalkyl, heterocycloalkyl, aryl, heteroaryl, each of which may be further substituted;
each R is independently H, OH, or $SO_3H$;
n is 1 or 2;
m is 1, 2, 3, or 4;
p is 1, 2, 3, or 4; and
each * represents $^{12}C$, $^{13}C$, $^{14}N$, $^{15}N$, $^{16}O$ or $^{18}O$.

In one embodiment, X is $CF_3$, and each $R_1$ and $R_2$ are each independently H or methyl.
In other embodiments, all * represent $^{12}C$, $^{14}N$ or $^{16}O$.
In certain embodiments, at least two of * is $^{13}C$ or $^{15}N$.
In another embodiment, at least four of * are $^{13}C$, $^{15}N$ or $^{18}O$.

In certain embodiments, the invention provides a compound of formula III:

(III)

wherein,
X is alkyl, heteroalkyl, or haloalkyl;
$R_1$ and $R_2$ are each independently H or alkyl;
or $R_2$ is independently H, alkyl, aryl, heteroaryl, cycloalkyl, heterocycloalkyl, O— alkyl, N-alkyl-alkyl, S-alkyl, or the side chain of any of the naturally or unnaturally occurring amino acids, each of which may be optionally substituted,
or $R_2$ is wherein L is $N(R_6)$, where $R_6$ is alkyl, heteroalkyl, haloalkyl, cycloalkyl, heterocycloalkyl, aryl, heteroaryl, each of which may be further substituted;
each R is independently H, OH, or $SO_3H$;
n is 1 or 2;
m is 1, 2, 3, or 4;
p is 1, 2, 3, or 4; and
each * represents $^{12}C$, $^{13}C$, $^{14}N$, $^{15}N$, $^{16}O$ or $^{18}O$.

In one embodiment, X is $CF_3$, and each $R_1$ and $R_2$ are H.
In another embodiment, all * represent $^{12}C$, $^{14}N$ or $^{16}O$.
In certain embodiments, at least two of * is $^{13}C$ or $^{15}N$.
In various embodiments, at least four of * are $^{13}C$, $^{15}N$ or $^{18}O$.

In other embodiments, at least eight of * are $^{13}C$, $^{15}N$ or $^{18}O$.

In still other embodiments, at least eight of * are $^{13}C$ or $^{15}N$ and at least two of O* are $^{18}O$.

In certain embodiments, the invention provides a compound of formula III-a:

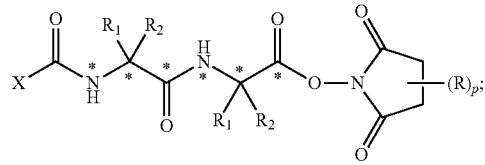

(III-a)

wherein,

X is alkyl, heteroalkyl, or haloalkyl;

$R_1$ and $R_2$ are each independently H or alkyl;

or $R_2$ is independently H, alkyl, aryl, heteroaryl, cycloalkyl, heterocycloalkyl, O-alkyl, N-alkyl-alkyl, S-alkyl, or the side chain of any of the naturally or unnaturally occurring amino acids, each of which may be optionally substituted, or $R_2$ is

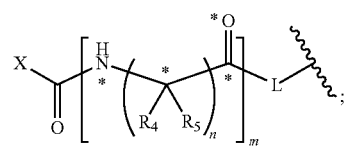

wherein L is $N(R_6)$, where $R_6$ is alkyl, heteroalkyl, haloalkyl, cycloalkyl, heterocycloalkyl, aryl, heteroaryl, each of which may be further substituted;

each R is independently H, OH, or $SO_3H$;

n is 1 or 2;

m is 1, 2, 3, or 4;

p is 1, 2, 3, or 4; and each * represents $^{12}C$, $^{13}C$, $^{14}N$, $^{15}N$, $^{16}O$ or $^{18}O$.

In certain embodiments, X is $CF_3$, and each $R_1$ is H.

In other embodiments, $R_2$ is

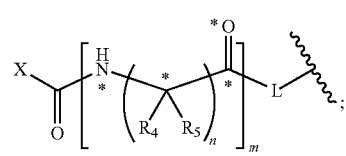

wherein L is $N(R_6)$, where $R_6$ is alkyl, heteroalkyl, haloalkyl, cycloalkyl, heterocycloalkyl, aryl, heteroaryl, each of which may be further substituted.

In a further embodiment, L is NH-alkylene.

In other embodiments, all * represent $^{12}C$, $^{14}N$, or $^{16}O$.

In certain embodiments, at least two of * is $^{13}C$ or $^{15}N$.

In various embodiments, at least four of * are $^{13}C$, $^{15}N$ or $^{18}O$.

In certain embodiments, any * is $^{13}C$, $^{15}N$, or $^{18}O$.

In certain embodiments, 2 of * are $^{15}N$. In certain embodiments, 2 of * are $^{13}C$.

In certain embodiments, X is

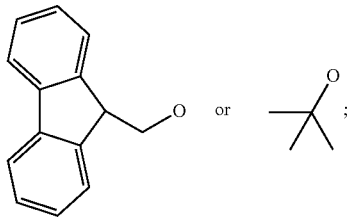

Y and Z are O;

$R_1$, $R_2$ and $R_3$ are —H;

m=2 and n=1; and

LG is selected from the group consisting of:

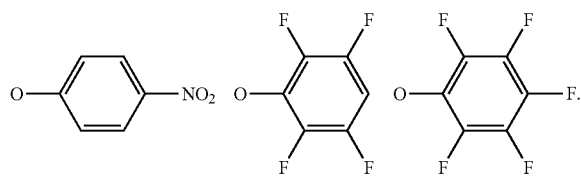

In certain embodiments, X is

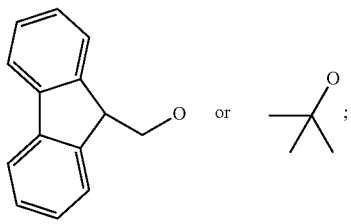

$R_1$ and $R_2$ are —H; and $(R)_p$ is —H or —$SO_3H$.

In another aspect, the invention provides a method for characterising one or more molecules of a sample by mass spectrometry, the method comprising: (a) reacting the one or more molecules with a compound of formula I; and (b) characterising the one or more molecules by mass spectrometry.

In another aspect, the invention provides a method for characterising one or more molecules of a sample by mass spectrometry, the method comprising: (a) reacting the one or more molecules with two or more compounds of formula I; and (b) characterising the one or more molecules by mass spectrometry.

In certain embodiments, the invention provides a method as described above further comprising the step of extracting the one or more molecules from the sample.

In other embodiments, the invention provides a method as described above further comprising the step of digesting the sample with at least one enzyme to partially, or fully, degrade components of the sample prior to performing step reacting the sample with the compound of formula I.

In a further embodiment, the enzyme is a proteolytic enzyme.

In another further embodiment, the proteolytic enzyme is trypsin, papain, pepsin, ArgC, LysC, V8 protease, AspN, pronase, chymotrypsin or carboxypeptidease C.

In certain embodiments, the one or more molecules of the sample is selected from a protein, a peptide, a polypeptide, an amino acid, a nucleic acid, carbohydrates, lipids, steroids, small molecules and mixtures thereof.

In a further embodiment, the one or more molecules is selected from a protein, peptide, and mixtures thereof.

In various embodiments, the sample is a tissue culture, clinical tissues, clinical fluids, animal fluids, animal tissues, or gel bands.

In other embodiments, the invention provides a method as described above further comprising the step of extracting the one or more molecules from the sample.

In certain embodiments, the invention provides a method as described above wherein the two or more compounds of formula I have a differing number of isotopically labelled atoms.

In other embodiments, the invention provides a method as described above wherein the one or more molecules are detected after reaction with compounds of formula I, by simultaneously identifying their masses by mass spectrometry.

In a further embodiment, the masses are distinguished by isotopic labels.

In another embodiment, the invention provides a set of compounds, comprising two or more compounds of Formula I or Formula II herein, wherein each of the two or more compounds has the same structure but differs in mass from each of the other compounds due to differing numbers of atoms of $^{12}C$, $^{13}C$, $^{14}N$, $^{15}N$, $^{16}O$ or $^{18}O$. In certain embodiments, the set includes two compounds represented by one of the structures:

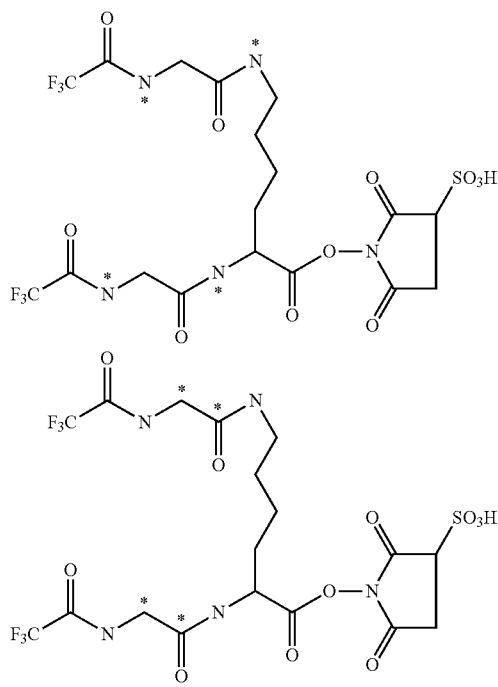

wherein each * represents $^{15}N$ or $^{13}C$, and
wherein the two compounds differ in mass by about 0.02524 Da.

Exemplary syntheses of the compounds of the invention can be found in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound.

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Molecular Building Blocks

As described above a goal of the invention was to develop stable isotope-based labels for quantitative proteomics that combined figures of merit previously unavailable in a single compound: 1.) a minimum 4 Da mass difference between light and heavy isotopomers to facilitate use on low resolution instruments; 2.) utilize stable isotopes of carbon, nitrogen, and oxygen to optimize use with reversed phase separations in LC-MS; 3.) molecular architecture that does not adversely affect labeled peptide hydrophobicity, ionization efficiency, or MS/MS fragmentation; 4.) compatible with peptide labeling in aqueous solution to minimize sample manipulation and enable on-column reactions; 5.) facile and high yield synthesis; 6.) economical, with a materials cost of less than $100 per 1 mg of reagent. Based on these criteria, we chose a synthesis strategy that encompasses three molecular building blocks. The central scaffold is one or a combination of amino acids and carries stable isotopes of carbon, nitrogen, or oxygen for the mass tag (FIG. 1, middle). An amine-directed activating group was coupled to the amino acid C-terminus to facilitate labeling of peptides at N-termini and lysine side chains (FIG. 1, right). These components achieved points #1-3 described above. For improved aqueous stability of our labels (point #4, above), the free amine on the central scaffold was protected with either (i) a chemically reversible linkage that allows regeneration of a free amine prior to LC-MS/MS (FIG. 1, top left), or (ii) an irreversibly bound moiety that contains a high-basicity nitrogen group (FIG. 1 bottom left). Trifluoroacetate (TFA) in particular is an attractive choice to protect the amine terminus. Although historically used as a protecting group for peptide synthesis, TFA has recently been replaced by Boc and Fmoc, primarily due to the latters' favorable deprotection kinetics and compatibility with solid-phase synthesis. However, the compatibility of TFA with aqueous reaction conditions made it an ideal candidate for use in proteomics labeling reagents.

All building block reagents listed in FIG. 1 are readily available, economical, and collectively provide flexibility in the design of specific labeling compounds. Our experience to date indicates that yields from these syntheses exceed 50% on a routine basis (points #5, 6). The labeling strategy described above is referred to as Protected Amine Labels (PAL).

Protected Amine Labels: β-alanine Duplex Reagent (β-Ala PAL)

Figure 2A:
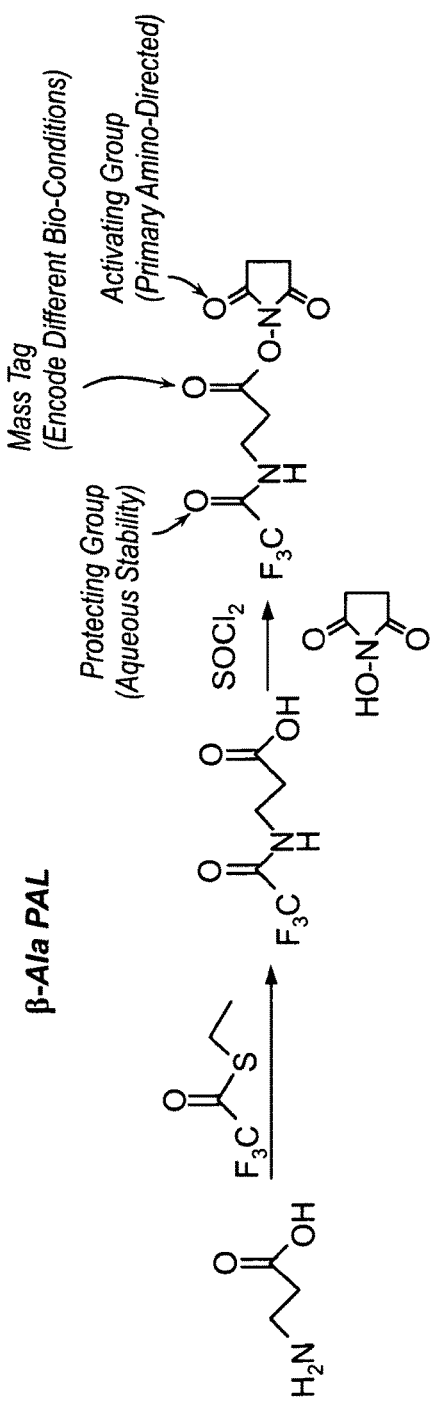
FIG. 2. (A) Synthetic scheme for β-Ala PAL reagents. (B) Experimental workflow. Proteins are isolated from gel bands, cultured cells, primary tissues, or animal models, digested with trypsin, and the resulting peptides are labeled with light and heavy versions of β-Ala PAL. Primary amines are regenerated prior to LC-MS/MS by incubation at pH ~11.5 for 30 min. Abundance ratios for peptide precursors that are separated by a mass-to-charge (m/z) value equal to (n×4)/z, where n is the number of peptide primary amine groups and z is the peptide charge state, provide relative quantification for peptides in each biological condition.
Figure 2B:
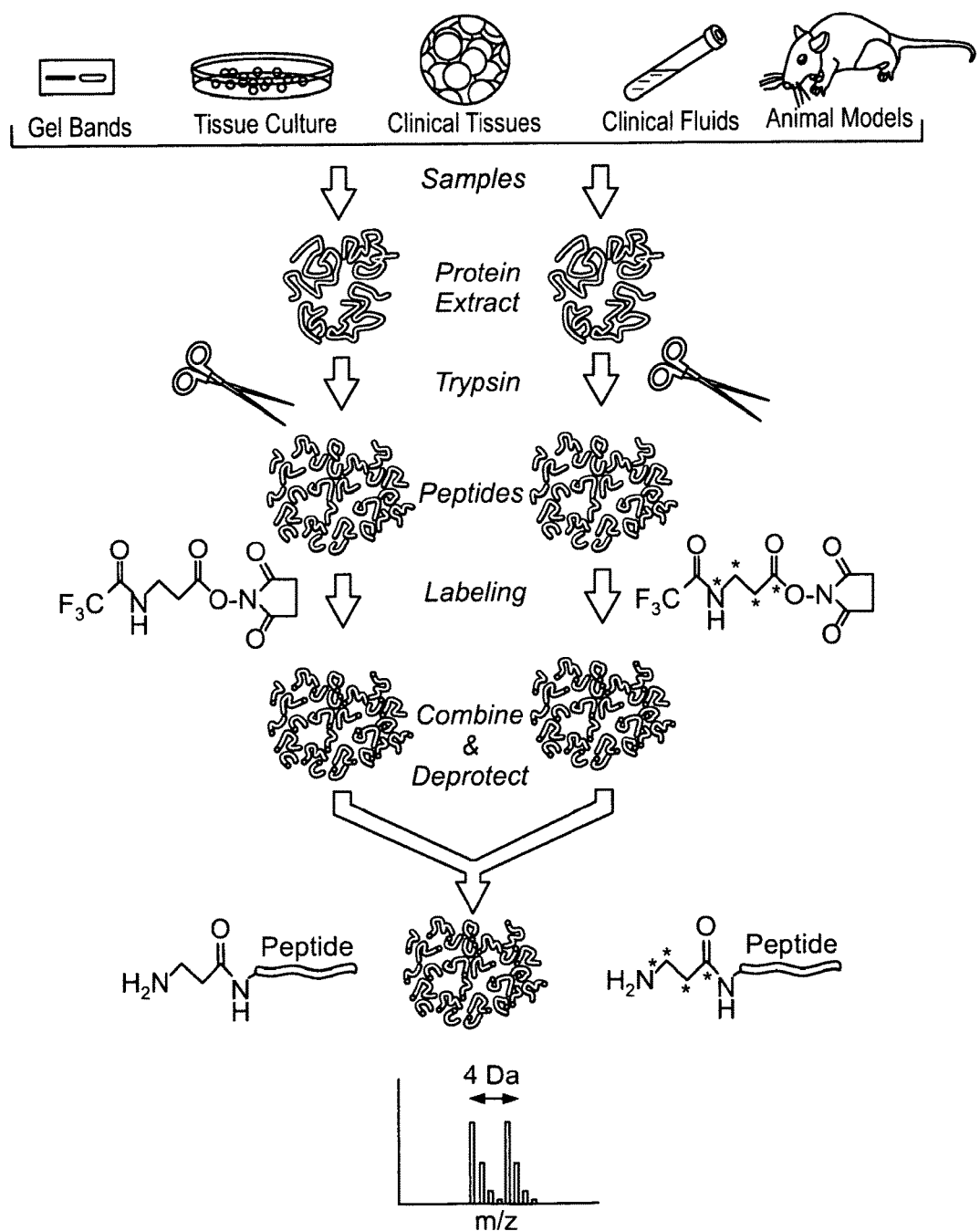
Figure 3A:
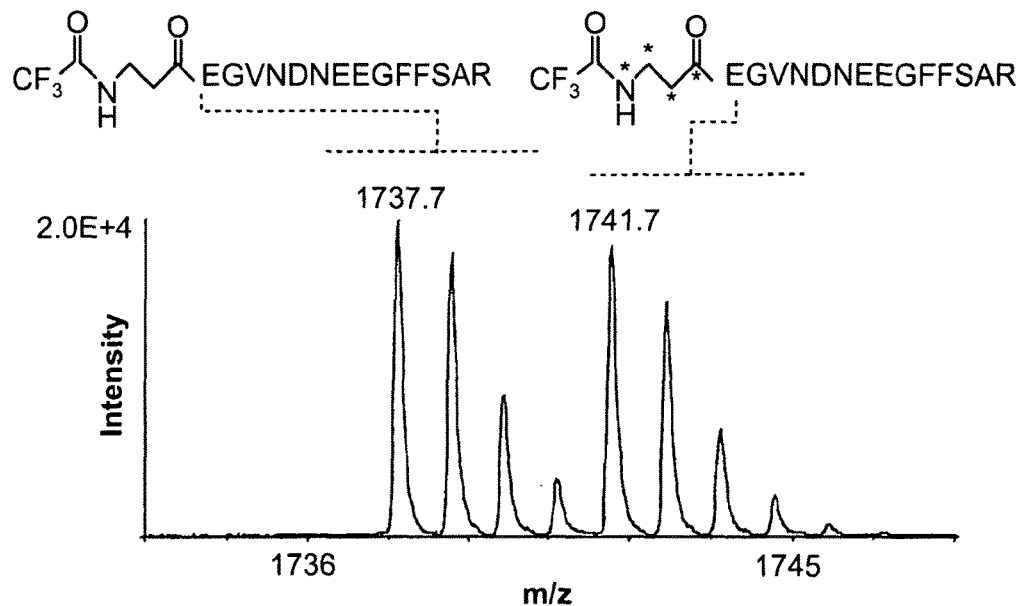
FIG. 3. MALDI MS spectra of the peptide Glu-Fib (EGVNDNEEGFFSAR) labeled in a 1:1 ratio with light and heavy β-Ala PAL, before (A) and after (B) deprotection.
Figure 3B:
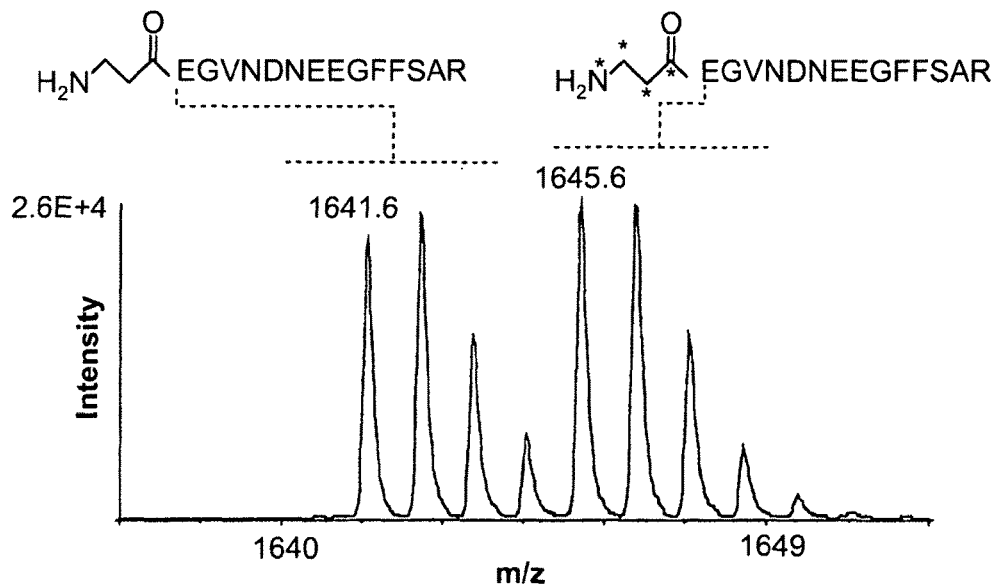
Figures 4C, 5A:
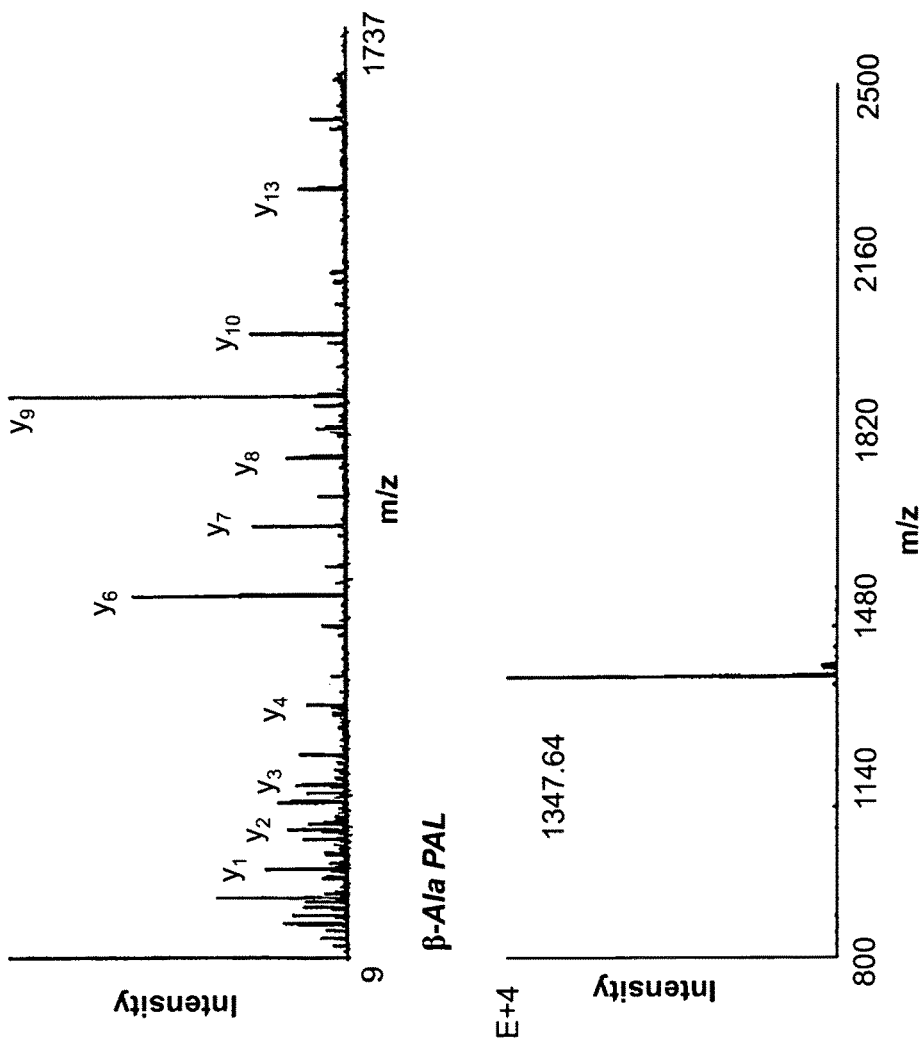
FIG. 4. MALDI MS/MS spectra of Glu-Fib peptide (EGVNDNEEGFFSAR) in (A) native and β-Ala PAL labeled (B and C) forms. PAL chemistry does not significantly alter distribution of fragment ions. Fragments containing the peptide N- and C-terminus are indicated as $b_n$ and $y_n$, respectively.
FIG. 5. MALDI MS spectra of the peptide Substance P (RPKPQQFFGLM) in (A) native and β-Ala PAL labeled (B and C) forms. PAL chemistry efficiently labels both peptide free amines and lysine side chains.

FIG. 2 shows an experimental workflow for quantitative proteomics based on use of β-alaine protected amino labels (β-Ala PAL). Labeling reagents were synthesized as shown in FIG. 2A. As described in the experimental section below, the free amine of β-alanine was first blocked with S-ethyl-tri-fluorothioacetate, and then activated at the C-terminus by coupling to a 2-sulfo-n-hydroxysuccinimide in thionyl chloride and DMF; this synthesis was repeated for isotopically enriched ($^{15}N_1$, $^{13}C_3$) β-alaine, to yield both light and heavy molecules (FIG. 2A). Next (FIG. 2B), proteins derived from a variety of sample sources (purified proteins, gel bands, cell culture, animal models, clinical tissues, etc.) were enzymatically digested, typically with trypsin, to yield a mixture of peptides. After labeling with light and heavy versions of β-Ala PAL, the samples were mixed and free amine termini were regenerated by incubation at pH~12 for 60 min. While other protecting groups may be used (FIG. 1, top left), the procedures for their removal are less amenable for subsequent mass spectrometry-based analysis—e.g., 95% trifluoroacetic acid (Boc) or 20% piperidine in DMF (Fmoc). Finally labeled peptides were analyzed by standard proteomics methods (LC-ESI-MS and MS/MS or MALDI-MS and MS/MS), to yield isotope clusters separated on the m/z axis by (n×4)/z, where n is the number of peptide primary amine groups (typically the N-terminus plus one or more lysines) and z is the peptide charge state. FIG. 3A shows an example of the peptide [Glu1]-FibrinopeptideB (EGVNDNEEGFF-SAR) labeled in a 1:1 ratio with light and heavy β-Ala PAL, and detected in MS mode before deprotection at m/z 1737.7 and 1741.7, respectively. Derivatization was >99% complete, as evidenced by the lack of detected signal for the unlabeled peptide. These observations demonstrate that hydrolysis of the tri-fluoroacetyl group does not occur to an appreciable extent in under the conditions used for peptide derivatization. If necessary, excess reagent may be quenched by addition of hydroxylamine. FIG. 3B shows the same labeled peptides after regeneration of the β-alanine free amine group at m/z 1641.6 and 1645.6, respectively. Deprotection is essentially quantitative, and we observed no evidence of deamidation at the asparagine residues. FIG. 4 shows MS/MS spectra for the Glu-Fib peptide in native (A) and β-Ala PAL labeled (light, B and heavy, C) forms. The fragment spectra are essentially super imposable, demonstrating that PAL chemistry does not adversely affect peptide fragmentation during MS/MS analysis.

Figure 5B:
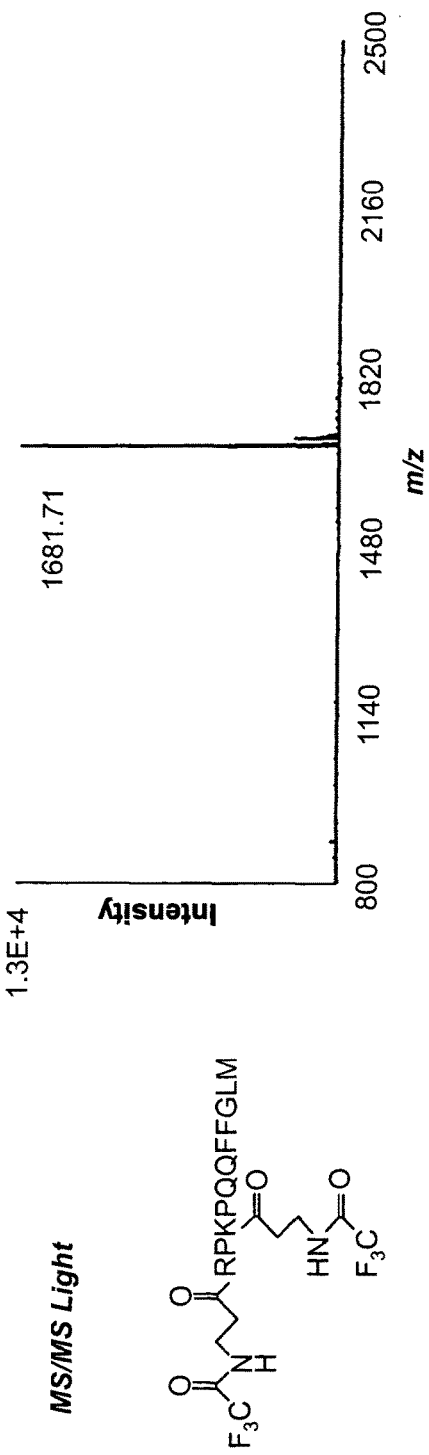
Figure 5C:
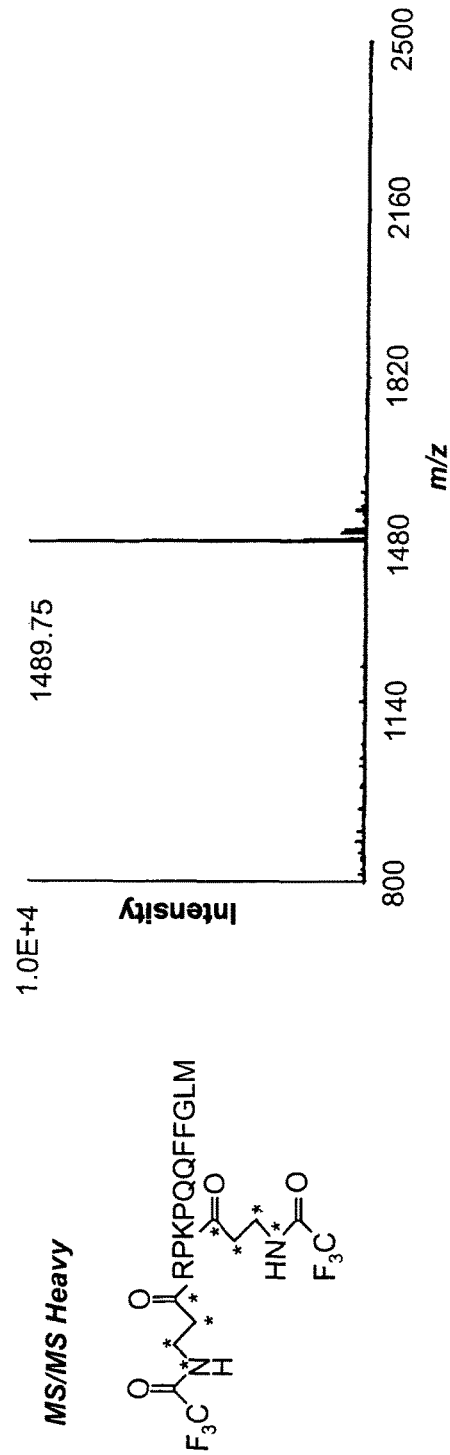

To verify reactivity at the primary amine of a lysine side chain, the peptide Substance P, RPKPQQFFGLM, was labeled with the light form of β-Ala PAL. FIG. 5 shows an MS spectrum of the unlabeled peptide (A), along with the labeled and protected (B) and de-protected (C) forms. These data demonstrate that PAL labeling chemistry is equally efficient, both in terms of coupling and regeneration of a free amine, at peptide N-termini and lysine side chains. In addition, although this peptide contains two glutamine residues, no deamidation was observed as a result of the deprotection step.

Figure 6A:
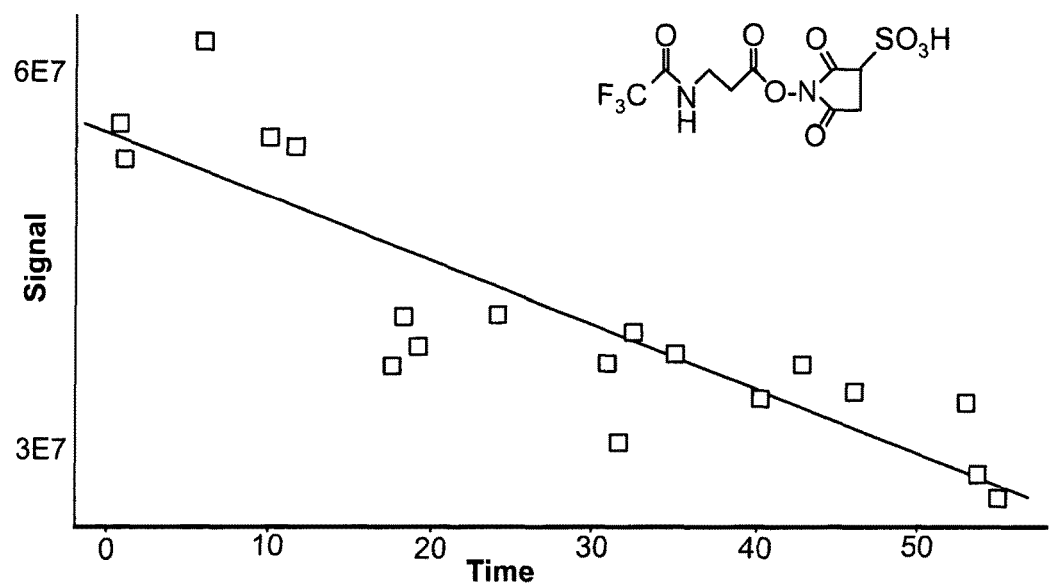
FIG. 6. Aqueous stability of (A) protected β-Ala PAL and (B) n-methyl piperazine acetic acid (iTRAQ) reagents. MS intensity was recorded at regular intervals for each molecule by flow injection analysis. Endpoints represent a signal intensity that corresponds to ~50% of the value at time zero for each reagent, respectively.
Figure 6B:
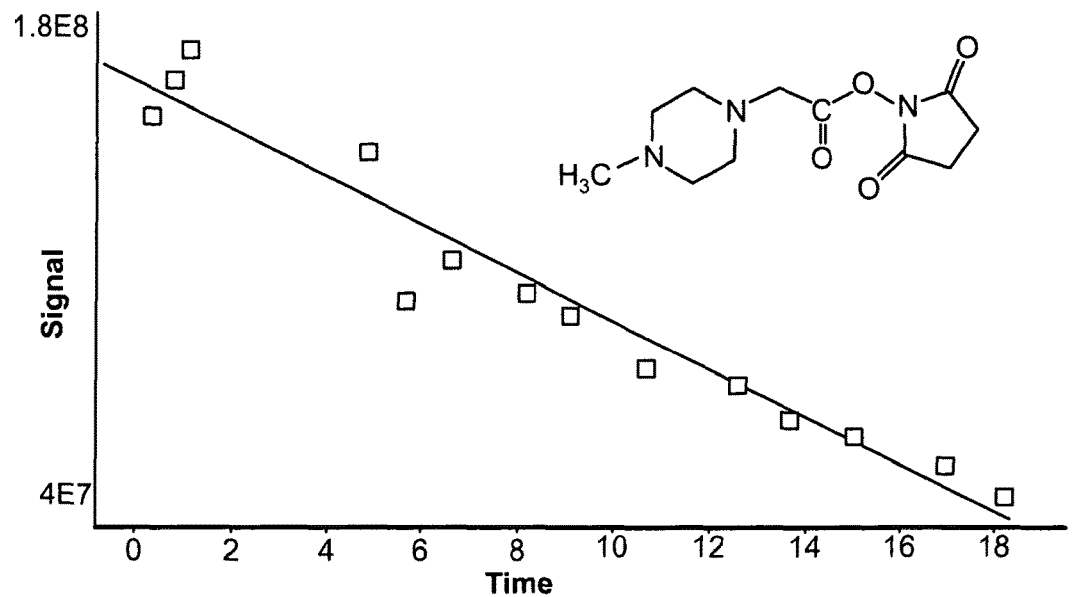
Figure 7A:
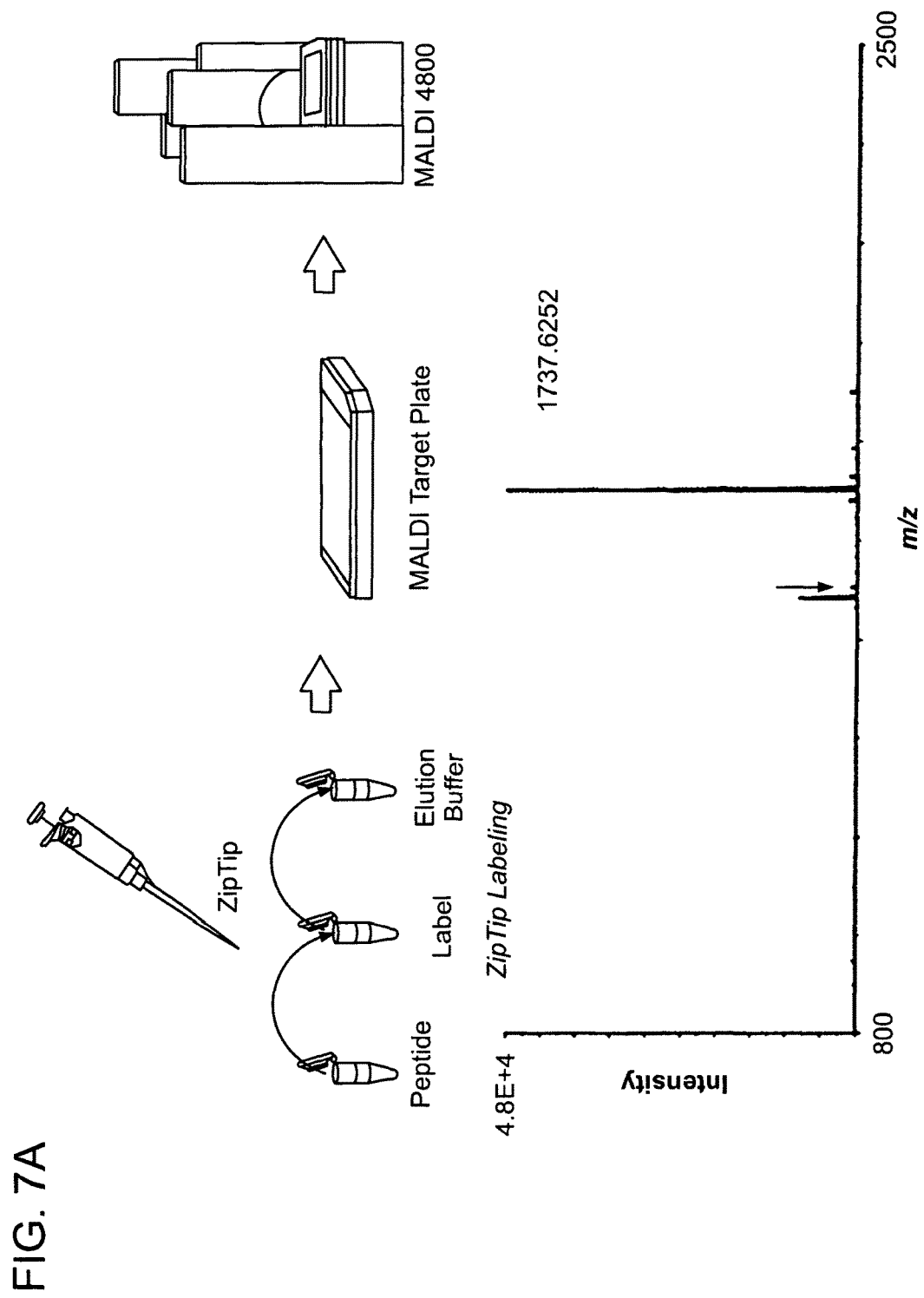
FIG. 7. Solid phase β-Ala PAL labeling of Glu-Fib peptide (EGVNDNEEGFFSAR) in (A) Zip-Tip format prior to MALDI analysis (vertical arrow indicates m/z value for native peptide); (B) native peptide on-column prior to LC-MS analysis; and (C) after labeling with β-Ala PAL.

Regarding the stability of these labels as compared to iTRAQ, a commercially available label based on N-methyl piperazine and targeted to primary amines via N-hydroxysuccinimide ester chemistry. Flow injection analysis was performed on freshly prepared, 100 μg aliquots of each reagent, solubilized in aqueous buffer, pH 2. Triplicate injections were performed at regular time intervals until the MS signal reached approximately 50% of its original starting value. FIG. 6 shows decay curves for the light form of β-Ala PAL (A) and iTRAQ (B), respectively. These data demonstrate that PAL reagents exhibited enhanced aqueous stability as compared to commercial reagents that utilized similar activation (e.g., NHS ester) chemistry. Given these results the next step was to explore the potential to perform labeling reactions after peptides were captured on reversed phase HPLC resin. The ability to label peptides directly on-column can streamline sample preparation methods and also improve overall yield and detection limits by obviating the need for lyophilization, as is often done when using commercially available labeling reagents that require organic reaction conditions. As a test an aliquot of Glu-Fib peptide was loaded onto a reversed phase Zip-Tip pipette tip. Next, freshly prepared β-Ala PAL (light form, aqueous buffer, pH 8.5) was aspirated 5 times across Glu-Fib bound on the reversed phase resin in the pipette tip. A solution of 80% acetonitrile with 0.1% TFA was used to elute peptides directly onto a MALDI target plate. FIG. 7A shows a MS spectrum of β-Ala PAL Glu-Fib; the vertical arrow indicates the m/z region where native (e.g., unlabeled) peptide would appear, indicating that on-column labeling efficiency is equivalent to that observed in solution phase.

Figure 7B:
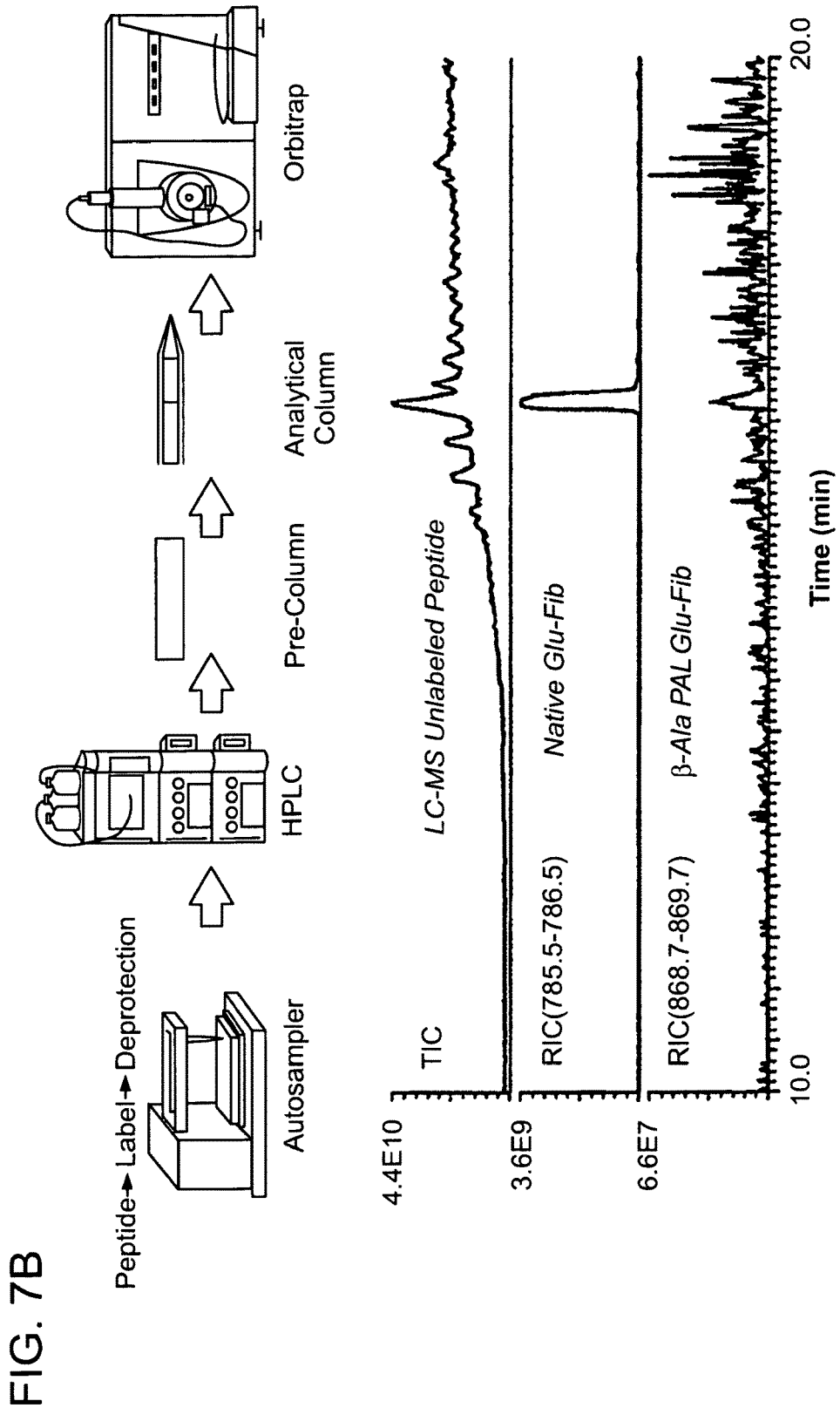
Figure 7C:
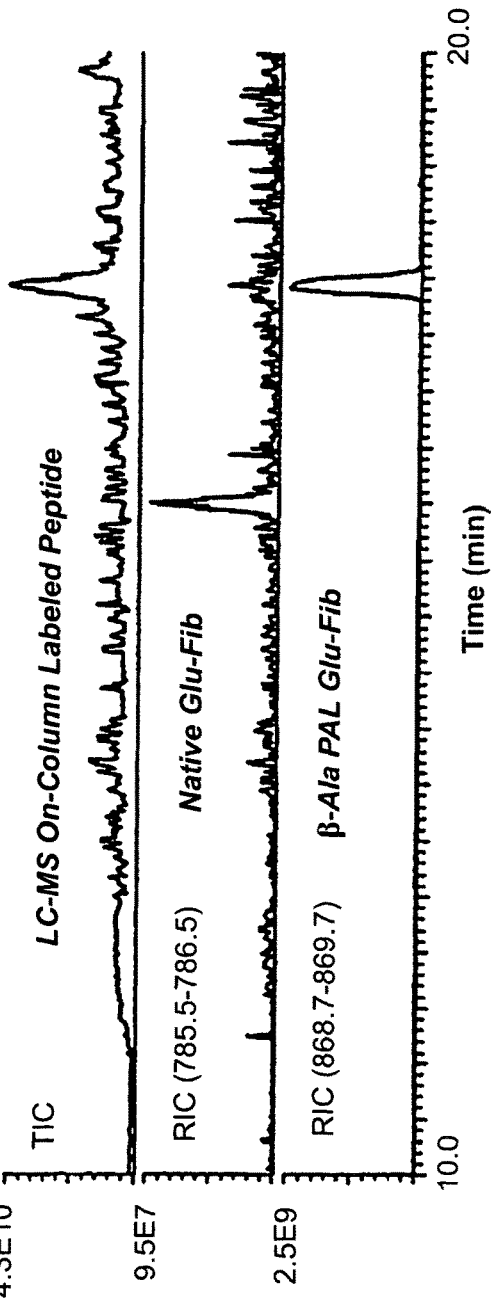
Figure 8A:
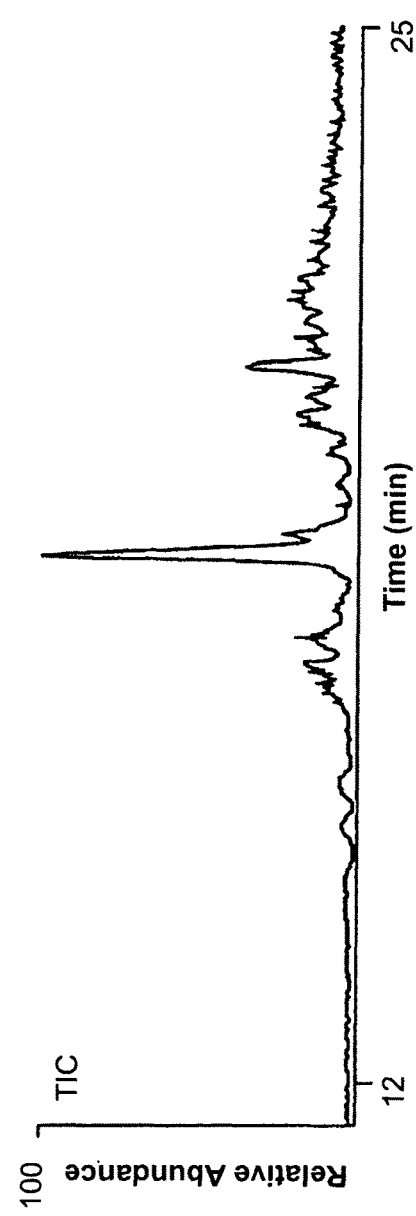
FIG. 8. (A) Total ion chromatogram (TIC) for LC-MS analysis of Glu-Fib peptide (EGVNDNEEGFFSAR). Reconstructed ion chromatograms (RIC) for Glu-Fib labeled with (B) iTRAQ, (C) β-Ala PAL, and (D) ICPL reagents. (E) Reconstructed ion chromatogram (RIC) for the native (unlabeled) peptide.
Figures 8B, 8C:
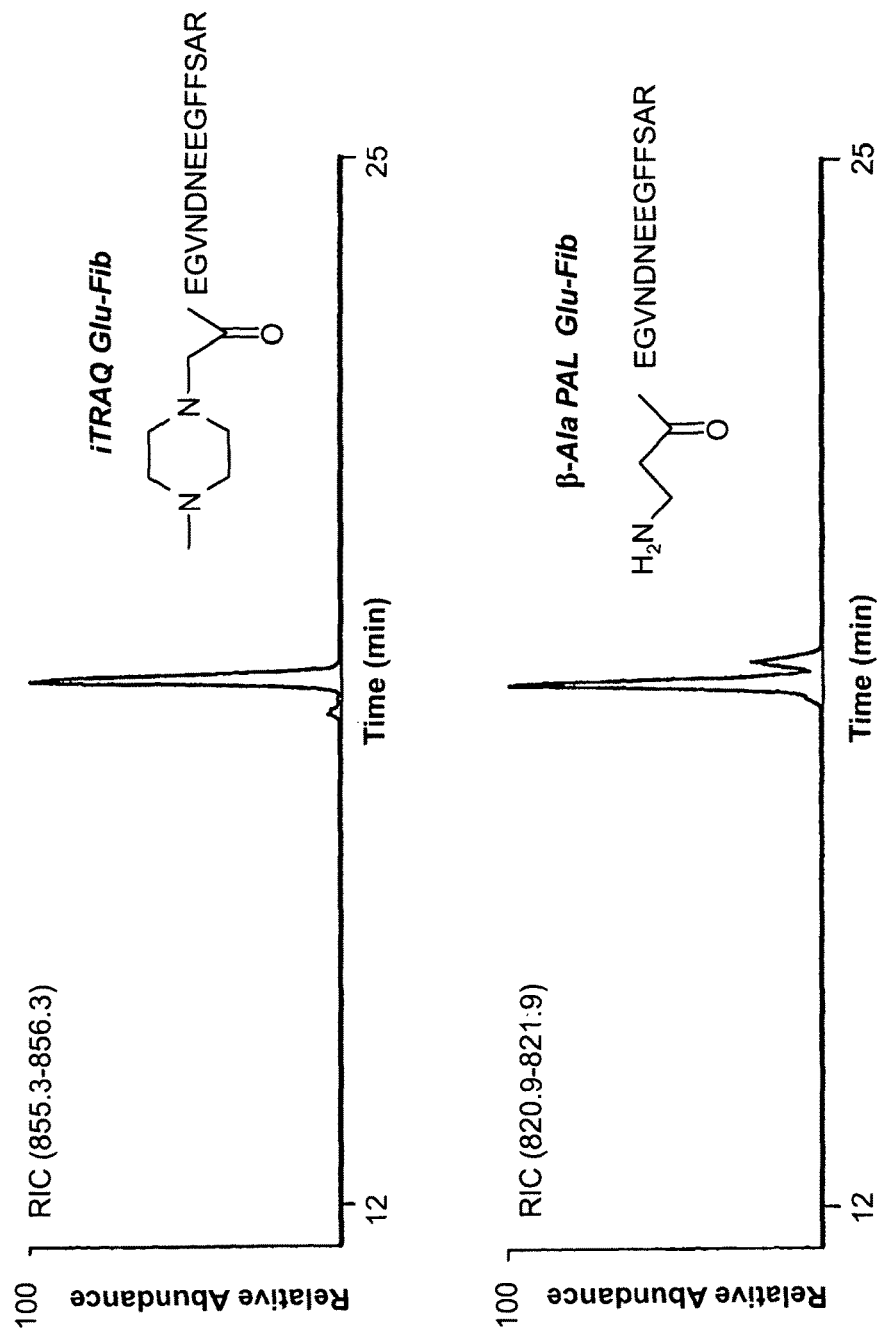
Figure 8D:
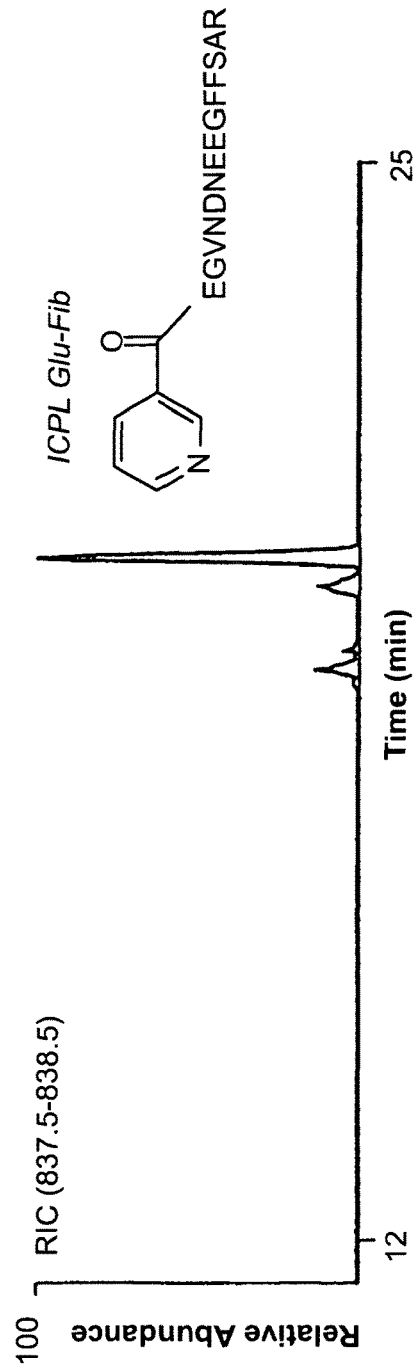
Figure 8E:
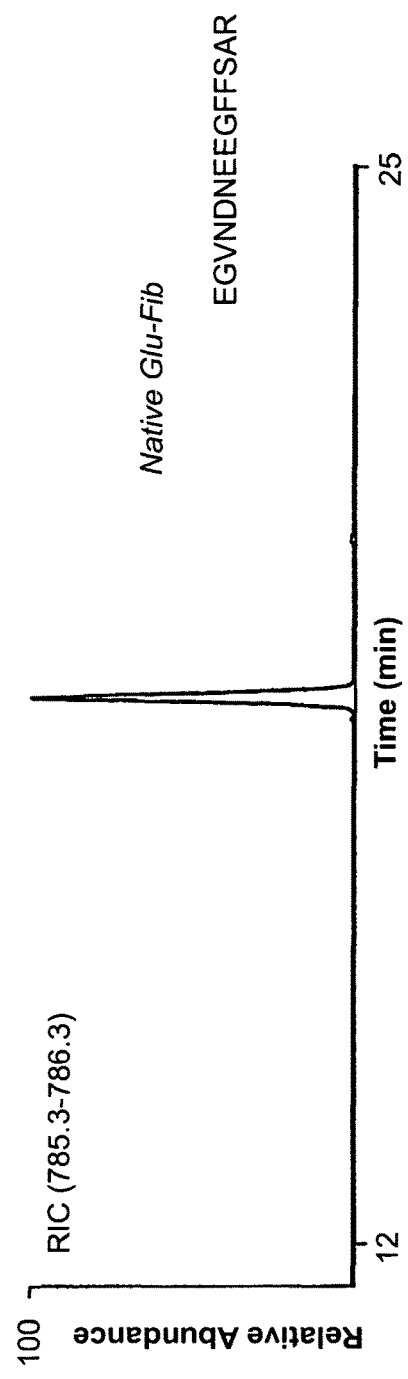

Although the Zip-Tip format is effective for sample clean-up in preparation for MALDI-based analysis, it is less amenable for LC-MS. In this case peptides would be captured on a pre- or de-salting column that was configured in a vented column assembly to facilitate rapid loading and washing of samples and reagents, prior, to LC-MS analysis. To emulate this mode of operation, the peptide Glu-Fib was pressure-loaded onto a fused silica capillary packed with POROS 10R2 reversed phase resin. After rinsing with 0.1% acetic acid, this column was placed in-line between a HPLC pump and analytical column with integrated electrospray emitter (FIG. 7B). Next, an organic solvent gradient was used to elute peptides from the columns and directly into the mass spectrometer. FIG. 7B shows a total ion chromatogram (TIC, top) followed by reconstructed ion chromatograms (RIC) for the m/z range corresponding to the native (middle) and labeled (bottom) Glu-Fib peptide. As expected, signal was only detected for the unlabeled peptide. Next, Glu-Fib was reloaded on the precolumn and rinsed with an aqueous solution containing β-Ala PAL. After a final rinse with 0.1% acetic acid, the precolumn was placed back online and peptides were gradient eluted directly into the mass spectrometer. FIG. 7C shows the TIC (top) followed by RICs for the m/z range corresponding to the native (middle) and labeled (bottom) Glu-Fib peptide. Here nearly complete conversion of Glu-Fib to the labeled form was observed (compare FIG. 7B middle with 7C bottom). Collectively these results demonstrate that PAL chemistry is compatible with labeling in aqueous conditions, and hence facilitates on-column peptide derivatization and analysis via both MALDI and LC-MS.

To verify the general chromatographic performance of PAL labeled peptides, a mixture of native Glu-Fib was prepared along with the same peptide labeled with (i) β-Ala PAL, (ii) N-methyl piperazine acetic acid (iTRAQ), and (iii) nicotinic acid (ICPL). Next, this sample was analyzed by LC-MS/MS. FIG. 8 shows (A) total ion chromatograph, along with reconstructed ion chromatographs (RIC, B-E) for each version of Glu-Fib, including the unlabeled peptide. Although nicotinic acid significantly shifted the LC retention time, both β-Ala PAL- and iTRAQ-labeled peptides exhibited elution times nearly identical to the native peptide. Collectively, these data demonstrate that PAL chemistry does not dramatically alter peptide hydrophobicity, and is compatible with reversed phase chromatography typically used in quantitative proteomics studies.

Figure 9A:
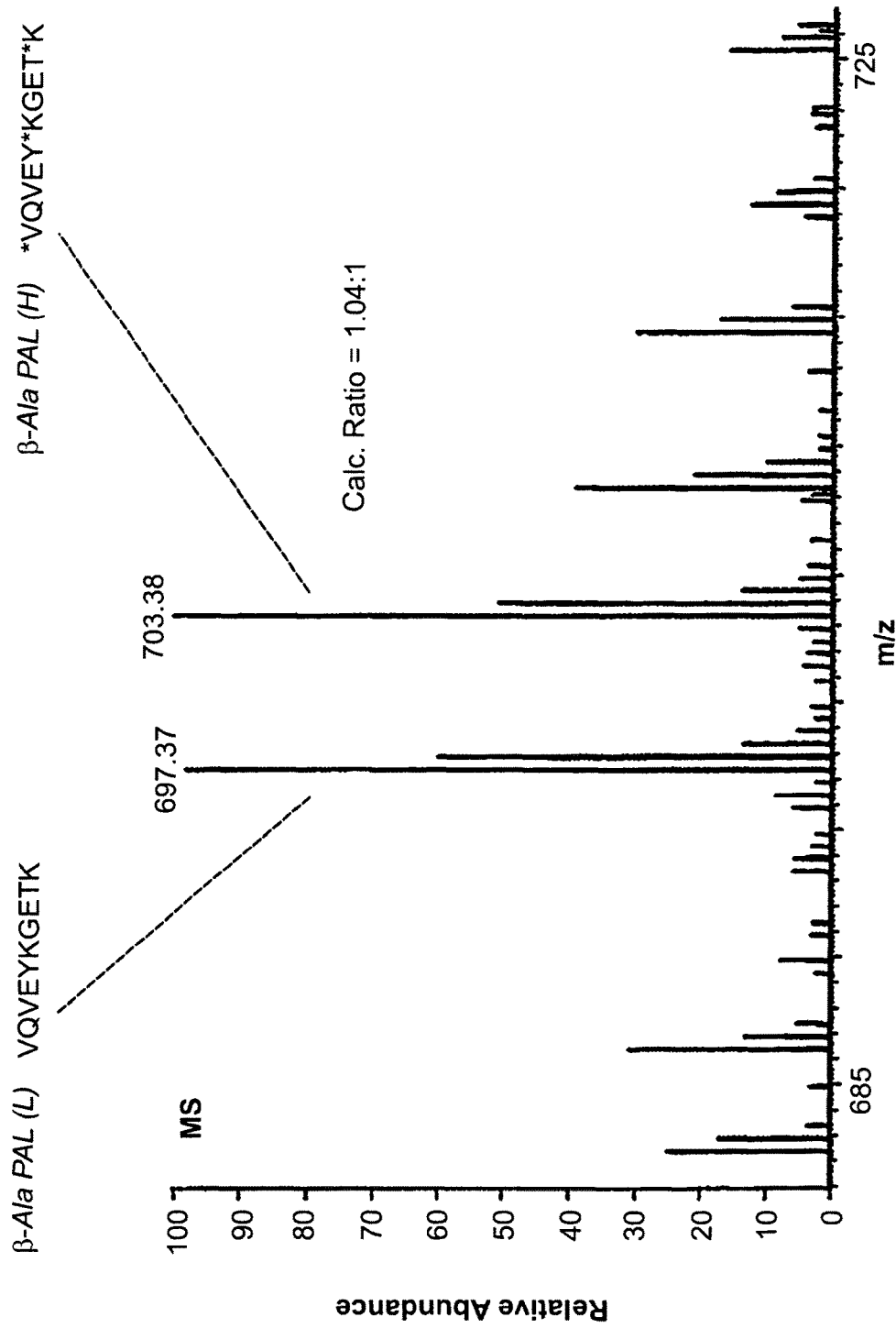
FIG. 9. Quantitative analysis of peptides derived from human, K562 whole cell lysates. (A) MS spectrum with the missed cleavage peptide, VQVEYKGETK, detected with an abundance ratio of 1.04:1. (B) MS/MS spectrum contains expected N- and C-terminal fragment ions, depicted as $b_n$ and $y_n$, respectively, and is readily identified by Mascot.
Figure 9B:
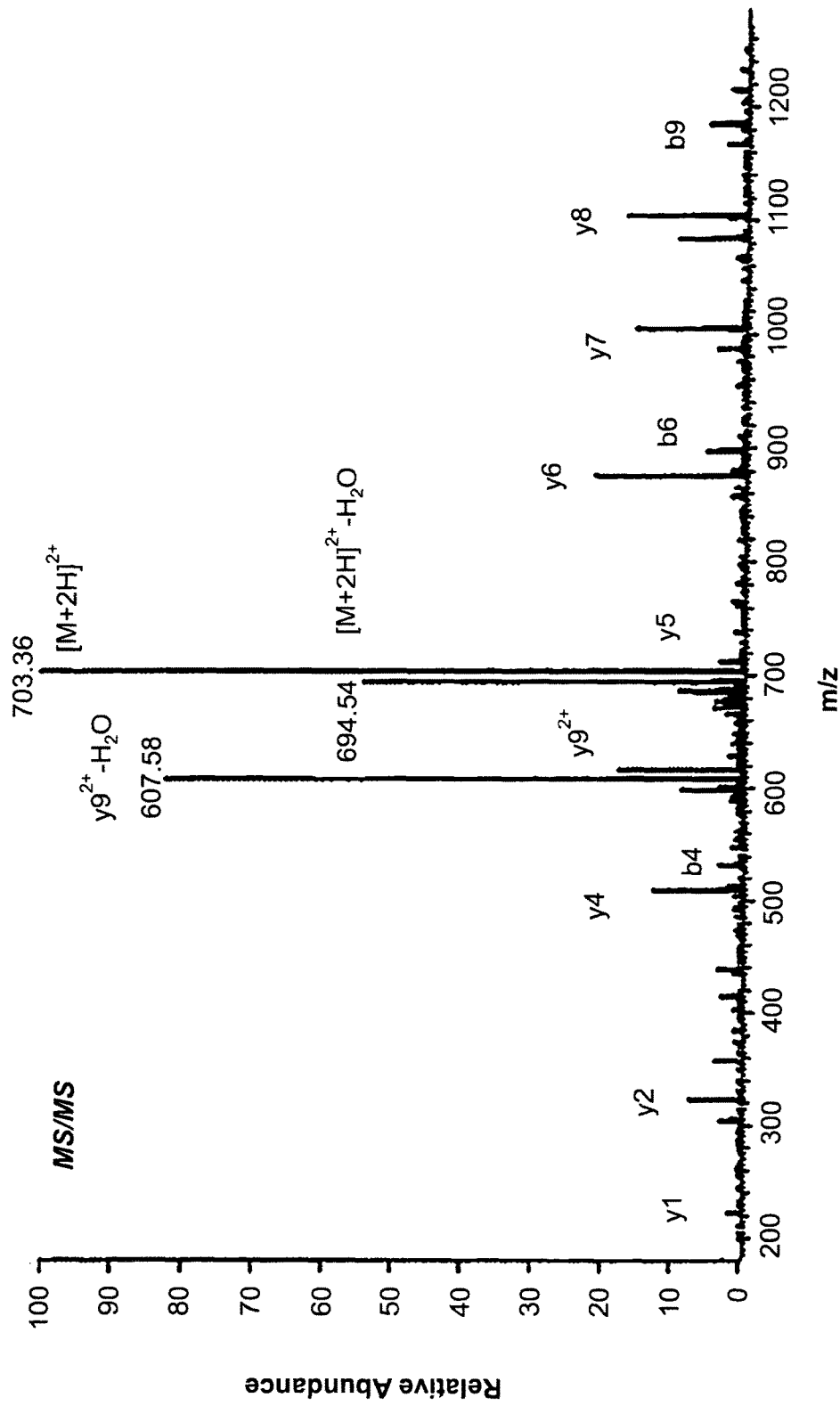

The next step was to determine whether the labels would perform well for quantification of protein mixtures. As a first step two solutions were prepared, each containing four standard proteins (bovine serum albumin, beta galactosidase, ovalbumin, and beta lactoglobulin) in ratios listed in FIG. 27 (Table 1). Each mixture was processed as in FIG. 2, with the light and heavy β-Ala PAL peptide mixture analyzed by LC-MS/MS. Interrogation of RIC peak areas for identified peptides yielded protein ratios that agreed to within 20% of the actual values, with CVs of <20% for individual peptide measurements (FIG. 27; Table 1). Next, proteins from human K562 myeloid cells were solubilized, divided into two equal aliquots, and processed as in FIG. 2. The resulting tryptic peptides were labeled with light and heavy forms of R-Ala PAL, mixed, and analyzed by LC-MS/MS. 545 unique peptide sequences were identified (Mascot Score ≥20) with an average abundance ratio of 1.15:1, with only 11 unlabeled peptides observed in this analysis. FIG. 9A shows labeled forms of the peptide, VQVEYKGETK, detected at an abundance ratio of 1.04:1. Although this peptide contains an internal lysine due to a missed cleavage by trypsin, the MS/MS spectrum (FIG. 9B) was readily assigned to the correct sequence by Mascot. These data demonstrate that PAL chemistry supports quantitative analysis of peptides derived from complex, whole cell lysates, typically encountered in modern proteomics and biomedical research studies.

Figure 10:
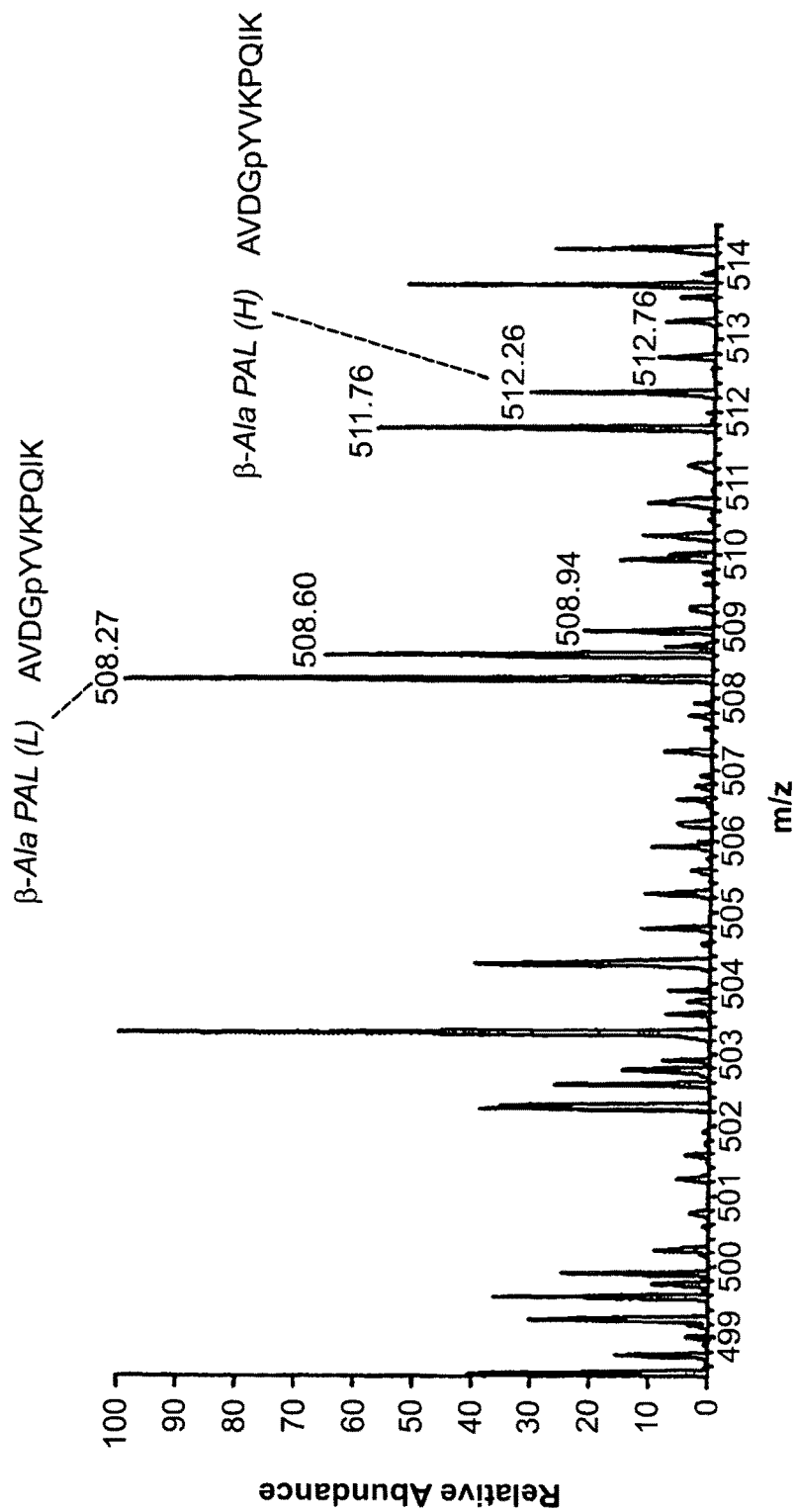
FIG. 10. Quantitative analysis of phosphopeptides derived from human, K562 cells treated with SKI-606, a dual inhibitor of SRC and ABL kinases. Peptides derived from control and treated cell cultures were labeled with light and heavy β-Ala PAL reagents. The phosphopeptide (AVDGpYVKPQIK) from STAT 5B, a known downstream target of SRC family kinases, was detected with an abundance ratio of ~10:1 (control:SKI-treated). NOTE: abundant isotope cluster at m/z 511.76, 512.26, 512.76, overlaps with the expected signal for the heavy version of the peptide of interest.
Figure 11:
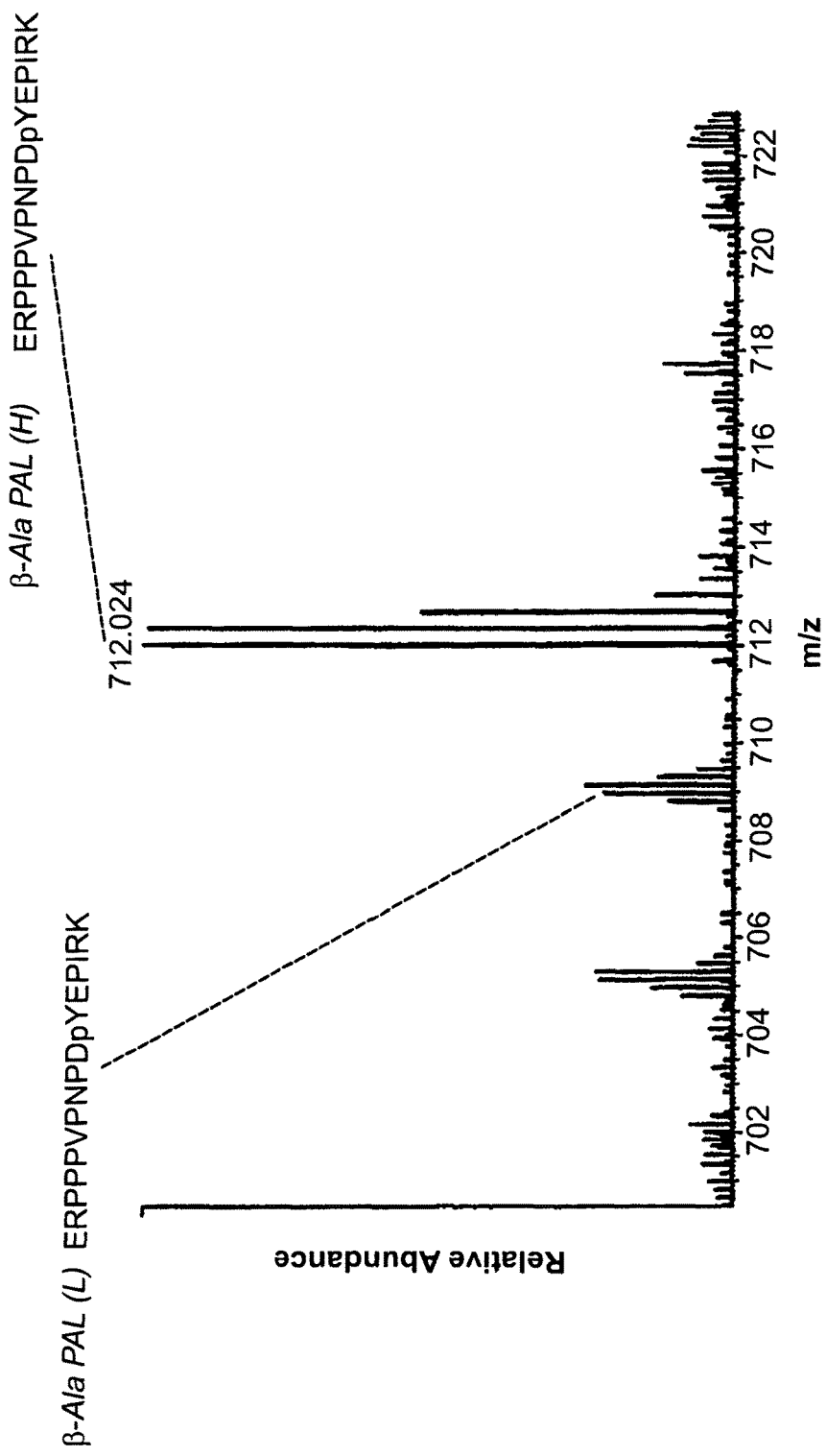
FIG. 11. Quantitative analysis of phosphopeptides derived from human Jukat cells treated with pervanadate, a known activator of T-cell signaling. Peptides derived from control and treated cell cultures were labeled with light and heavy β-Ala PAL reagents. The phosphopeptide (ERPPPVPNPD-pYEPIRK) from the transmembrane receptor, CD3ε was detected with an abundance ratio of >50:1 (pervanadate-treated:control or heavy:light), consistent with known mechanisms associated with T-cell signaling. NOTE: abundant isotope cluster at m/z~709 overlaps with the expected signal for the light version of the peptide of interest.
Figure 13A:
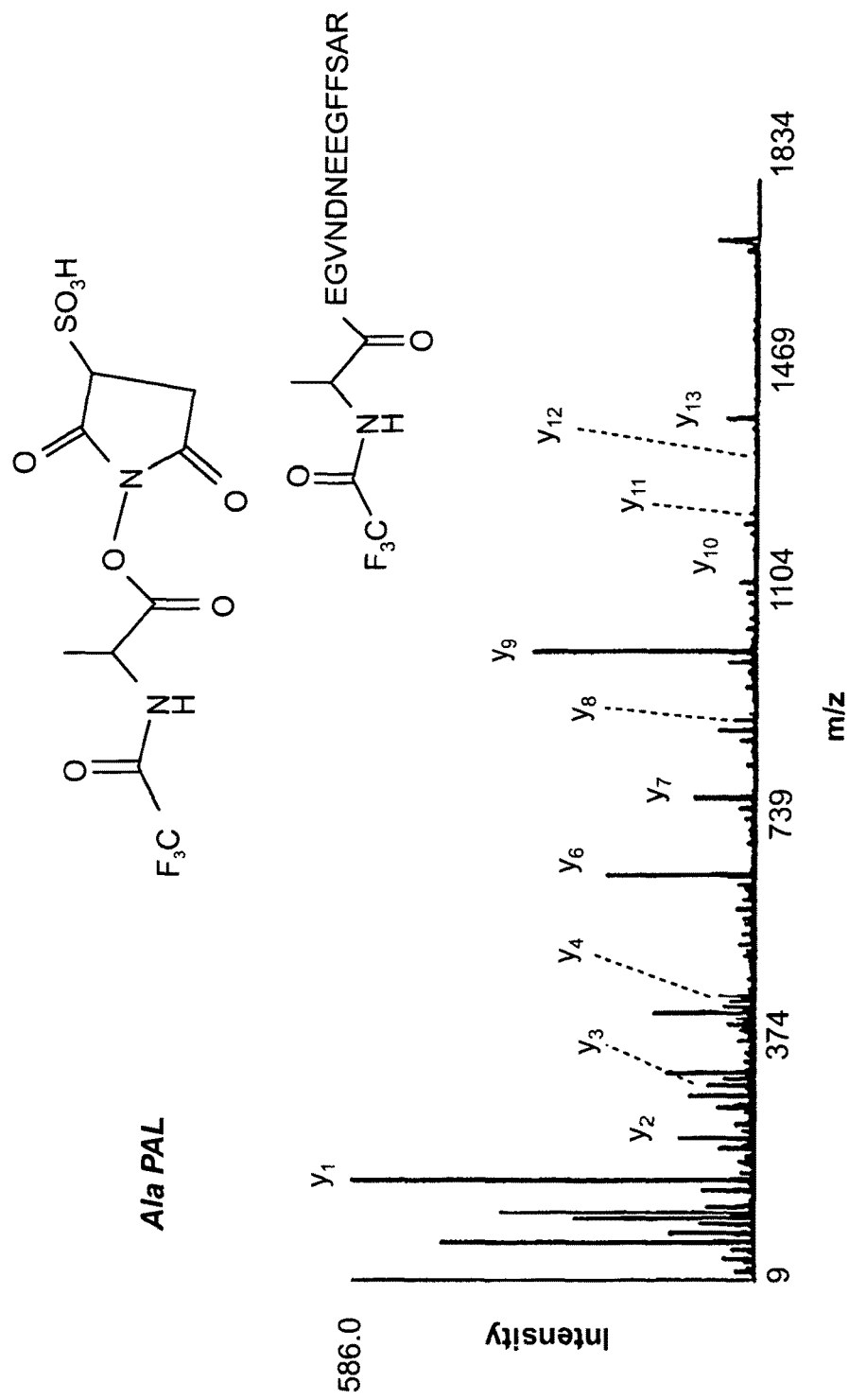
FIG. 13. MALDI MS/MS spectra of Ala PAL labeled Glu-Fib peptide (EGVNDNEEGFFSAR) in (A) protected and (B) deprotected forms. Fragments containing the peptide N- and C-terminus are indicated as $b_n$ and $y_n$, respectively.
Figure 13B:
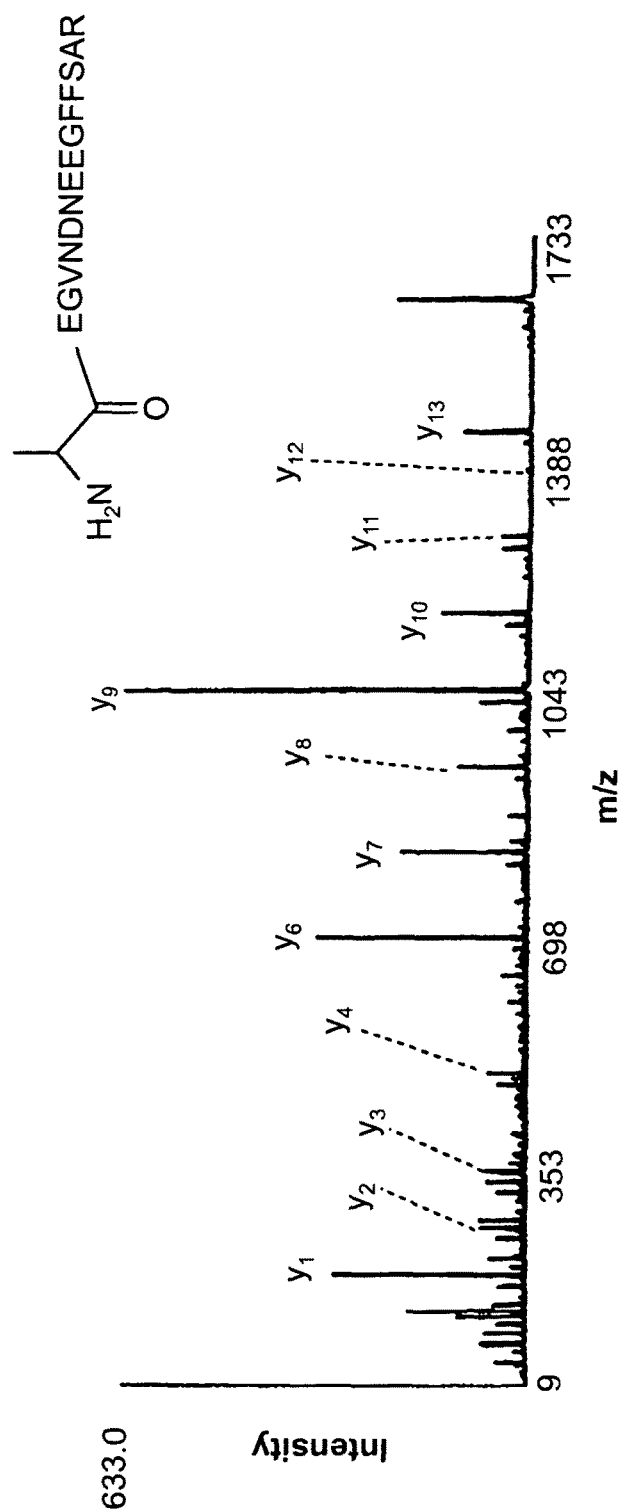
Figure 14A:
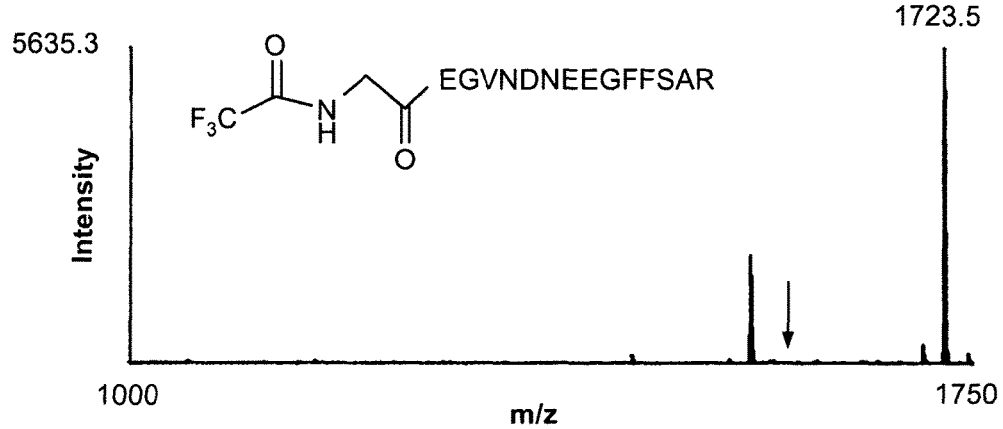
FIG. 14. MALDI MS spectra of the peptide Glu-Fib (EGVNDNEEGFFSAR) labeled with the light form of Gly PAL, before (A) and after (B) deprotection. Vertical arrow indicates m/z value for unlabeled peptide.
Figure 14B:
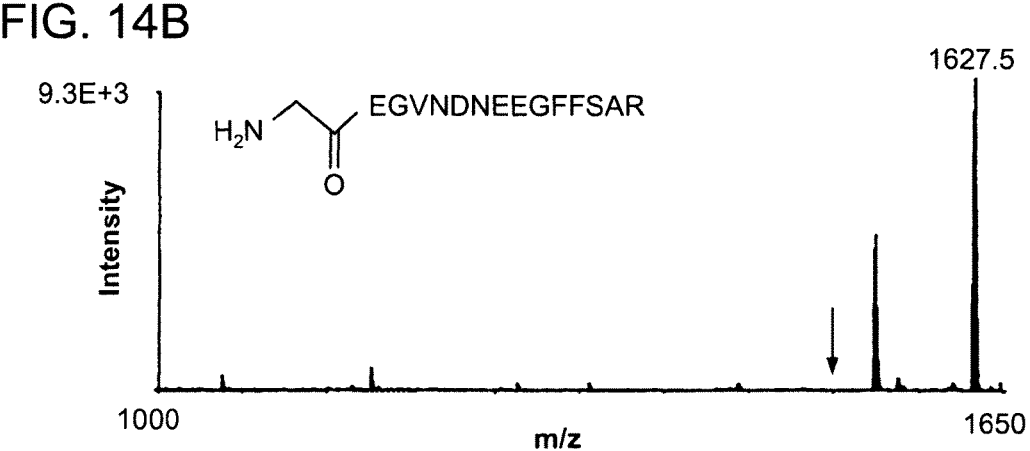
Figure 15A:
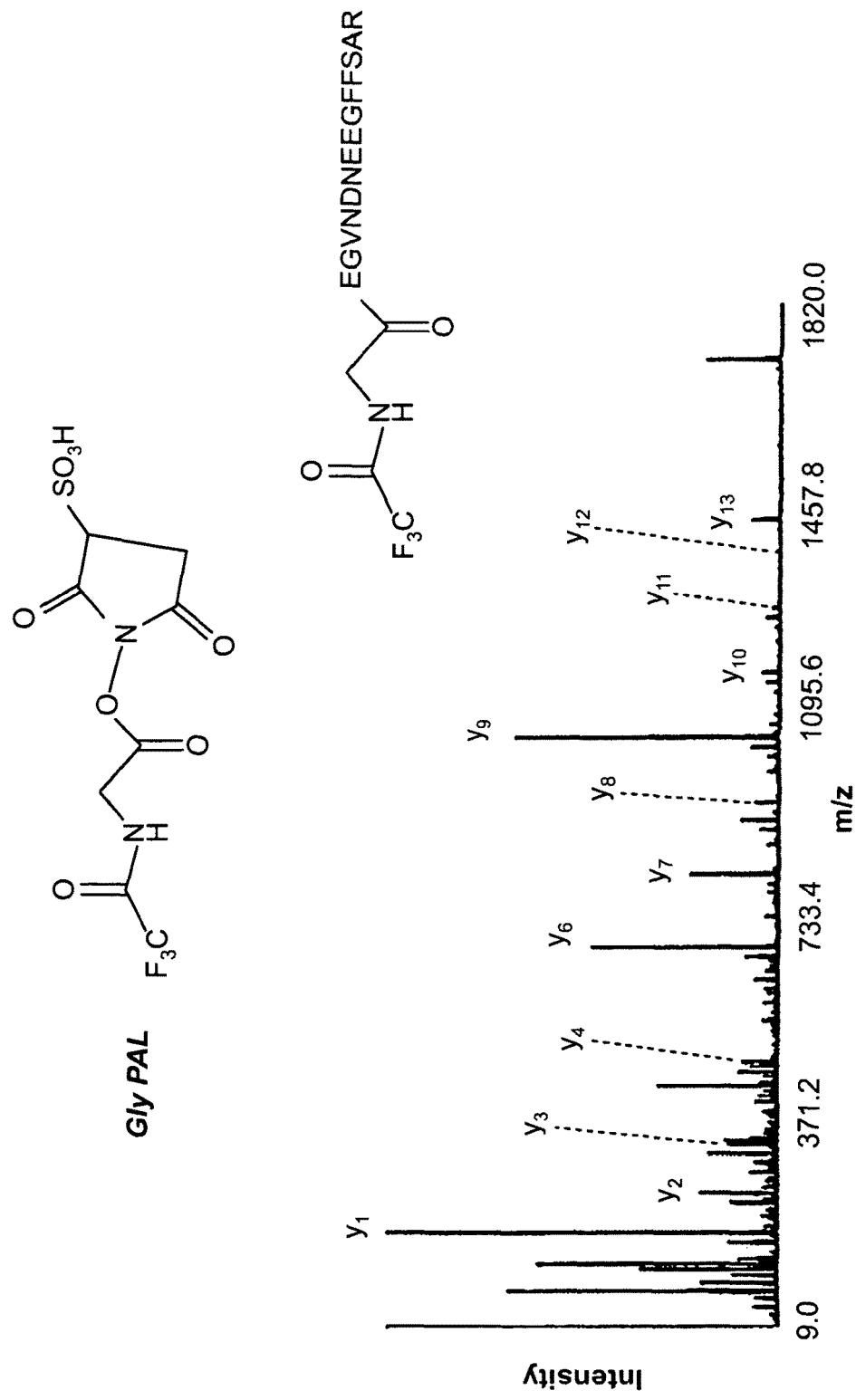
FIG. 15. MALDI MS/MS spectra of Gly PAL labeled Glu-Fib peptide (EGVNDNEEGFFSAR) in (A) protected and (B) deprotected forms. Fragments containing the peptide N- and C-terminus are indicated as $b_n$ and $y_n$, respectively.
Figure 15B:
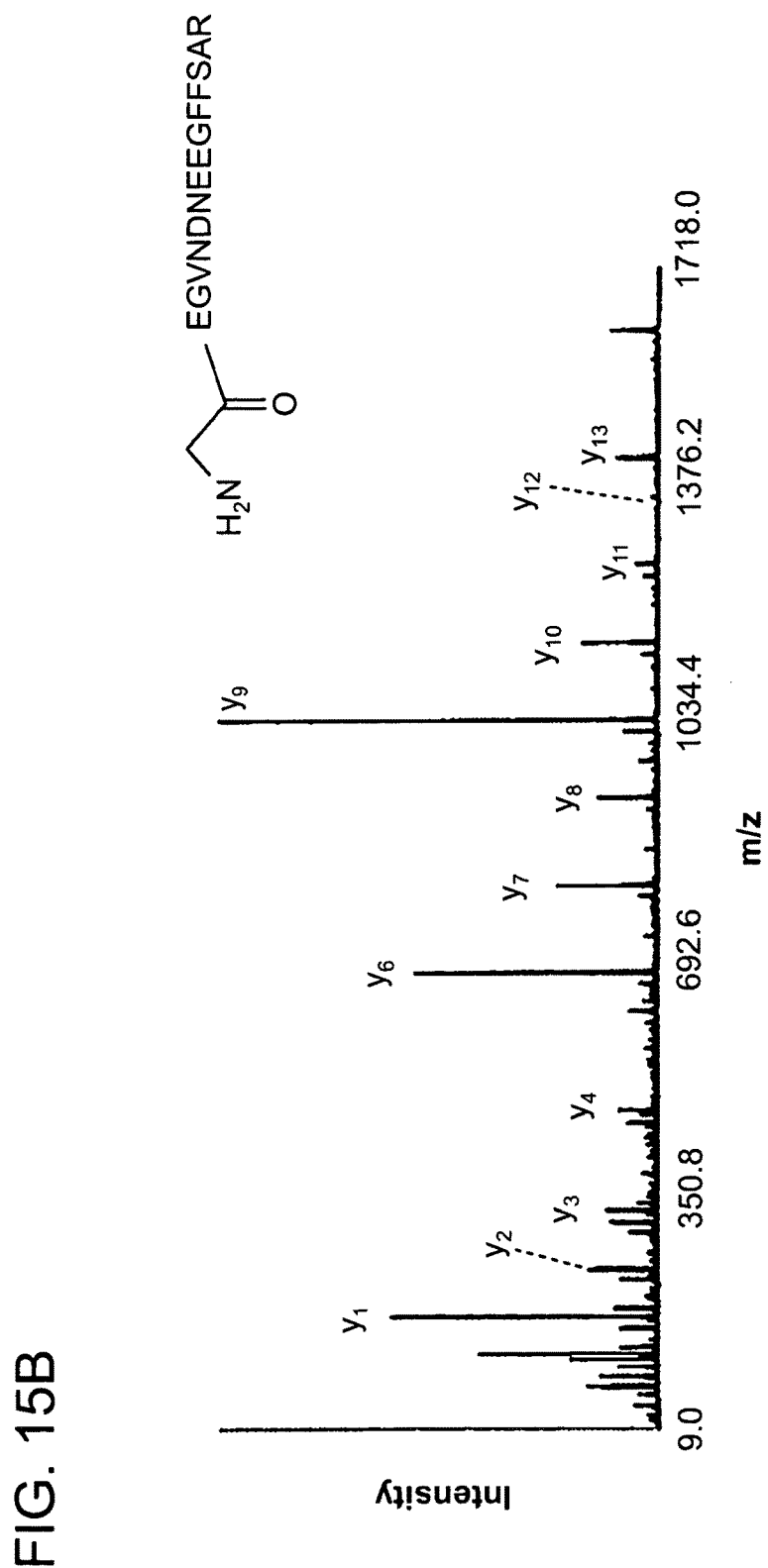

PAL chemistry in the context of quantitative phosphoproteomics analyses was also tested. For example, human K562 cells were cultured in the presence of SKI-606, a small molecule dual inhibitor of SRC and Abl kinases. Proteins purified from these cells were processed as in FIG. 2, in parallel with proteins from control (e.g., treated with DMSO) cells. After equal aliquots of heavy and light β-Ala PAL peptides were combined and desalted (FIG. 2, bottom), phosphopeptides on a NTA-Fe IMAC column were cultured. FIG. 10 shows labeled forms of the peptide, AVDGpYVK-PQIK, detected at an abundance ratio of 10:1 (control:SKI-treated). This peptide was derived from the protein STAT 5B, a known downstream signaling target of SRC family kinases. As a second example, human Jurkat cells were cultured in the presence of pervanadate, a general activator of T-cell signaling. Heavy and light β-Ala PAL peptides were processed as described above (FIG. 2) and then subjected to phosphopeptide enrichment, and LC-MS/MS analysis. FIG. 11 shows MS data for the peptide ERPPPVP-NPDpYEPIRK, derived from the transmembrane receptor, CD3ε. A ratio of >50:1 (pervanadate-treated:control) was observed, consistent with known mechanisms associated with T-cell signaling. Collectively these data demonstrate that PAL chemistry is amenable to proteomics experiments designed to elucidate large scale signaling networks, a burgeoning field of study in biomedical research.

Protected Amine Labels: Other Duplex Reagents

Figure 16A:
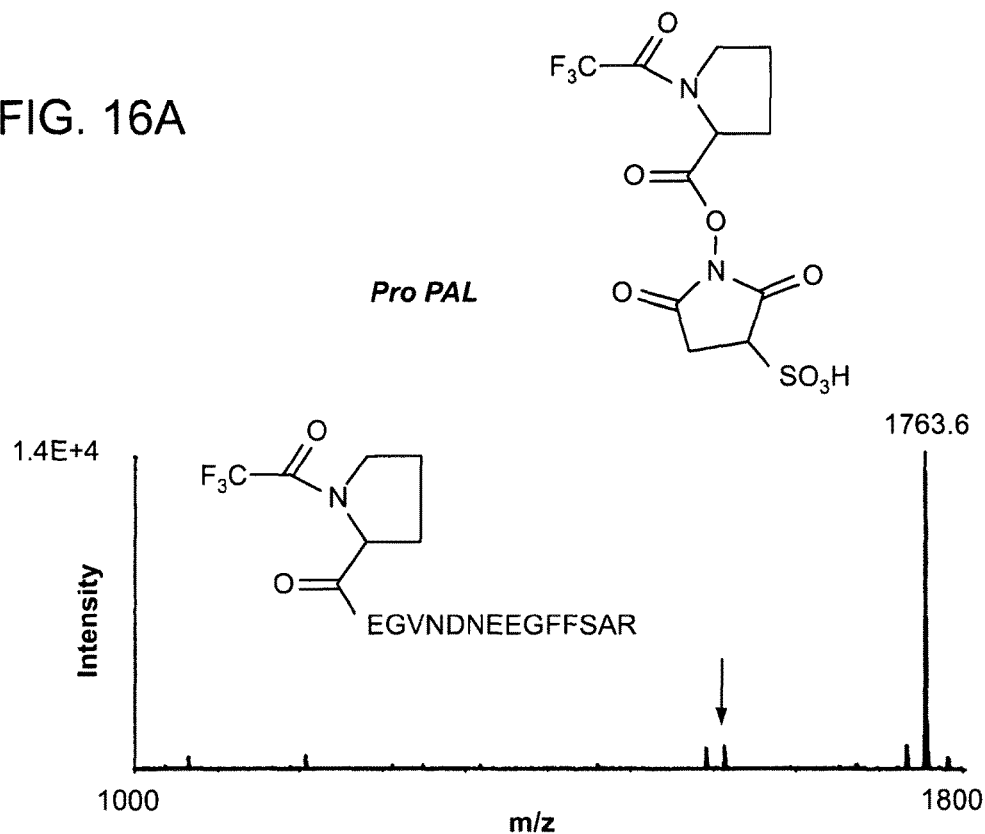
FIG. 16. MALDI MS spectra of the peptide Glu-Fib (EGVNDNEEGFFSAR) labeled with the light form of Pro PAL, before (A) and after (B) deprotection. Vertical arrow indicates m/z value for unlabeled peptide.
Figure 16B:
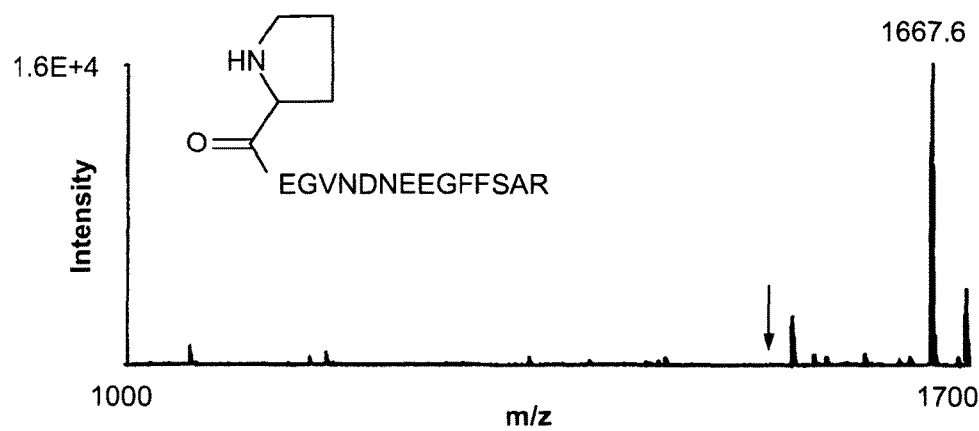
Figure 17A:
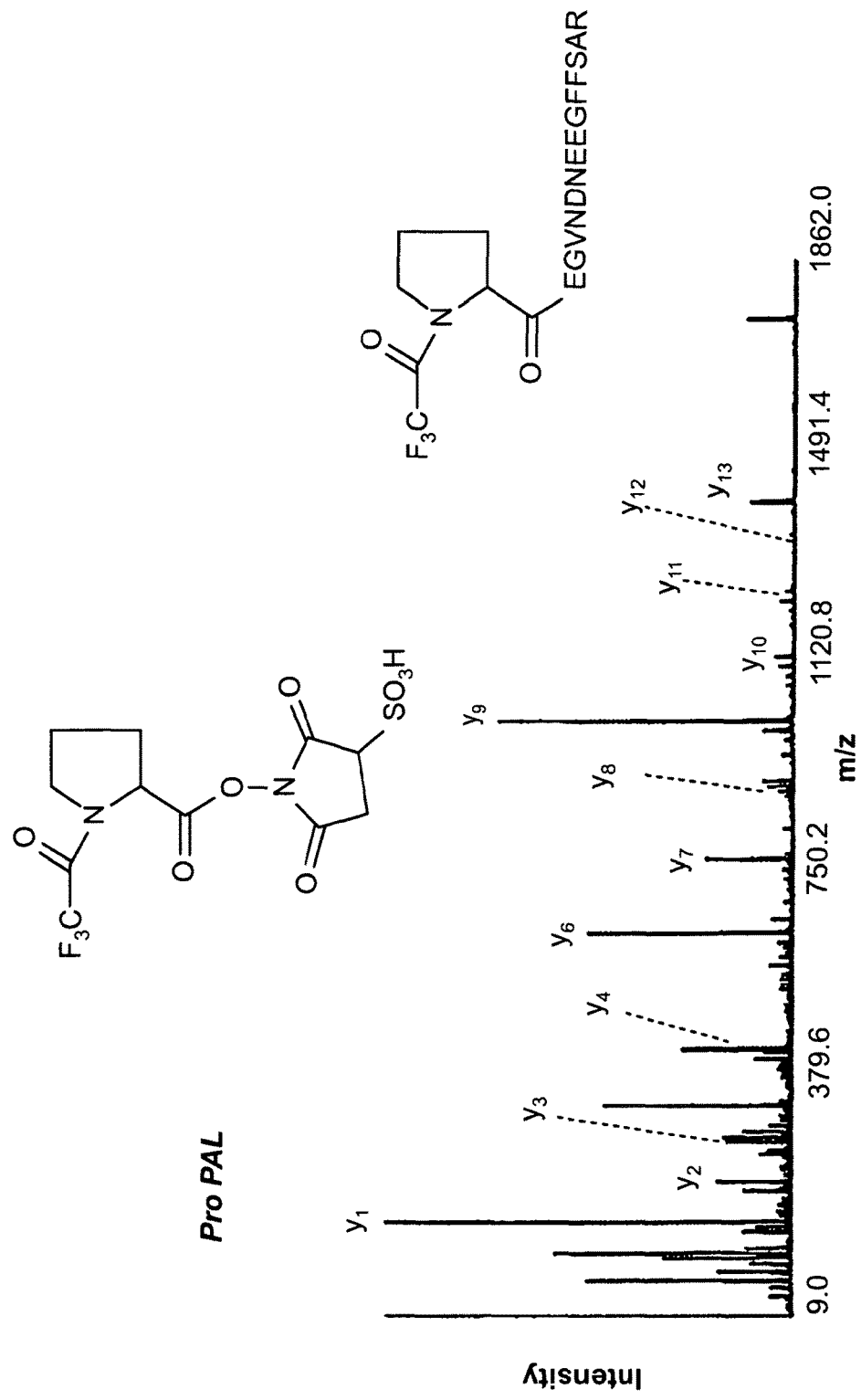
FIG. 17. MALDI MS/MS spectra of Pro PAL labeled Glu-Fib peptide (EGVNDNEEGFFSAR) in (A) protected and (B) deprotected forms. Fragments containing the peptide N- and C-terminus are indicated as $b_n$ and $y_n$, respectively.
Figure 17B:
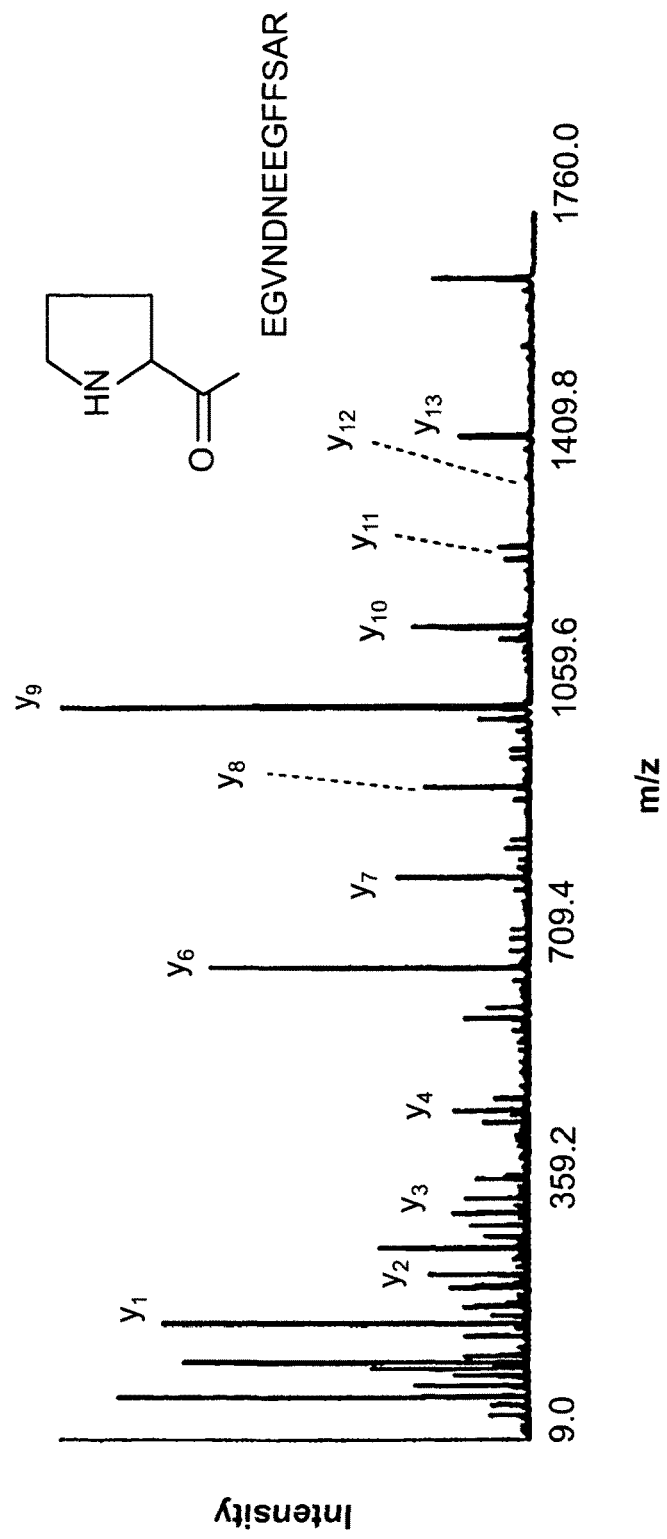
Figure 18:
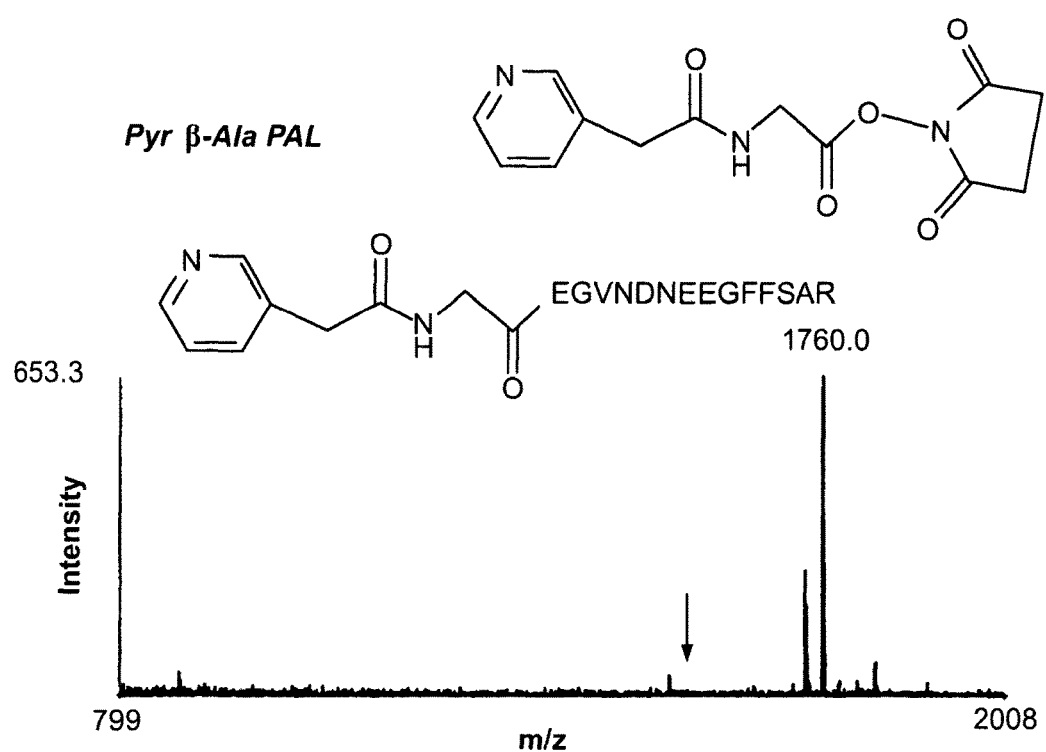
FIG. 18. MALDI MS spectra of the peptide Glu-Fib (EGVNDNEEGFFSAR) labeled with the light form of Pyrβ-Ala PAL. Vertical arrow indicates m/z value for unlabeled peptide.
Figure 19:
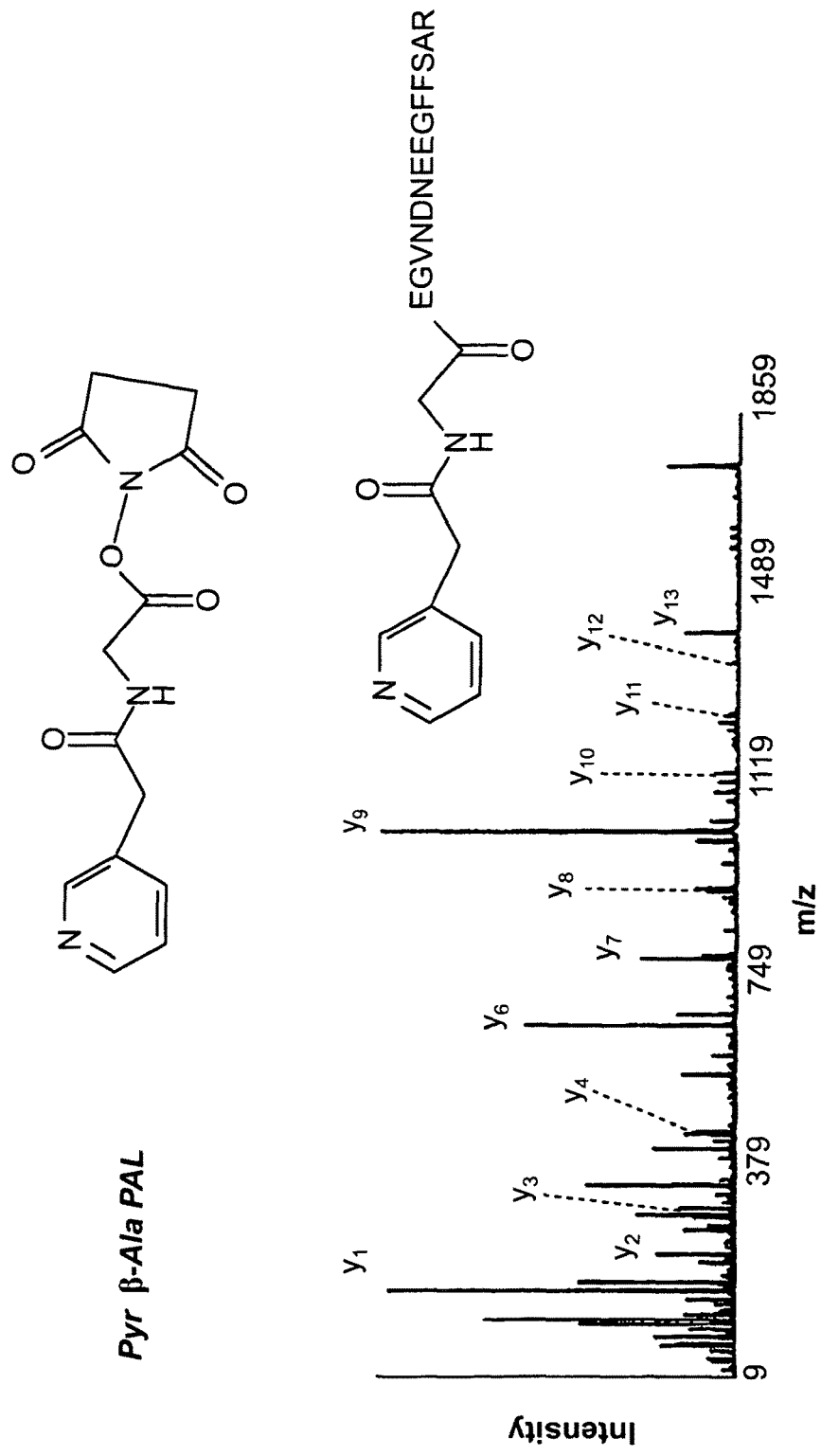
FIG. 19. MALDI MS/MS spectra of Pyrβ-Ala PAL labeled Glu-Fib peptide (EGVNDNEEGFFSAR). Fragments containing the peptide N- and C-terminus are indicated as $b_n$ and $y_n$, respectively.

As a proof-of-principle of the general applicability of PAL chemistry, light forms of several other compounds based on FIG. 1 were generated. For example, FIGS. 12-17 show MS and MS/MS spectra for the peptide Glu-Fib (EGVND-NEEGFFSAR) labeled with light forms of Ala PAL (FIGS. 12 and 13), Gly PAL (FIGS. 14 and 15), and Pro PAL (FIGS. 16 and 17). In each case the tri-fluoroacetate protecting group was removed by incubation of the labeled peptide at pH~12 for 60 min. As with β-Ala PAL, no adverse effect on fragmentation were observed via standard, low-energy MS/MS analysis, nor was any evidence of deamidation at asparagine residues as a result of the deprotection step detected. β-Ala PAL with a pyridyl acetate group irreversibly linked at the amino acid N-terminus (Pyr β-Ala PAL) was synthesized. This approach obviates the need to regenerate a free amino terminus and provides additional flexibility with respect to incorporation of stable isotopes within the pyridyl ring. As with other embodiments of PAL chemistry, quantitative labeling (FIG. 18) and high sequence coverage in low-energy MS/MS fragment ion spectra (FIG. 19) was observed.

Protected Amine Labels: β-alanine Multiplex Reagent (β-Ala PAL MP).

Figure 20A:
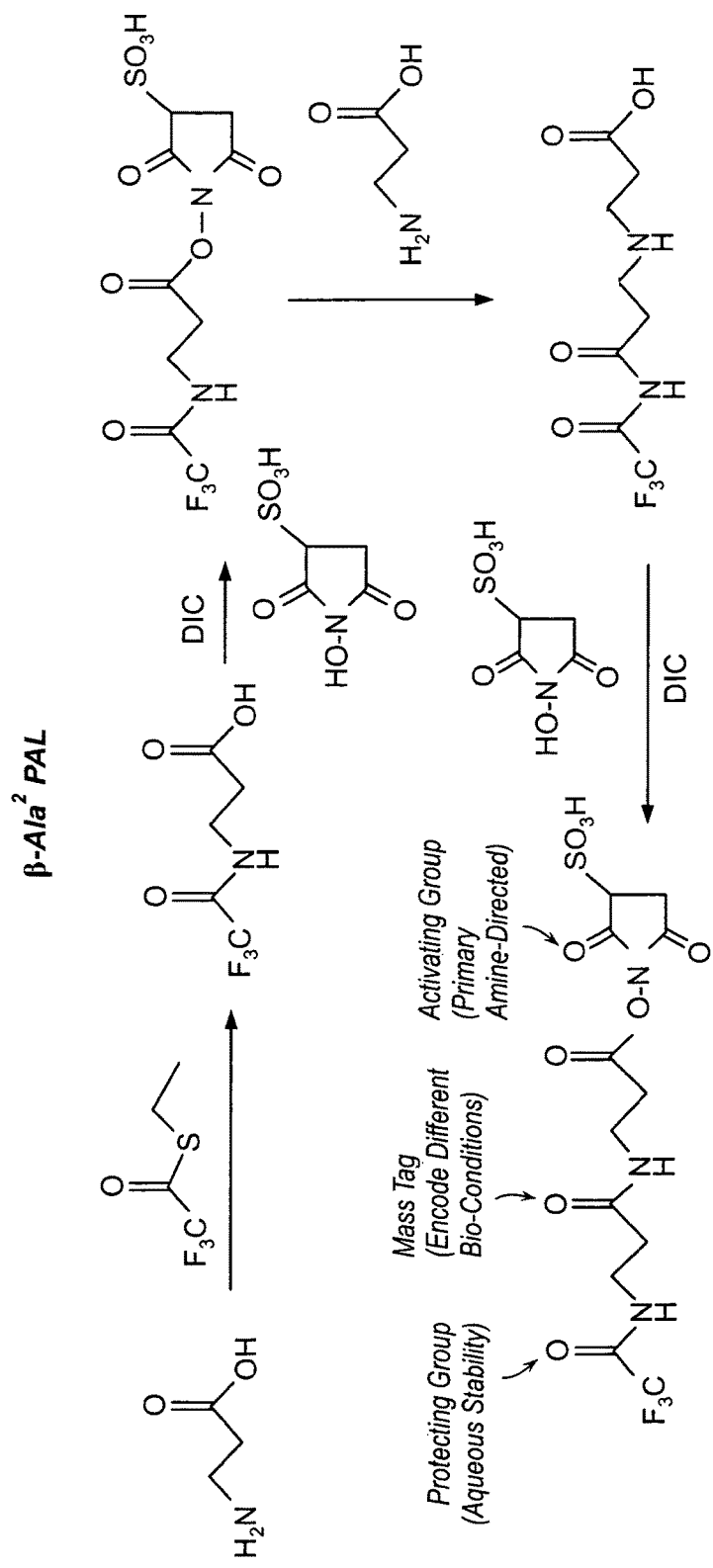
FIG. 20. (A) Synthetic scheme for β-Ala$^2$ PAL triplex reagents. (B) Experimental workflow. Proteins are isolated from gel bands, cultured cells, primary tissues, or animal models, digested with trypsin, and the resulting peptides are labeled with light-light, light-heavy and heavy-heavy versions of β-Ala$^2$ PAL. Primary amines are regenerated prior to LC-MS/MS by incubation at pH~11.5 for 30 min. Abundance ratios for peptide precursors that are separated by a mass-to-charge (m/z) value equal to (n×4)/z, where n is the number of peptide primary amine groups and z is the peptide charge state, provide relative quantification for peptides in each biological condition.
Figure 20B:
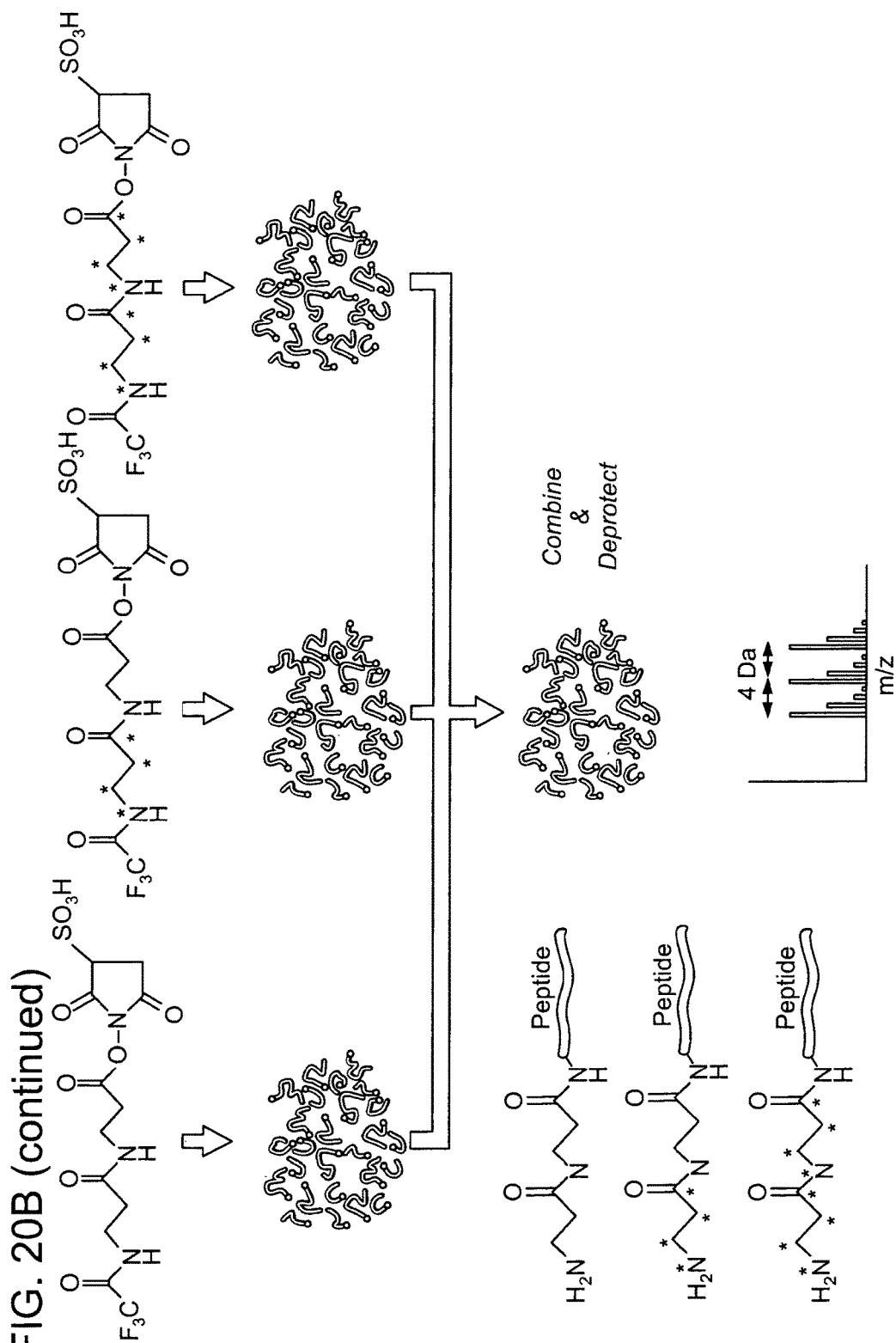
Figure 21A:
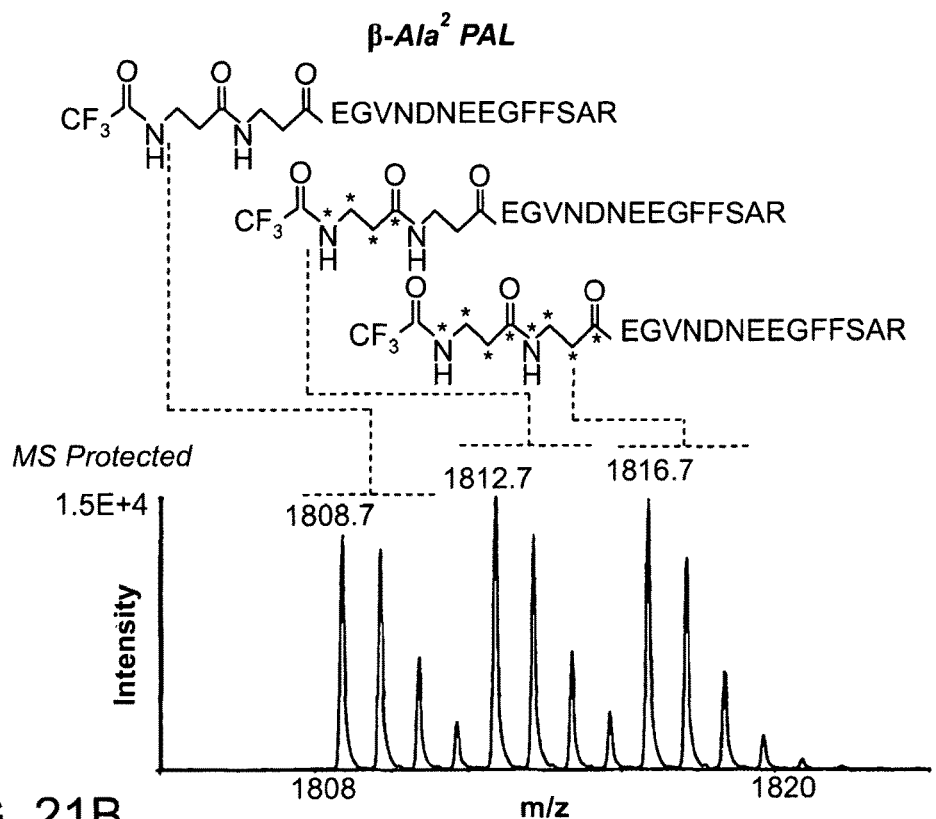
FIG. 21. MALDI MS spectra of the peptide Glu-Fib (EGVNDNEEGFFSAR) labeled in a 1:1:1 ratio with light-light, light-heavy and heavy-heavy β-Ala$^2$ PAL, before (A) and after (B) deprotection.
Figure 21B:
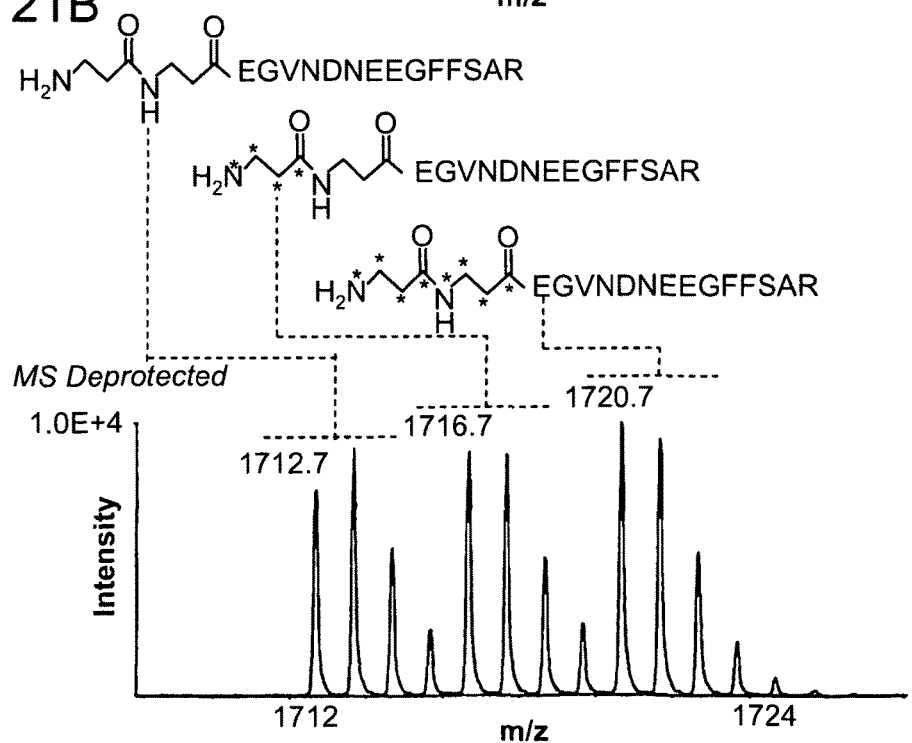
Figure 22C:
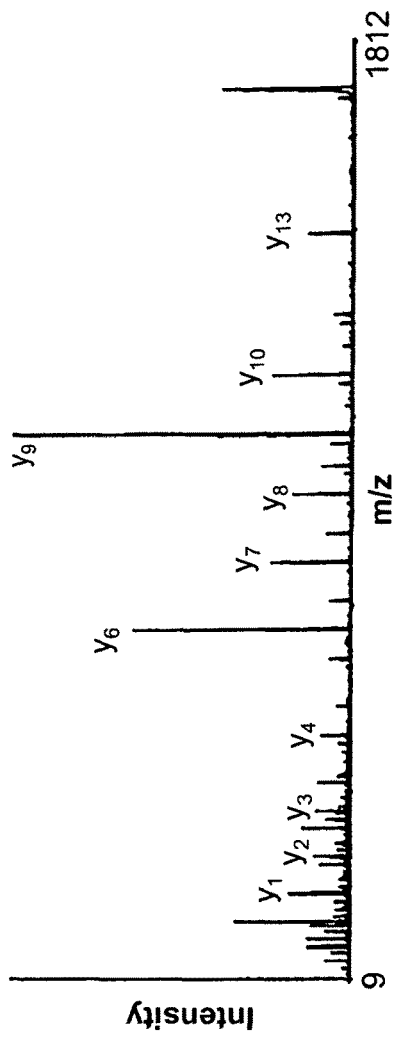
FIG. 22. MALDI MS/MS spectra of Glu-Fib peptide (EGVNDNEEGFFSAR) in (A) native and β-Ala$^2$ PAL labeled (B, C, and D) forms. PAL chemistry does not significantly alter distribution of fragment ions. Fragments containing the peptide N- and C-terminus are indicated as $b_n$ and $y_n$, respectively.
Figure 22D:
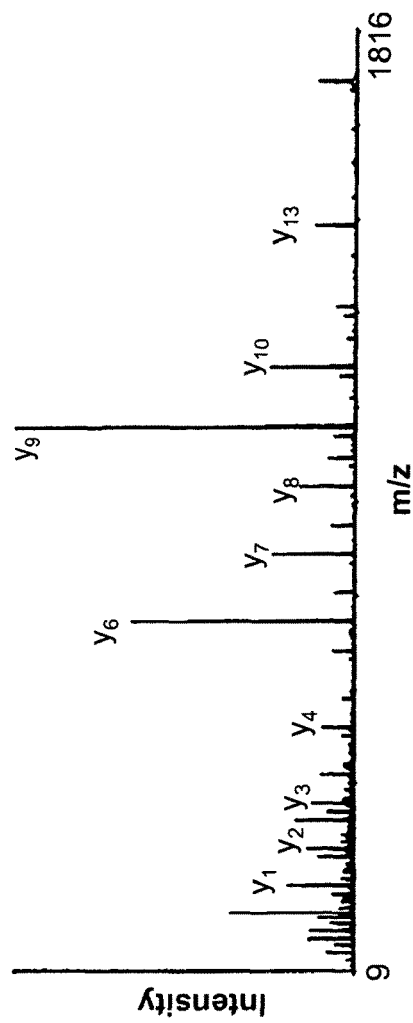
Figure 23A:
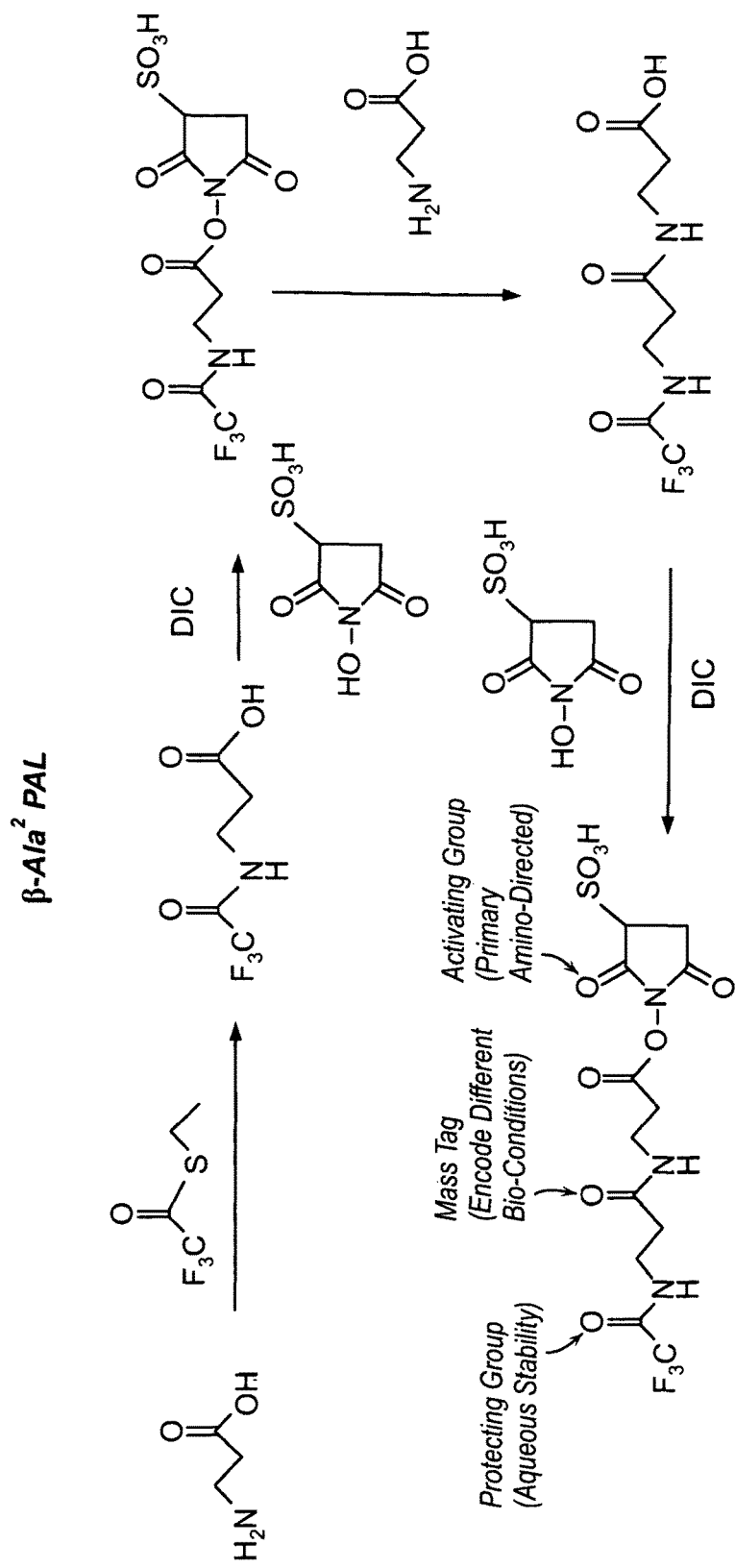
FIG. 23. (A) Synthetic scheme for β-Ala$^2$ PAL 4-plex reagents. (B) Experimental workflow. Proteins are isolated from gel bands, cultured cells, primary tissues, or animal models, digested with trypsin, and then peptides from each sample are labeled with different isotopomers of β-Ala$^2$ PAL reagents. Primary amines are regenerated prior to LC-MS/MS by incubation at pH~11.5 for 30 min. Abundance ratios for peptide precursors that are separated by a mass-to-charge (m/z) value equal to (n×4)/z, where n is the number of peptide primary amine groups and z is the peptide charge state, provide relative quantification for peptides in each biological condition.
Figure 23B:
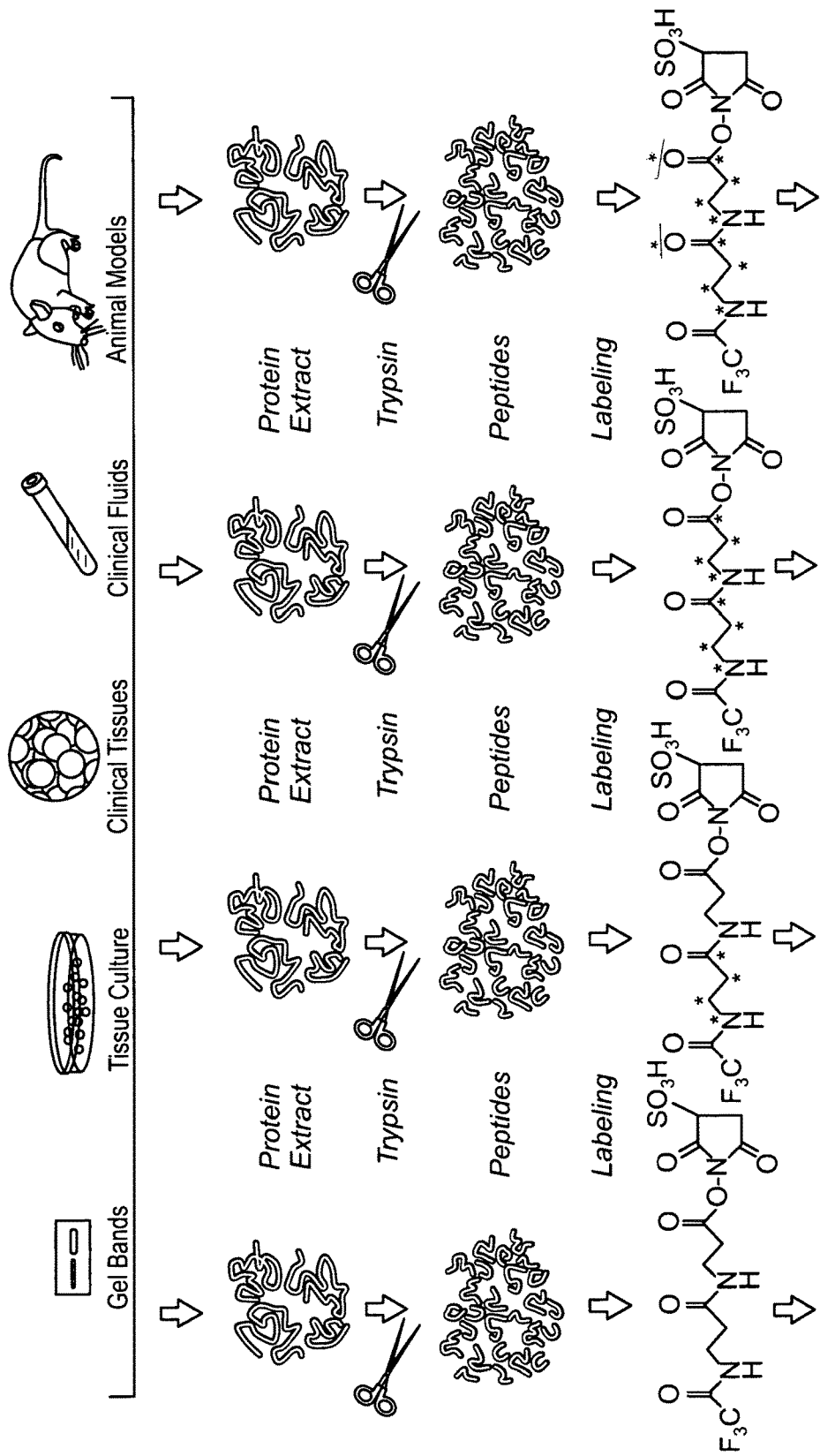
Figure 23B:
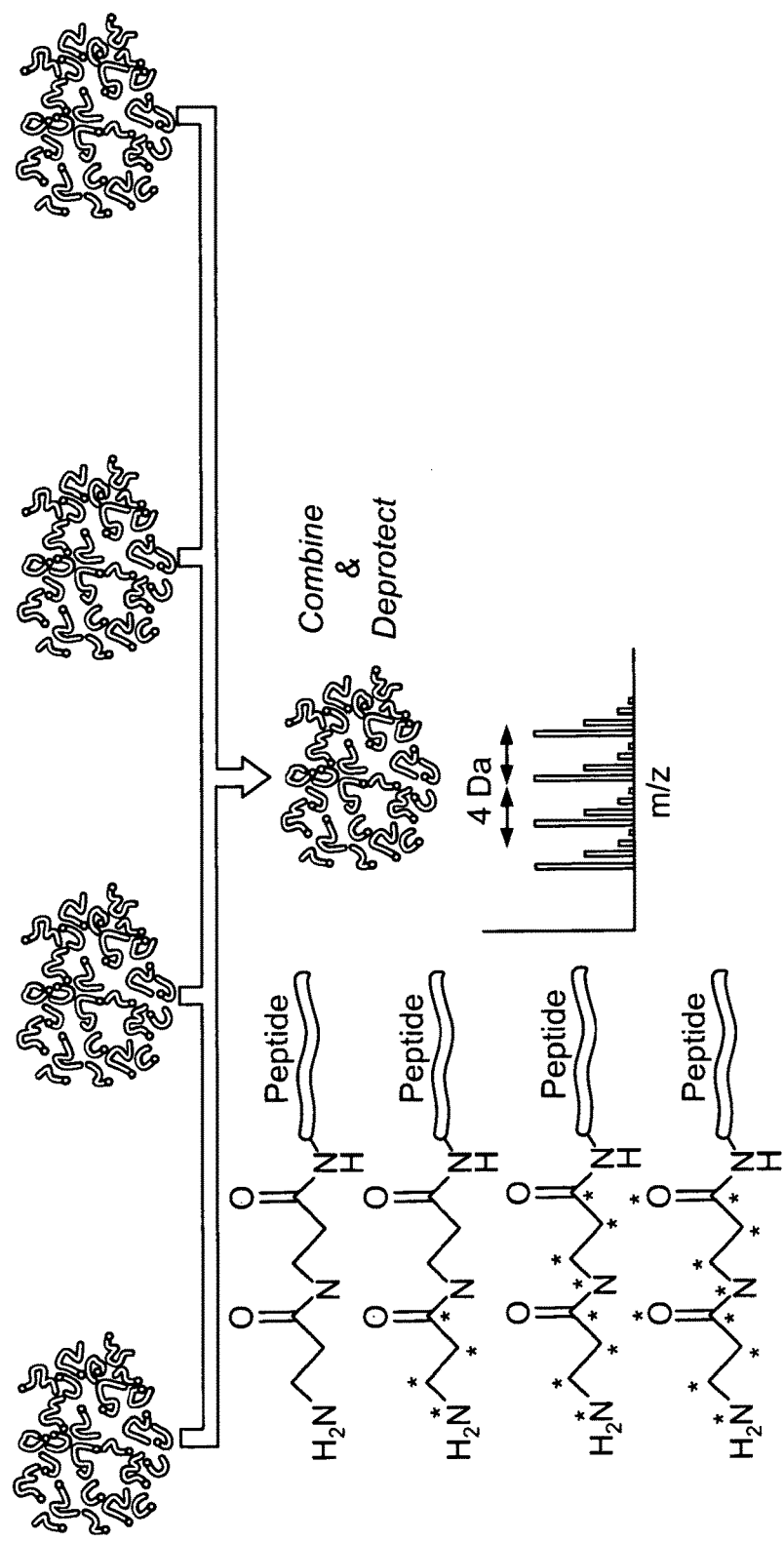

The reagents described above all function as duplex labels, that is, they enable comparison of two proteome states (response to different biological stimuli, or control versus treated conditions). However, it is often desirable to compare multiple biological conditions simultaneously. This experimental approach is particularly relevant for large-scale or so-called systems level studies in which genome-scale data are analyzed in the context of mathematical models or machine learning algorithms in order to predict biological response to perturbation. Currently iTRAQ, TMT, and SILAC commercial reagents can be used for varying degrees (3-plex up to 8-plex) of multiplexed analysis. To explore the potential of PAL reagents to support analysis of more than two samples simultaneously, a triplex PAL reagent (FIG. 20) was synthesized based on combinations of light, light-heavy, and heavy-heavy versions a β-alanine, again protected at the N-terminus with tri-fluoroacetate and activated with sulfo-N-hydroxysuccinimide. FIG. 21 shows the peptide standard, Glu-Fibrinogen (EGVNDNEEGFF-SAR), labeled in a 1:1:1 ratio with each isotopomer of β-Ala PAL MP, and detected in MS mode before deprotection at m/z 1808.7, 1812.7, and 1816.7, respectively. Regeneration of the N-terminal amine yielded isotope clusters detected at m/z 1712.7, 1716.7, and 1720.7, respectively. Other figures of merit such as derivatization efficiency, absence of side reactions, reagent stability, etc., were similar to those observed for the binary reagent (FIGS. 2-5). Similarly, FIG. 22 shows that MS/MS spectra of unlabeled (A) and labeled (B-D) forms are nearly super imposable, demonstrating that the β-alanine dimer does not negatively impact peptide fragmentation under low-energy MS/MS conditions. The carbonyl oxygen in β-alanine is in principle available as a site for addition of stable isotopes. For example, incorporation of $^{18}O$ at both carbonyl groups in the β-alanine dimer yields a forth channel with a mass 4 Da greater than the $^{13}C_6^{15}N_2$ molecule (FIG. 23). Moreover, this strategy provided high molecular efficiency in terms of the mass shift achieved per atom in the total scaffold. Synthesis of this 4-plex reagent is in progress. FIG. 28 (Table 2) provides a brief comparison of PAL with several commercially available labels for quantitative proteomics applications.

Protected Amine Labels: High Resolution Duplex Reagents (PAL HR)

Figure 24A:
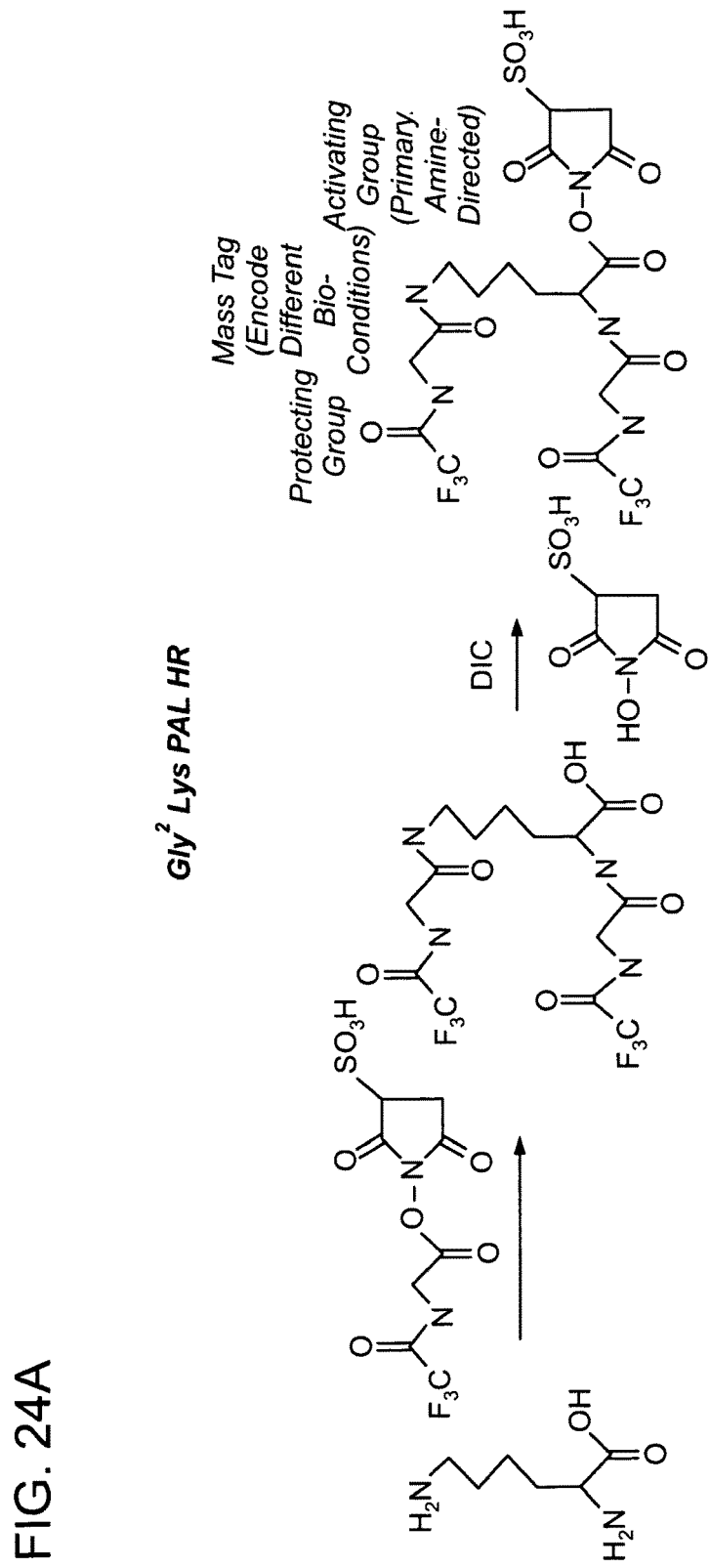
FIG. 24. (A) Synthetic scheme for Gly$^2$Lys PAL HR reagents. (B) Experimental workflow. Proteins are isolated from gel bands, cultured cells, primary tissues, or animal models, digested with trypsin, and the resulting peptides are labeled with light and heavy versions of Gly$^2$Lys PAL HR reagents. Primary amines are regenerated prior to LC-MS/MS by incubation at pH~11.5 for 30 min. Abundance ratios for peptide precursors that are separated by a mass-to-charge (m/z) value equal to (n×0.02534)/z, where n is the number of peptide primary amine groups and z is the peptide charge state, provide relative quantification for peptides in each biological condition.
Figure 24B:
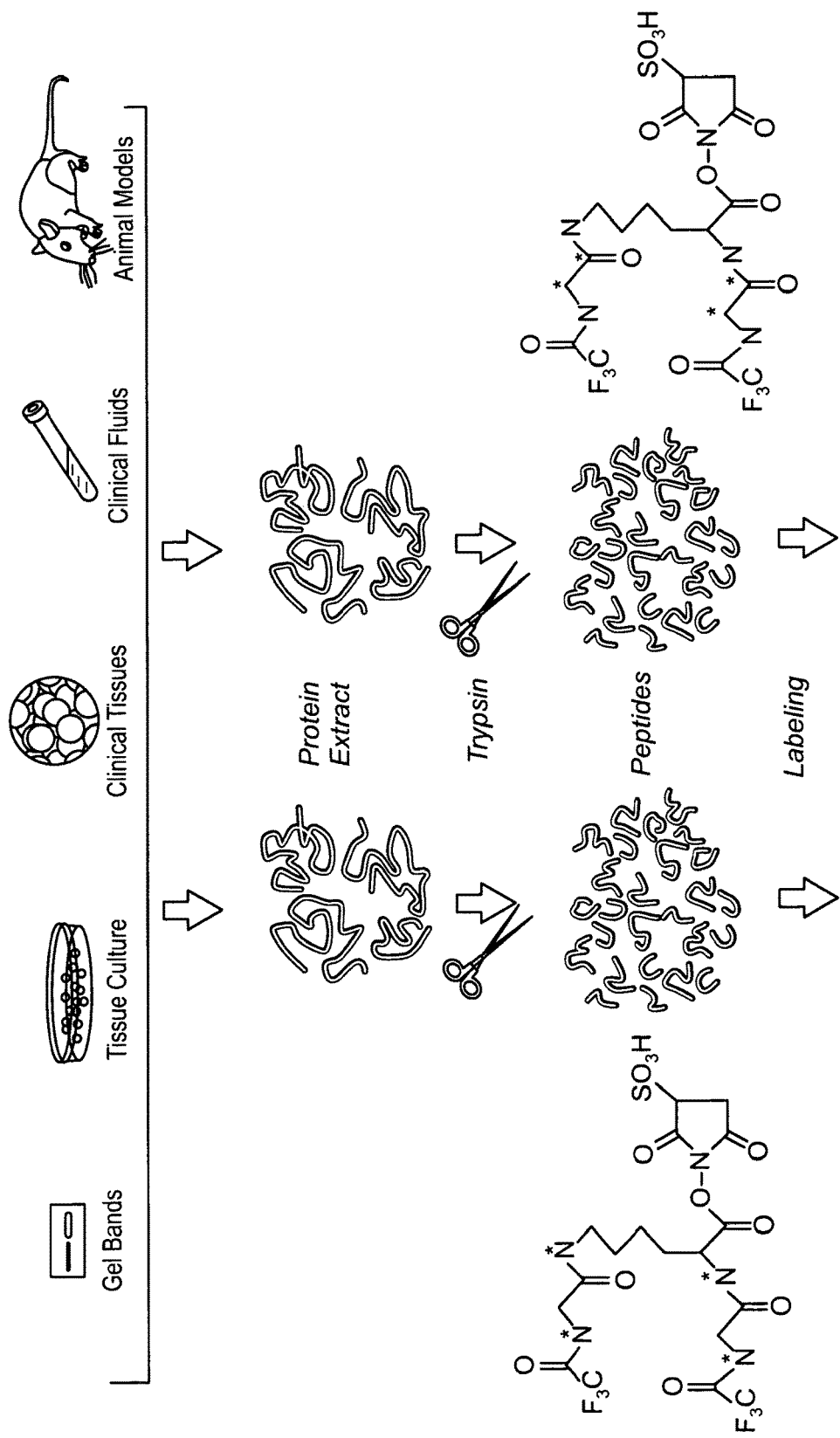
Figure 24B:
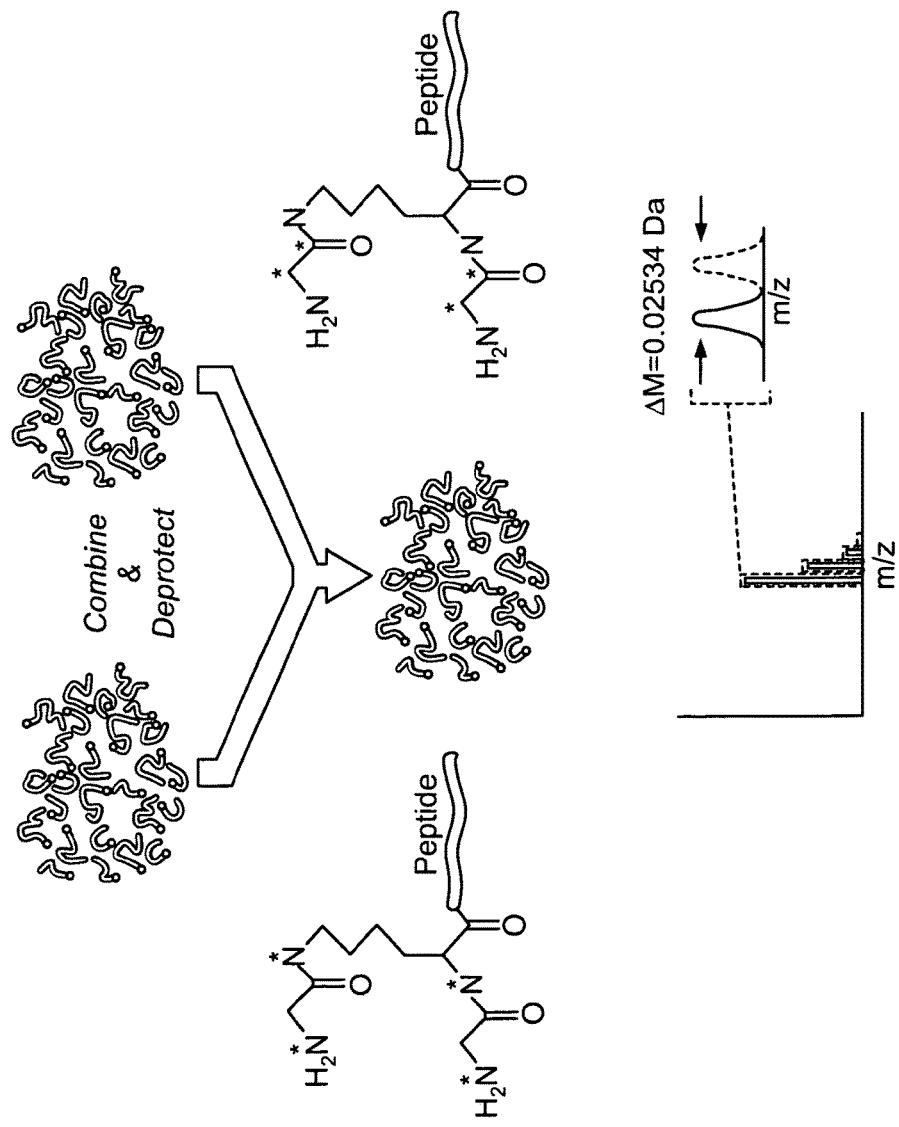
Figure 25A:
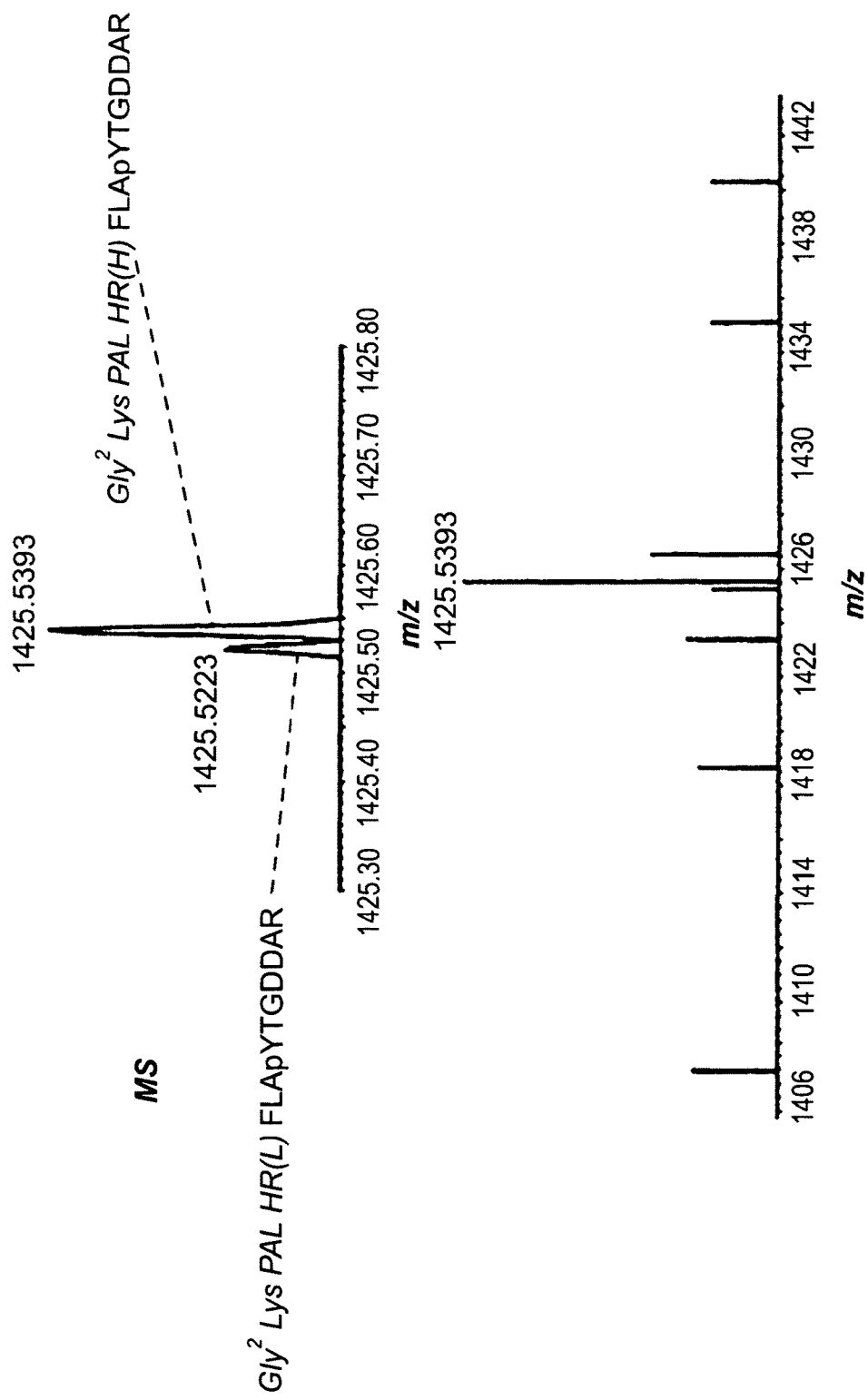
FIG. 25. Standard phosphopeptide (FLApYTGDDAR) labeled in a 1:2 ratio with Gly$^2$Lys PAL HR reagents. (A) MS scan near the singly-charged peptide at m/z ~1425; (inset) baseline resolution of the light and heavy peptide precursors, with an approximate abundance ratio of 1:2. (B) MS/MS spectrum contains N-terminal ($b_n$-type) fragment ions that exhibit light and heavy doublets, separated by 0.0253 Da, with a 1:2 abundance ratio.
Figure 25B:
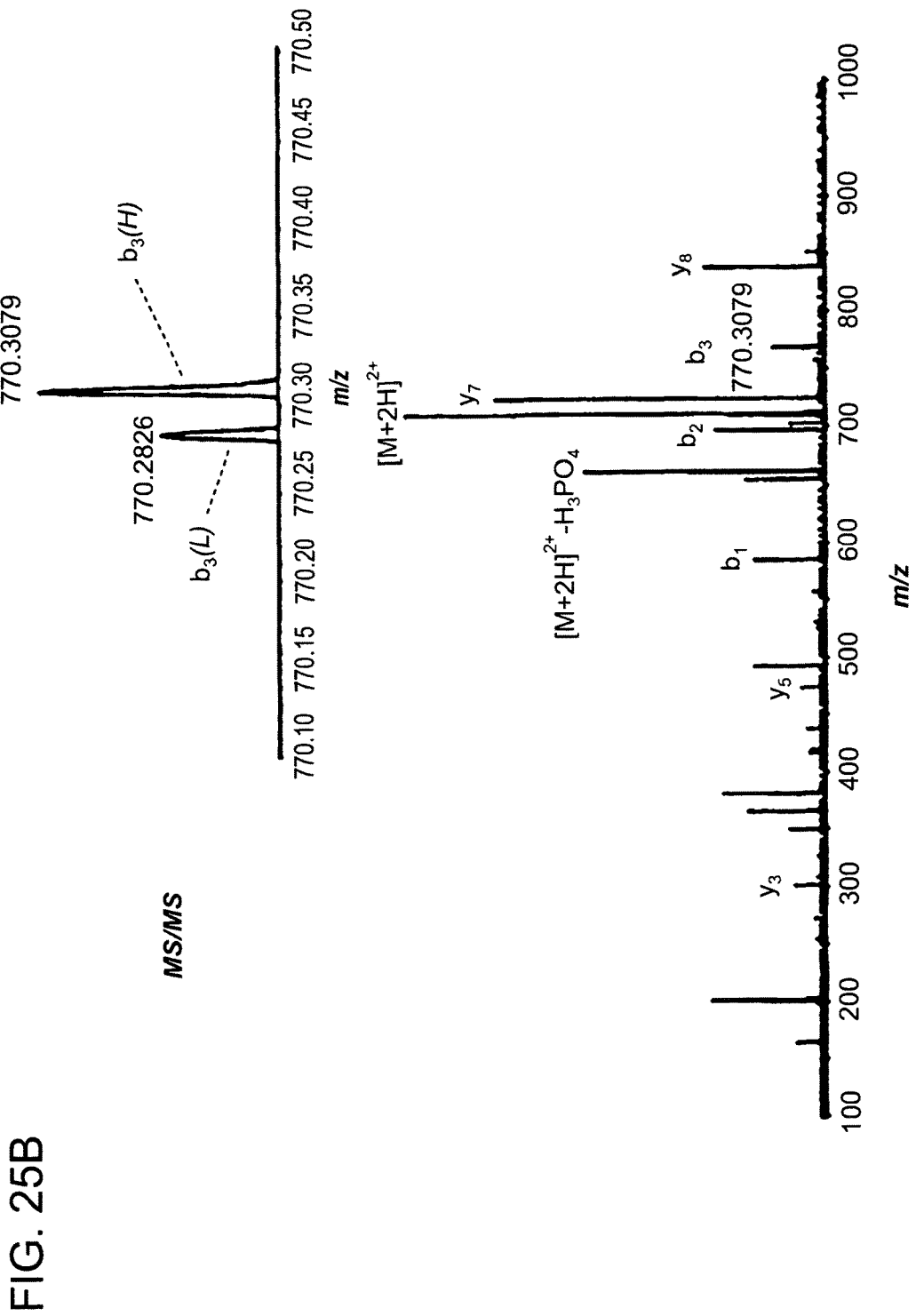
Figure 26A:
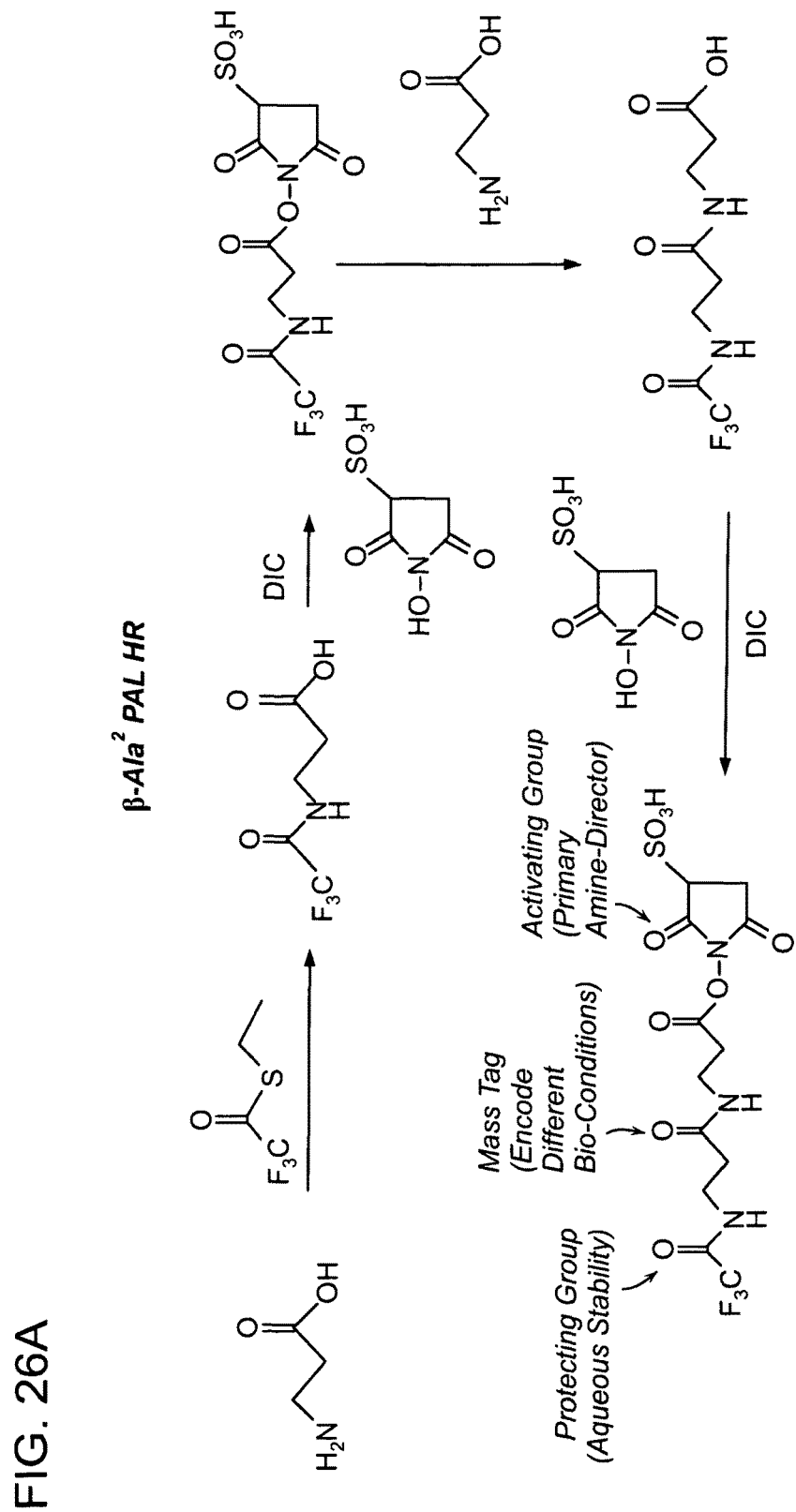
FIG. 26. (A) Synthetic scheme for β-Ala$^2$ PAL HR reagents. (B) Experimental workflow. Proteins are isolated from gel bands, cultured cells, primary tissues, or animal models, digested with trypsin, and the resulting peptides are labeled with light and heavy versions of β-Ala$^2$ PAL HR reagents. Primary amines are regenerated prior to LC-MS/MS by incubation at pH~11.5 for 30 min. Abundance ratios for peptide precursors that are separated by a mass-to-charge (m/z) value equal to (n×0.01753)/z, where n is the number of peptide primary amine groups and z is the peptide charge state, provide relative quantification for peptides in each biological condition.
Figure 26B:
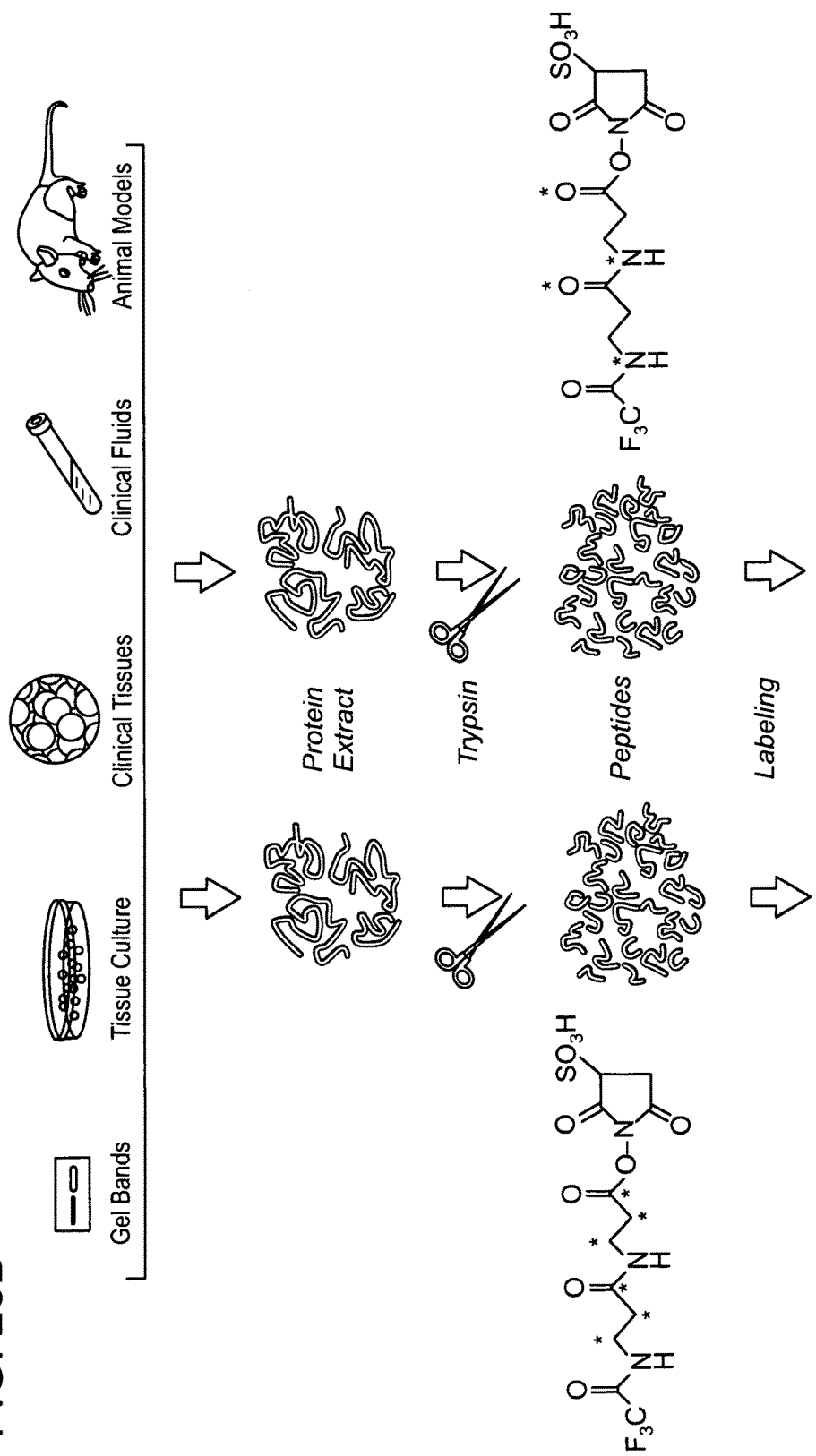
Figure 26B:
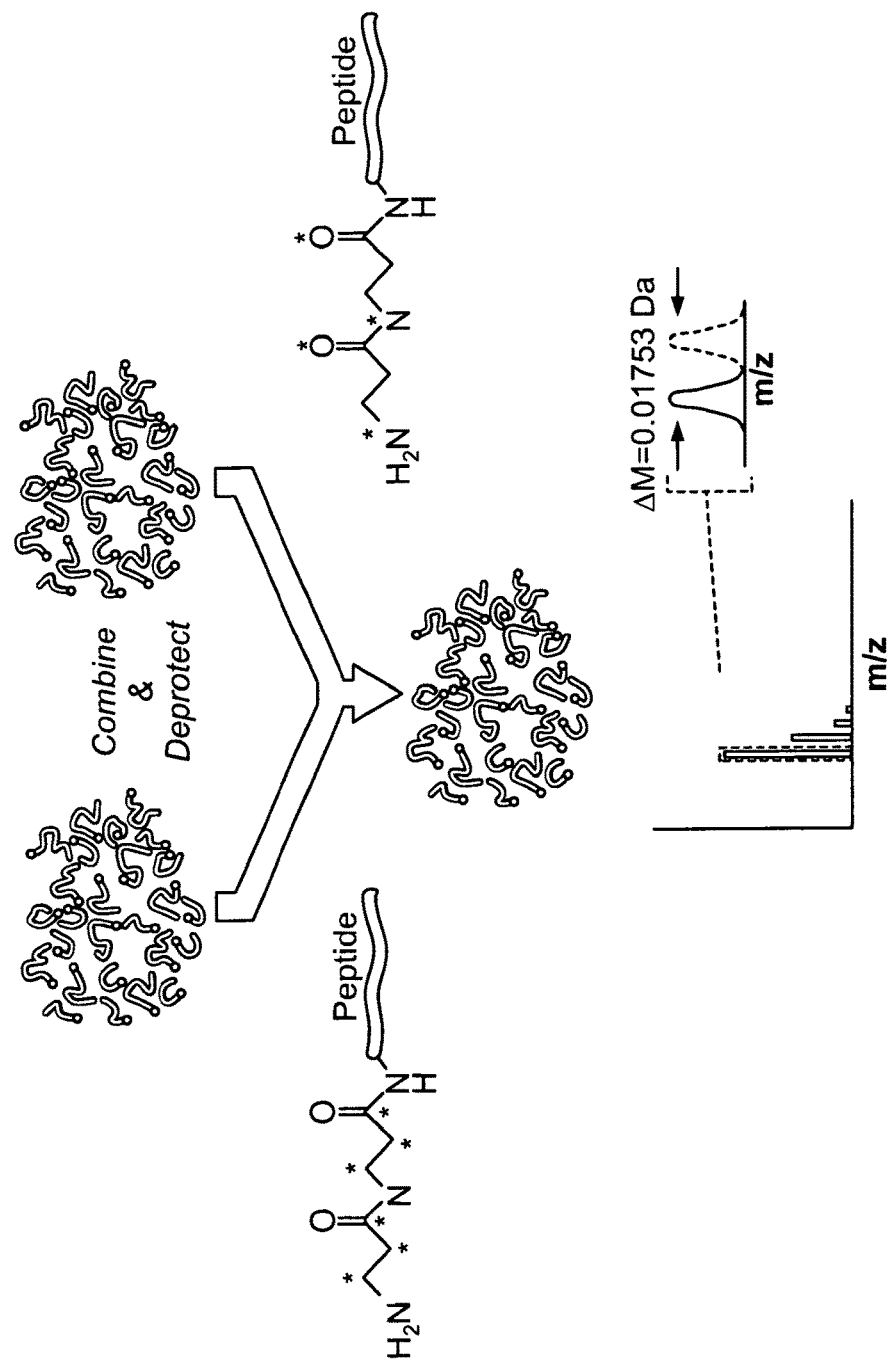
Figure 29A:
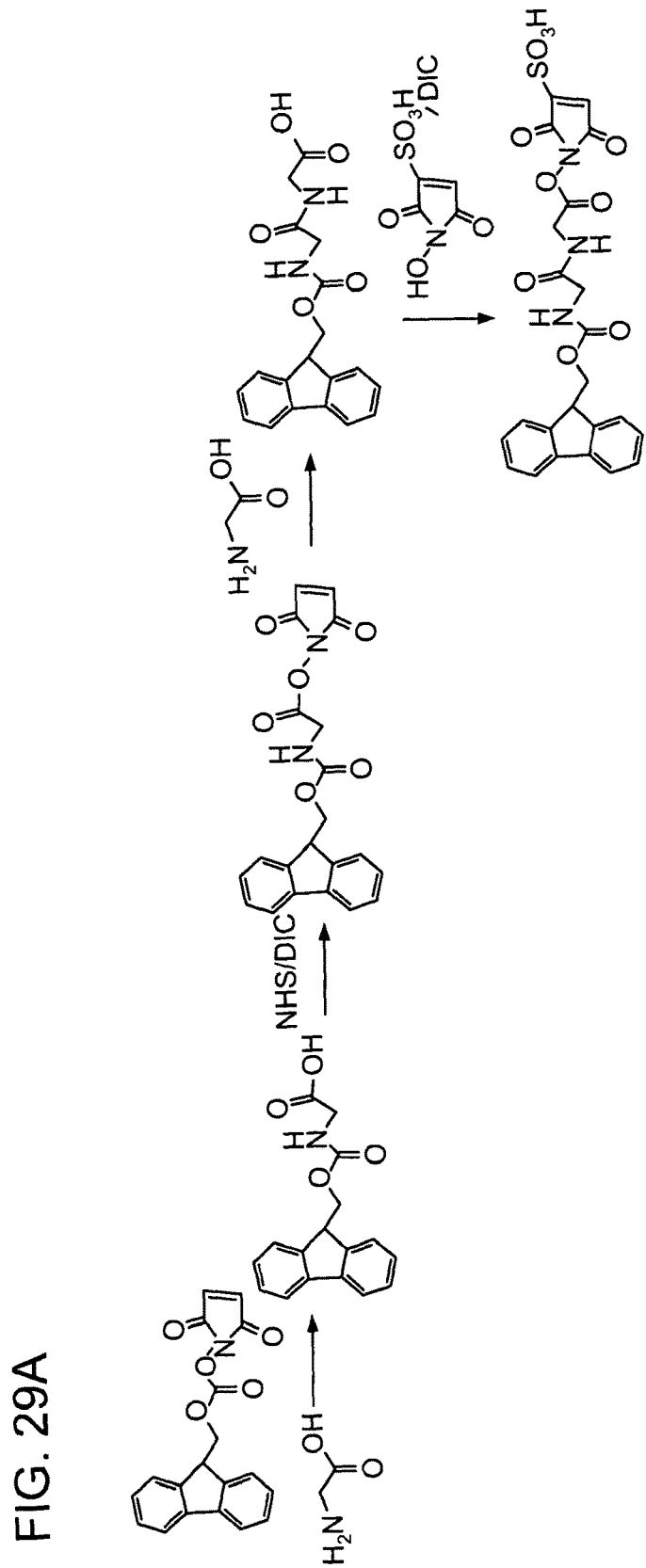
FIG. 29. (A) Synthetic scheme for Gly$^2$ PAL HR reagents. (B) Experimental workflow. Proteins are isolated from gel bands, cultured cells, primary tissues, or animal models, digested with trypsin, and the resulting peptides are labeled with light and heavy versions of Gly$^2$ PAL HR reagents. Primary amines are regenerated prior to LC-MS/MS by treatment with 20% piperidine in DMF for 30 min. Abundance ratios for peptide precursors that are separated by a mass-to-charge (m/z) value equal to (n×0.01262)/z, where n is the number of peptide primary amine groups and z is the peptide charge state, provide relative quantification for peptides in each biological condition.
Figure 29B:
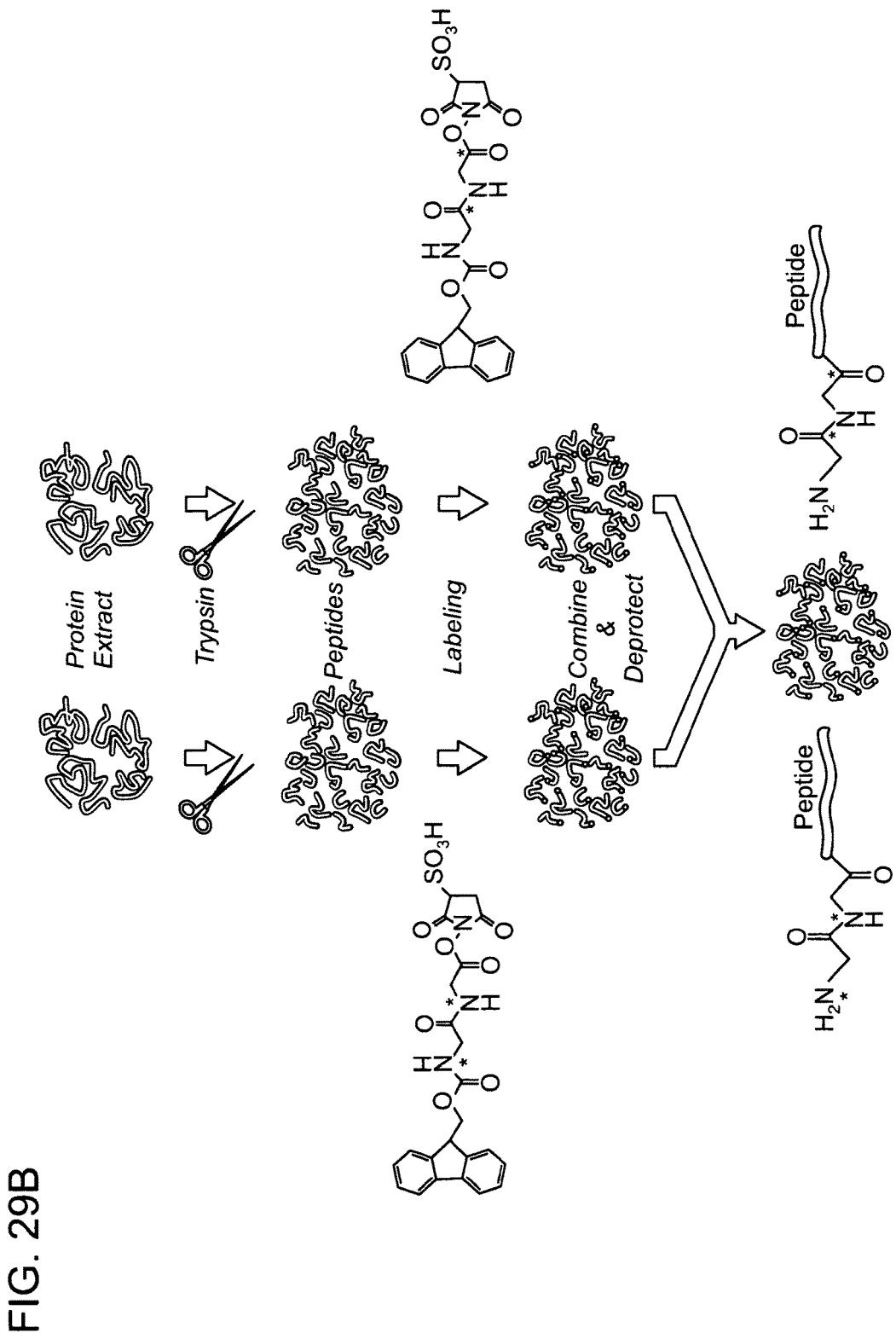
Figure 29B:
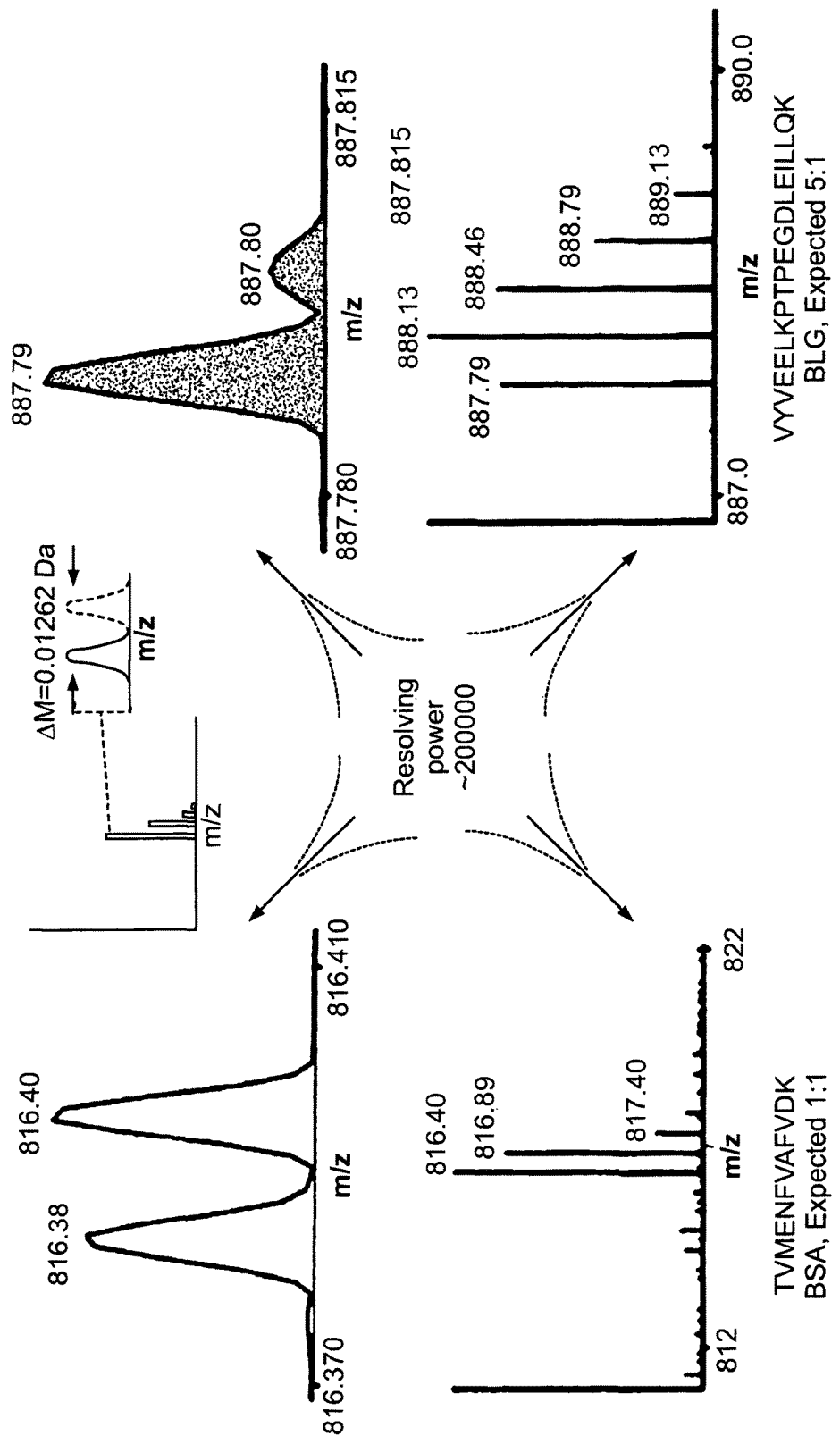

Recent editorials in mass spectrometry and proteomics have reviewed the analytical figures of merit inherent to acquisition of data under high mass resolution conditions (Mann, M. & Kelleher, N. L. *Proc Natl Acad Sci USA* 105, 18132-18138 (2008); Marshall, A. G. & Hendrickson, C. L. *Annual Review of Analytical Chemistry* 1, 579-599 (2008)). In addition to improved mass accuracy, isotopic fine structure, resulting from differences in nuclear binding energies for neutrons that form stable heavy isotopes of the elements C, N, O, and S, becomes visible as mass resolution reaches and exceeds m/Δm~200,000. The ability to experimentally measure these spectral features suggests that the mass defects associated with stable isotopes can be leveraged within the context of relative quantification in proteomics. For example, FIG. 24A shows a mass defect PAL reagent synthesized by coupling tri-fluoroacetate protected glycine onto the primary amine groups of lysine ($Gly^2Lys$ PAL HR). Incorporation of $^{15}N_4$ and $^{13}C_4$ yielded the light and heavy versions, respectively (FIG. 24B). Each $^{15}N/^{13}C$ provided a mass shift of 0.00631 Da, and hence peptides labeled with $Gly^2Lys$ PAL HR were separated by 4×0.00631=0.02524 Da (FIG. 24, bottom). The mass resolution required to distinguish these labels is currently available on high performance mass spectrometers. In practice, both light and heavy forms will be subjected to MS/MS simultaneously due to limitations in the specificity of ion isolation on the majority of mass spectrometers; this provides the added benefit that fragment ions will also appear as doublets, and hence quantification is performed in both MS and MS/MS scans. As a test of this approach, a standard phosphopeptide was labeled (FLApYTGDDAR) in a 1:2 ratio with $Gly^2Lys$ PAL HR reagents. Light and heavy peptides were combined and analyzed by LC-MS/MS. FIG. 25A shows a MS scan in the region near the singly-charged peptide at m/z 1425; the inset demonstrates baseline resolution of the light and heavy peptides, with an approximate abundance ratio of 1:2. Similarly, the MS/MS spectrum (FIG. 25B) exhibited sequence-specific fragment ions, with those that contain the peptide N-terminus (b-type ions) appearing as light and heavy doublets, again in a ratio of 1:2. These data demonstrate the feasibility of labels based on mass defect, and the use of PAL chemistry in their synthesis. FIG. 26 shows another example of PAL HR labels based on the β-alanine multiplex reagent (β-$Ala^2$ PAL HR). FIG. 29 shows another example of PAL HR labels based on the Glycine multiplex reagent ($Gly^2$-PAL HR).

According to the methods of this invention, the analyte to be determined is labeled. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples.

The two or more samples can be mixed to form a sample mixture. In the multiplex analysis, labeling reagents can be used to determine from which sample of a sample mixture an analyte originated. The absolute and/or relative (with respect to the same analyte in different samples) amount (often expressed in concentration or quantity) of the analyte, in each of two or more of the samples combined to form the sample mixture, can be determined. Moreover, the mass analysis of fragments of the analyte (e.g. daughter fragment ions) can be used to identify the analyte and/or the precursor to the analyte; such as where the precursor molecule has been subjected to MS/MS analysis.

For example, the analyte might be a peptide that resulted from the degradation of a protein using an enzymatic digestion reaction to process the sample. Protein degradation can be accomplished by treatment of the sample with a proteolytic enzyme (e.g. trypsin, papain, pepsin, ArgC, LysC, V8 protease, AspN, pronase, chymotrypsin or carboxypeptidease C). By determination of the identity and amount of a peptide in a sample mixture and identifying the sample from which it originated, optionally coupled with the determination of other peptides from that same sample, the precursor protein to the degraded peptide can be identified and/or quantified with respect to the sample from which it originated. Because this method allows for the multiplex determination of a protein, or proteins, in more than one sample (i.e. from a sample mixture), it is a multiplex method.

In some embodiments, this invention pertains to a method comprising reacting each of two or more samples, each sample containing one or more reactive analytes, with a different labeling reagent of a set of labeling reagents. Consequently, one or more analytes of each sample are labeled by reaction of a nucleophile or electrophile of the analyte with the electrophilic or nucleophilic reactive group (RG), respectively, of the different labeling reagents. The labeling process can produce two or more differentially labeled samples each comprising one or more labeled analytes. The labeling reagents of the set can be isomeric or isobaric. The distinct mass shifts associated with each labeling reagent can be used to identify, the sample from which each labeled analyte originated.

Once the analytes of each sample are labeled with the labeling reagent that is unique to that sample, the two or more differentially labeled samples, or a portion thereof, can be mixed to produce a sample mixture. Where quantitation is desired, the volume and/or quantity of each sample combined to produce the sample mixture can be recorded. The volume and/or quantity of each sample, relative to the total sample volume and/or quantity of the sample mixture, can be used to determine the ratio necessary for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantitated, either by relative quantitation of the amounts of analyte in each of the two or more samples or absolutely where a calibration standard is also added to the sample mixture.

The mixture can then be subjected to mass spectrometry techniques wherein MS and MS/MS analyses can be performed on the sample mixture, or fraction thereof, as per the following general procedure: The mass-to-charge ratio of ions is first detected in the MS mode. For instances in which chemical labels of different masses are used, quantification is determined from the relative peak heights or areas of the corresponding MS signals. Next, ions of a particular mass-to-charge ratio from the MS scan can then be selected and then subjected to dissociative energy levels (e.g. collision induced dissociation (CID) or electron transfer dissociation (ETD)) to thereby induce fragmentation of the selected ions. Mass-to-charge ratios of the fragment ions are detected in the MS/MS scan. Depending on the specific mass spectrometer geometry employed, the fragment ions themselves may further dissociate to produce fragments-of-fragments, or MS/MS/MS signals. For instances in which isobaric chemical labels are used, analyte quantification can be determined from the relative peak heights or areas of the corresponding MS/MS signals.

In some circumstances information contained within the MS scan is sufficient to identify the analyte of interest. Often however, the MS-level information is ambiguous and MS/MS level data is required for analyte identification. Those skilled in the art will be aware of the numerous computer programs that are available to assist in analyte identication based on data contained in either MS or MS/MS scans.

In some embodiments, certain steps of the process can be repeated one or more times.

For example, in some embodiments, ions of a selected mass to charge ratio from the first mass spectrometric analysis, different from any previously selected mass to charge ratio, can be subjected to dissociative energy levels to thereby form daughter or fragment ions of at least some fraction of the original selected ion population, as previously described. This process can be repeated iteratively in order to obtain MS and MS/MS data on a significant fraction of analytes contained in the original mixture.

In some embodiments, the whole process can be repeated one or more times. For example, it may be useful to repeat the process one or more times where the sample mixture has first been fractionated (e.g. separated by chromatography or electrophoresis). By repeating the process on each sample fraction, it is possible to analyze all the entire sample mixture. It is contemplated that in some embodiments, the whole process will be repeated one or more times and within each of these repeats, certain steps will also be repeated one or more times such as described above. In this way, the contents of sample mixture can be interrogated and determined to the fullest possible extent.

Those of ordinary skill in the art of mass spectrometry will appreciate that the first and second mass analysis can be performed using a variety of mass spectrometers, each of different geometry. In the case of MS/MS analysis, mass spectrometers can be tandem in space (beam-type) or tandem in time (trap-type) instruments. Examples of these instruments in include quadrupole time-of-flight and ion trap Orbitrap, respectively.

Although tandem mass spectrometers are preferred, single-stage mass spectrometers may be used. For example, analyte fragmentation may be induced near the ion source region via so-called nozzle-skimmer dissociation, followed by mass analysis of the resulting fragments using a single-stage quadrupole or time-of-flight mass spectrometer. In other examples, analytes may be subjected to dissociative energy levels using a laser source and the resulting fragments recorded following post-source decay in time-of-flight or tandem time-of-flight (TOF-TOF) mass spectrometers.

The use of stable isotopes in chemical tags may require a correction of peak intensity associated with the tags based on the natural or artificially created, isotopic abundance, as previously discussed. More specifically, where the volume and/or quantity of each sample that is combined to the sample mixture is known, the relative amount (often expressed as concentration and/or quantity) of the analyte in each sample can be calculated based upon the relative amount of each tagged analyte determined in the MS or MS/MS analysis.

This analysis can be repeated one or more times on selected ions of a different mass to charge ratio to thereby obtain the relative amount of one or more additional analytes in each sample combined to form the sample mixture. As appropriate, a correction of peak intensity associated with the chemical tags can be performed for naturally occurring, or artificially created, isotopic abundance.

Alternatively, where a calibration standard comprising a unique chemical tag linked to an analyte, having the selected mass to charge ratio, has been added to the sample mixture in a known amount (often expressed as a concentration and/or quantity), the amount of the unique chemical tag associated with the calibration standard can be used to determine the absolute amount (often expressed as a concentration and/or quantity) of the analyte in each of the samples combined to form the sample mixture. This is possible because the amount of analyte associated with the chemical tag for the calibration standard is known and the relative amounts of all other chemical tags can be determined for the labeled analyte associated with the selected ions. Since the relative amount of chemical tag, determined for each of the unique chemical tags (including the tag for the calibration standard), is proportional to the amount of the analyte associated with each sample combined to form the sample mixture, the absolute amount (often expressed as a concentration and/or quantity) of the analyte in each of the samples can be determined based upon a ratio calculated with respect to the formulation used to produce the sample mixture. As appropriate, a correction of peak intensity associated with the chemical tags can be performed for naturally occurring, or artificially created, isotopic abundance.

This analysis can be repeated one or more times on selected ions of a different mass to charge ratio to thereby obtain the absolute amount of one or more additional analytes in each sample combined to form the sample mixture. As appropriate, a correction of peak intensity associated with the chemical tags can be performed for naturally occurring, or artificially created, isotopic abundance.

In some embodiments, the methods can be practiced with digestion and/or separation steps. In some embodiments, the steps of the methods, with or without the digestion and/or separation steps, can be repeated one or more times to thereby identify and/or quantify one or more other analytes in a sample or one or more analytes in each of the two or more samples (including samples labeled with support bound labeling reagents). Depending of whether or not a calibration standard is present in the sample mixture for a particular analyte, the quantitation can be relative to the other labeled analytes, or it can be absolute. Such an analysis method can be particularly useful for proteomic analysis of multiplex samples of a complex nature, especially where a preliminary separation of the labeled analytes (e.g. liquid chromatography or electrophoretic separation) precedes the mass spectrometry analysis.

In some embodiments, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis. Moreover, the information from different samples can be compared for the purpose of making determinations, such as for the comparison of the effect on the amount of the protein in cells that are incubated with differing concentrations of a substance that may affect cell growth. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (time-course) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection.

In some embodiments, the analyte can be a nucleic acid fragment in a sample or sample mixture. The information on the nucleic acid fragments can be used to determine the amount (often expressed as a concentration and/or quantity) of identifiable nucleic acid molecules in the sample or sample mixture wherein the sample was degraded prior to the first mass analysis. Moreover, the information from the different samples can be compared for the purpose of making determinations as described above.

In some embodiments, this invention pertains to mixtures (i.e. sample mixtures). The mixtures can comprise at least two differentially labeled analytes, wherein each of the two-labeled analytes can originate from a different sample.

The analytes of the mixture can be lipids. The analytes of the mixture can be steroids. The analytes of the mixture can be small molecules of less than 1500 daltons. The analytes of the mixture comprise two or more analyte types. The analyte types can, for example, be selected from peptides, proteins, nucleic acids carbohydrates, lipids, steroids and/or small molecules of less than 1500 daltons.

The methods, mixtures, kits and/or compositions of this invention can be used for complex analysis because samples can be multiplexed, analyzed and reanalyzed in a rapid and repetitive manner using mass analysis techniques. For example, sample mixtures can be analyzed for the amount of individual analytes in one or more samples. The amount (often expressed in concentration and/or quantity) of those analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein, and associated post-translational modification status, expressed by a cell or tissue. Mass spectrometry, used in combination with the method, mixture, kit and/or composition embodiments of this invention is one possible tool for such global protein analysis.

For example, with a set of four chemical labeling reagents, it is possible to obtain four time points in an experiment to determine up or down regulation of protein expression, for example, based upon response of growing cells to a particular stimulant. It is also possible to perform fewer time points but to incorporate one or two controls. In all cases, up or down regulation of the protein expression, optionally with respect to the controls, can be determined in a single multiplex experiment. Moreover, because many steps of sample processing are performed in parallel the mass spectrometry results are directly comparable, since there is reduced risk that slight variations in protocol may have affected the results.

Analysis of Peptides by Mass Spectrometry

There are preferred inlet systems, ion sources and mass analysers for the purposes of analysing peptides.

In one aspect a chromatographic or electrophoretic separation is preferred to reduce the complexity of the sample prior to analysis by mass spectrometry. A variety of mass spectrometry techniques are compatible with separation technologies particularly capillary zone electrophoresis (CE) and High Performance Liquid Chromatography (HPLC). The choice of ionisation source is limited to some extent if a separation is required as ionisation techniques such as MALDI and FAB which ablate material from a solid surface are less suited to chromatographic separations. For most purposes, it has been very costly to link a chromatographic separation in-line with mass spectrometric analysis by one of these techniques. Those skilled in the art of mass spectrometry will recognize that ionisation techniques based on spraying such as electrospray, thermospray and APCI are all readily compatible with in-line chromatographic separations and equipment to perform such liquid chromatography mass spectrometry analysis is commercially available.

For many biological mass spectrometry applications so called 'soft' ionization techniques are used. These allow large molecules such as proteins and nucleic acids to be ionized essentially intact. The liquid phase techniques allow large molecules to enter the mass spectrometer in solutions with mild pH and at low concentrations. A number of techniques are appropriate for use with this invention including but not limited to Electrospray Ionisation Mass Spectrometry (ESI-MS), Fast Atom Bombardment (FAB), Matrix Assisted Laser Desorption Ionisation Mass Spectrometry (MALDI MS) and Atmospheric Pressure Chemical Ionisation Mass Spectrometry (APCI-MS).

Electrospray Ionisation: Electrospray ionisation requires that the dilute solution of the analyte molecule is 'atomised' or 'nebulized' into the spectrometer, i.e. injected as a fine spray. The solution is, for example, sprayed from the tip of a needle held at a high voltage, in a stream of dry nitrogen. The mechanism of ionisation is not fully understood but is thought to work broadly as follows. In a stream of nitrogen the solvent is evaporated. With a small droplet, this results in concentration of the analyte molecule. Given that most biomolecules have a net charge when analyzed from a mildly acidic solution (e.g., HPLC effluent) this increases the columbic repulsion on the surface of the droplet. As evaporation continues this repulsion ultimately becomes greater than the surface tension of the droplet and the droplet disintegrates into smaller droplets. This process is sometimes referred to as a 'Coulombic explosion'. The sample effluent flow rate, voltage of the spray needle, and diameter of the needle orifice may be adjusted to minimize the size of droplets initially formed, and hence the overall efficiency of analyte ionization. The evaporation continues from the smaller droplets which, in turn, explode iteratively until essentially all the biomolecules are in the vapour phase, as is all the solvent. This technique is of particular importance in the analysis of biomolecules in that the technique imparts a relatively small amount of energy to ions in the ionisation process and the energy distribution within a population tends to fall in a narrower range when compared with other techniques. The ions are extracted out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to extract ions from the ionisation chamber it is possible to control the fragmentation of ions. This is advantageous when fragmentation of ions is to be used as a means of fragmenting a labelled biomolecule. Electrospray ionisation is particularly advantageous as it can be used in-line with liquid chromatography, referred to as Liquid Chromatography Mass Spectrometry (LC-MS).

Matrix Assisted Laser Desorption Ionisation (MALDI): MALDI requires that a molecule solution be embedded in a large molar excess of a photo-excitable 'matrix'. The application of laser light of the appropriate frequency results in the excitation of the matrix which in turn leads to rapid evaporation of the matrix along with its entrapped molecule. Proton transfer from the acidic matrix to the molecule gives rise to protonated forms of the molecule which can be detected by positive ion mass spectrometry, most commonly by Time-Of-Flight (TOF) mass spectrometry. Negative ion mass spectrometry is also possible by MALDI TOF. Although ions must be accelerated to high kinetic energy to attain adequate mass resolution, extraction of ions from the source region is slightly delayed in time as compared to the ionization event. Multiple gentle collisions of analyte with the laser-generated plume yields analyte ions with relatively low internal energy. Use of very high laser power for ionization tends to impart sufficient internal energy into analyte ions such that they fragment after they exit the ion source region.

Fast Atom Bombardment (FAB) has come to describe a number of techniques for vaporising and ionising relatively involatile molecules. In these techniques a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques can be interfaced with liquid phase inlet systems; for example the FAB beam may be directed at the exit end of a separation capillary (electrophoretic or LC) and thereby ionize analyte molecules as the elute from the capillary.

The chemical tags described herein are compatible with various mass spectrometer geometries, ionization sources, and MS/MS fragmentation techniques.

MS/MS and MS Analysis of Peptides: Tandem mass spectrometers allow ions having a wide range of mass-to-charge ratios to be selected and fragmented by various techniques. Although each of these vary somewhat in their exact mechanism, they all function by increasing the internal energy of an analyte ion in a way that results in predicable cleavage of a subset chemical bonds within the analyte. The fragments can then be detected providing structural information about the selected ion. When peptides are analysed by collision induced dissociation (CID) in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. Peptide fragment series are denoted $a_n$, $b_n$, $c_n$, etc. for cleavage at the $n^{th}$ amide bond where the charge of the ion is retained on the N-terminal fragment of the ion. Similarly, fragment series are denoted $x_n$, $y_n$, $z_n$, etc. where the charge is retained on the C-terminal fragment of the peptide ion. For peptides, CID tends to produce b- and y-type fragment ions, along with associated neutral losses of water and ammonia, while electron capture or electron transfer dissociation (ECD/ETD) tend to produce c- and z-type fragment ions.

For CID, trypsin is the favored cleavage agents for tandem mass spectrometry as it produces peptides with basic groups at both ends of the molecule, i.e. the alpha-amino group at the N-terminus and lysine or arginine side-chains at the C-terminus. This favors the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of instruments designed for CAD, the b-series of N-terminal fragments or the y-series of C-terminal fragments predominate. If doubly charged ions are analysed then both series are often detected. Labelling Peptides and Polypeptides and Analysis by LC-MS-MS: In preferred embodiments of this invention, the tags are used for the analysis of mixtures of peptides by liquid chromatography tandem mass spectrometry (LC-MS/MS). After attachment of the tags, analogous peptides from each original sample will be encoded by a mass shift characteristic of each chemical tag within a set or kit of tages. In some cases, the mass of the peptide may be sufficient to identify the source protein. In this case the relative ratio of peptide peak heights or peak areas in the MS scan provide a measure of relative quantification for each peptide. If the mass is not sufficient to identify a peptide, either because a number of peptides in the sample have the same or nearly the same mass or because the peptide is post-translationally modified, then sequence information may be determined by MS/MS analysis. The peptide fragmentation peaks can be used to identify the primary amino acid sequence while the chemically tagged peptide MS peaks give information about the relative quantities of the peptides.

The analysis of proteins by tandem mass spectrometry, particularly mixtures of peptides, is complicated by the 'noisiness' of the spectra obtained. Peptides isolated from biological samples are often contaminated with buffering reagents, denaturants and detergents, all of which introduce peaks into the mass spectrum. As a result, there are often more contamination peaks in the spectrum than peptide peaks and identifying peaks that correspond to peptides is major problem, especially with small samples of proteins that are difficult to isolate. As a result of these confounding issues, various methods are used to determine which peaks correspond to peptides before detailed CID analysis is performed. Triple quadrupole based instruments permit 'precursor ion scanning' (see Wilm M. et al., Anal Chem 68(3):527-33, "Parent ion scans of unseparated peptide mixtures." (1996)). The triple quadrupole is operated in 'single reaction monitoring' mode, in which the first quadrupole scans over the full mass range and ions within each selected mass-to-charge region are subjected to CID in the second quadrupole. The third quadrupole is set to detect only one specific fragment ion, which is usually a characteristic fragment ion from a peptide such as a particular immonium ion, such as that indicative of the precense of a phosphorylated tyrosine residue, or the y-1 type ions that indicate the presence of a lysine or arginine residue at the peptide C-terminus. The presence of phosphate groups on the side chains of serine and threonine residues can also be detected using this technique. An alternative method that can be used on a wide range of mass spectrometer geometries is to scan for doubly charged ions by identifying those ions which when subjected to CID produce fragment ions with higher mass-to-charge ratios as compared to the precursor ion detected in the MS scan. A further method of identifying doubly charged ions is to look for sets of peaks within an isotopic envelope in the MS spectrum which are only 0.5 daltons apart.

By labelling peptides with the mass labels of this invention, a novel form of precursor ion scanning may be envisaged in which peptide peaks are identified by the presence of fragments corresponding to the mass labels of this invention after subjecting the labelled peptides to CID.

Tandem mass spectrometers have the ability to select and fragment molecular ions according to their mass-to-charge (m/z) ratio, and then record the resulting fragment (daughter) ion spectra. Single stage mass spectrometers can also fragment analyte ions, but cannot typically do so in a selective manner. Hence these instruments are suitable for MS/MS analysis only in cases in which single or a small number of analytes are presented for analysis at a given time. More specifically, daughter fragment ion spectra can be generated by subjecting selected ions to dissociative energy levels (e.g. collision-results in dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and hybrid ion trap Fourier transform ion cyclotron and hybrid ion trap Orbitrap mass spectrometers. For a recent review of tandem mass spectrometers please see: R. Aebersold and D. Goodlett, Mass Spectrometry in Proteomics. Chem. Rev. 101: 269-295 (2001). Also see U.S. Pat. No. 6,319,476, herein incorporated by reference, for a discussion of TOF-TOF mass analysis techniques.

Fragmentation By Dissociative Energy Levels: It is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision of peptide molecular ions with an inert gas such as helium, nitrogen, or argon—collision induced dissociation (CID): Those of ordinary skill in the art of mass spectrometry will appreciate that other exemplary techniques for imposing dissociative energy levels that cause fragmentation include, but are not limited to, photo dissociation, electron capture (ECD), electron transfer (ETD), and surface induced dissociation (SID).

The process of fragmenting bonds by CID involves increasing the internal energy state of selected ions, through collision with an inert gas, to a point where bond fragmentation occurs. For example, peptide internal energy can be increased by collision with an inert gas (such as nitrogen, helium or argon) in a collision cell. The amount of internal energy that can be transferred to the ions is proportional to the number of gas molecules that are allowed to enter the collision cell, and the kinetic energy of the peptide ions. When more gas molecules are present, a greater amount of internal energy can be transferred to the selected ions, and less internal energy is transferred when there are fewer gas molecules present. Similarly, peptide internal energy increases with the kinetic energy of the peptide during MS/MS analysis.

It is therefore clear that the dissociative energy level in a mass spectrometer can be controlled. It is also well accepted that certain bonds are more labile than other bonds. The lability of the bonds in an analyte depends upon the nature of the analyte and, in the specific case of peptides, the presence of post-translational modifications. Accordingly, the dissociative energy levels can be adjusted so that the analytes can be fragmented in a manner that is determinable. One of skill in the art will appreciate how to make such routine adjustments to the components of a mass spectrometer to thereby achieve the appropriate level of dissociative energy to thereby fragment at least a portion of labeled analyte ions into fragment ions.

For example, dissociative energy can be applied to ions that are selected/isolated from the first mass analysis. In a tandem mass spectrometer, the selected ions can be subjected to dissociative energy levels and the corresponding fragment ions detected in the MS/MS scan. The selected ions can have a mass to charge ratio that falls within a range of mass to charge ratios depending upon the specific geometry and performance capabilities of the mass spectrometer used in the analysis.

Separation Of The Sample Mixture: In some embodiments the processing of a sample or sample mixture of labeled analytes can involve separation. For example, a sample mixture comprising differentially labeled analytes from different samples can be prepared. Differentially labeled means that each of the samples is labeled with a chemical tag that encodes each constituent of the sample with a unique mass shift relative to analogous constituents of the other samples, and relative to the native or unlabeled constituents. In order to analyze the sample mixture, components of the sample mixture can be separated and mass analysis performed on only a fraction of the sample mixture. In this way, the complexity of the analysis can be substantially reduced since separated analytes can be analyzed by mass spectrometry individually, thereby increasing the sensitivity of the analysis process. Of course the analysis can be repeated one or more times on one or more additional fractions of the sample mixture to thereby allow higher dynamic range of analysis for all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis with the amount of the differently labeled analytes in the sample mixture.

The separation can be performed by chromatography. For example, liquid chromatography/mass spectrometry (LC/MS) can be used to effect such a sample separation and mass analysis. Moreover, any chromatographic separation process suitable to separate the analytes of interest can be used. For example, the chromatographic separation can be normal phase chromatography, reversed-phase chromatography, ion-exchange chromatography, size exclusion chromatography or affinity chromatorgraphy.

The separation can be performed electrophoretically. Non-limiting examples of electrophoretic separations techniques that can be used include, but are not limited to, 1D electrophoretic separation, 2D electrophoretic separation and/or capillary electrophoretic separation.

Relative and Absolute Quantitation Of Analytes: In some embodiments, the relative quantitation of differentially labeled identical analytes of a sample mixture is possible. Relative quantitation of differentially labeled identical analytes is possible by comparison of the relative amounts of labeled analyte peak height or peak area that are determined in the MS or MS/MS scans. Put differently, where each chemical tag can be correlated with information for a particular sample used to produce a sample mixture, the relative amount of that chemically tagged analyte, with respect to other tagged analytes observed in the MS or MS/MS analysis, is the relative amount of that analyte in the sample mixture. Where components combined to form the sample mixture are known, the relative amount of the analyte in each sample used to prepare the sample mixture can be back calculated based upon the relative amounts of tagged analyte observed for the ions of the labeled analyte. This process can be repeated for all of the different labeled analytes observed in the analysis. In this way, the relative amount (often expressed in terms of concentration and/or quantity) of each reactive analyte, in each of the different samples used to produce the sample mixture, can be determined.

In other embodiments, absolute quantitation of analytes can be determined. For these embodiments, a known amount of one or more differentially labeled analytes (the calibration standard or calibration standards) can be added to the sample mixture. The calibration standard can be an expected analyte that is labeled with one chemical label of the set or kit of labels used to label the analytes of the sample mixture provided that the tag for the calibration standard is unique as compared with any of the samples used to form the sample mixture. Once the relative amount of chemical tag for the calibration standard, or standards, is determined with relation to the relative amounts of the tags for the differentially labeled analytes of the sample mixture, it is possible to calculate the absolute amount (often expressed in concentration and/or quantity) of all of the differentially labeled analytes in the sample mixture. In this way, the absolute amount of each differentially labeled analyte (for which there is a calibration standard in the sample from which the analyte originated) can also be determined based upon the knowledge of how the sample mixture was prepared.

It is an object of this invention to provide methods and labels that can be used to produce protected amino groups in molecules, particularly peptides and proteins while retaining a functionality that is readily protonated under typical ionization conditions used in mass spectrometry analysis, which is amenable for purification of labelled biomolecules and generally has analytical figures of merit compatible with the analysis of the labelled biomolecules by mass spectrometry.

It is an object of this invention to provide compounds which have desirable features as mass labels and methods for the use of those compounds to provide identification and relative quantification of associated analytes by mass spectrometry.

In a preferred embodiment the PAL reagent has a characteristic isotope abundance distribution. In one such embodiment, the PAL is substituted with one or more atoms of stable isotopes hydrogen, carbon, nitrogren, sulfur, or phosphorus. In a second embodiment, the PAL reagent comprises a mixture of two or more isotopes of the same compound, such that the reagent imparts are a characteristic distribution of isotopes to a population of labelled ions.

The invention also provides an array of mass tags for labelling one or more molecules to be characterised by mass spectrometry, which array comprises two or more mass tags as defined above. In one embodiment, every mass tag in the array has the same chemical structure, and each mass tag in the array is an isotopomer of the other mass tags in the array such that each mass tag in the array has a different mass. These arrays of tags are useful for investigating a plurality of analytes simultaneously.

In a second typical aspect of this invention there is provided a method of analysing a polypeptide comprising the steps of: 1. labelling free amino functionalities in the polypeptide with a reagent that targets polypeptide free amine groups, and itself contains a readily ionizable nitrogen moiety; 2. cleaving the polypeptide with a sequence specific cleavage reagent, either before or after the polypeptide is labeled with the reagents described herein; and 3. analysing the cleavage peptides by mass spectrometry.

In preferred embodiments of this aspect of the invention, the labelled peptides are separated by application of one or more analytical separation techniques prior to analysis by mass spectrometry. In more preferred embodiments, certain subclasses of the labelled peptides generated by the cleavage reagent are further enriched by analytical techniques such as immobilized metal affinity chromatography for quantification of phosphorylated peptides. Similarly other peptide subclasses may be targeted after labeling, including but not limited to, glycosylated, sulfated, acetylated, and methylated peptides.

The invention also provides a kit comprising the PAL reagents of this invention and pre-packaged affinity or desalting columns for additional purification of labelled analyte molecules. In preferred embodiments the kit may additionally comprise reaction buffers for the coupling of the tag to analyte molecules, buffers for washing of the affinity or desalting columns after the peptides have been labeled and buffers for elution of the labelled peptides from the resin after the unreacted tags have been washed away. Preferred wash buffers will vary depending on the specific resin used in the column. Examples may include, but are not limited to, water, acetonitrile, phosphate, urea, ammonium acetate and borate. In addition a kit may contain buffers for removal of the protecting group. Examples may include, 250 mM sodium carbonate, trifluoroacetic acid, or 20% piperidine in DMF.

In the case of protecting groups that contain fluorine, another preferred embodiment involves analysis of the labeled and protected peptides. Fluorine will alter the isotope distribution of a tagged species as it is known to comprise almost exclusively a single isotope, so higher mass isotopes will be of reduced intensity when compared with the corresponding hydrogenated species. Halogen atoms will also introduce a mass defect into the tags which under certain circumstances may provide a further evidence that a particular peak or signal observed in a MS scan is a labeled peptide.

Further labelling of cleavage peptides generated from PAL labelled proteins: In certain embodiments of this invention, a PAL labelled polypeptide or protein is cleaved with a sequence specific cleavage reagent or as a result of a biological protease in vivo, and the cleavage peptides are analysed by mass spectrometry. In preferred embodiments of this aspect of the invention, the cleavage peptides are labelled further on the amino groups exposed by the cleavage of the peptides. Since the initial labelling of the polypeptide will have blocked all other free amino groups, only the newly exposed amino groups at the N-termini of the cleavage peptides will be available. Furthermore, the N-terminal peptide of the parent polypeptide will have no free amino group after cleavage as this will have been blocked with the PAL reagent of this invention. This methodology would be useful to identify newly formed N-termini that result from an active protease in cells and tissues.

Proteins contain various nucleophilic functionalities, besides amino groups; that can be labelled using reagents that are reactive to these functionalities. Proteins typically contain thiol, amino, hydroxyl and imidazole groups. These may all be labelled with appropriate reagents if desired. In preferred embodiments of this invention, thiol groups are labelled prior to labelling of free amino groups. Numerous methods for selective labelling of thiols are known in the art, although preferred reagents include iodoacetamide, vinylpyridine, phenyl vinyl sulphone and maleimide compounds.

The invention also provides a method of analysing polypeptides. In this method the polypeptide analytes are covalently labelled with a compound that targets peptide free amine groups, and itself contains a readily ionizable nitrogen moiety. A polypeptide or peptide or mixtures of polypeptides or peptides can be isolated for analysis by any of the conventional means such as electrophoresis, chromatography or affinity chromatography. For the purposes of mass spectrometry, it is preferred that polypeptides or proteins are not contaminated with non-volatile salts or detergents. Various techniques for 'desalting' a polypeptide or peptide mixture are known in the art such as gel filtration, dialysis or the use of hydrophobic or cation/anion exchange resins. A particularly convenient and simple method for de-salting peptides involves aspiration of a small quantity of a solution of the peptide or polypeptide mixture in a pipette tip incorporating C18 reversed phase chromatography resin. Peptides adhere strongly to the resins while many undesirable contaminants do not bind and are washed away.

The captured peptide material can be subsequently eluted with an appropriate volatile buffer for analysis. This sort of 'sample conditioning' substantially improves the detection sensitivity of the analysis of the peptides. Pipette tips pre-packaged with appropriate resins and instructions for their use are commercially available from Millipore (Bedford, Mass., USA) under the trademark 'Zip Tip'. Desalting procedures may take place after labelling of the analyte to remove unreacted tags.

The inventors have also observed that PAL reagents exhibit increased acqueous stability as compared to other commercially available stable isotope reagents, such as iTRAQ, used for relative quantification of biomolecules. This facilitates labeling of polypeptides that are bound to reversed phase chromatography resins. This type of in situ labeling provides improved detection limits because additional sample handling that is typically required with the iTRAQ reagent, such as lyophilization of organic solvents that are otherwise required to stabilize the reagent, are not necessary with PAL reagents. Accordingly, it is envisaged that pipette tips, spin columns and cartridges packed with a reversed phase chromatography resin will be useful tools for the facile clean-up and labeling of polypeptides, especially in cases where biological samples are present in very limited supply, in preparation for relative quantification studies by mass spectrometry.

In another embodiment of the invention the tagged peptides, resulting from direct labeling of the peptides themselves or derived from PAL labelled proteins, are subjected to analytical separation prior to analysis by mass spectrometry. Most analytical separation techniques that can be applied to peptides will be applicable with this invention, such as Capillary Electrophoresis (Moini 2002), High Performance Liquid Chromatography (Morand, Burt et al. 2001), Capillary Iso-electric Focusing (Tang, Harrata et al. 1997; Shen, Berger et al. 2000), Ion Exchange Chromatography and Size Exclusion Chromatography (Liu, Lin et al. 2002). In more preferred embodiments multidimensional chromatography (Washburn, Wolters et al. 2001; Wolters, Washburn et al. 2001; Liu, Lin et al. 2002) is applied to the tagged peptides.

Quantitative Analysis of Tagged Peptides: The present invention further provides a method for characterising molecules in which a plurality of molecules are characterised by mass spectrometry, wherein the characterisation includes determination of the quantity present of at least one of the molecules, or relative quantities present of two or more of the molecules.

In this method, it is preferred that each of the plurality of molecules to be analysed is labelled with a different chemical tag reagent of the present invention, such that both the identity and quantity of each molecule may be determined by mass spectrometry.

Using the methods and tags of the present invention, mass spectra can be obtained of sufficiently high quality that integration of spectral peak areas or peak heights can give reliable data on the relative quantities of the species that are present.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Synthesis of Trifluoroacetyl β Alanine (or $^{13}$C-3, $^{15}$N-1 Form), Trifluoroacetyl Alanine, and Trifluoroacetyl Glycine 2 mmol of β alanine (Sigma-Aldrich; or $^{13}$C-3, $^{15}$N-1 form, Cambridge Isotope Laboratories, Cambridge, Mass.), alanine (Sigma-Aldrich), or glycine (Sigma-Aldrich), was dissolved in 4 mL of 50% acetonitrile in a glass vial with a piercable septum and stirbar. To this mixture was added 4 mmol of 4-methyl morpholine (NMM, Sigma-Aldrich) and 4 mmol of S-ethyl trifluorothioacetate (Sigma-Aldrich). A needle was placed in the septum to allow venting of ethanethiol. The mixture was allowed to stir overnight at room temperature. Removal of solvent afforded an oil.

Example 2

Synthesis of Trifluoroacetyl Proline

Two mmol of proline (Sigma-Alrich) was added to 4 mL of acetonitrile (Themo Fisher Scientific) in a glass vial with a piercable septum and a stirbar. To this mixture was added 4 mmol of 4-methyl morpholine and 4 mmol of S-ethyl trifluorothioacetate. A needle was placed in the septum to allow venting of ethane thiol. The mixture was allowed to stir overnight at room temperature. Removal of solvent afforded an oil.

Example 3

Synthesis of Trifluoroacetyl β Alanine (or $^{13}$C-3, $^{15}$N-1 Form) NHS Ester To 2 mmol of trifluoroacetyl-β alanine oil (or 2 mmol $^{13}$C-3, $^{15}$N-1 trifluoroacetyl-β Alanine oil) was added 2 mL of dimethyl formamide (DMF, Sigma-Aldrich) and 2 mmol N-hydroxysuccinimide (Sigma-Aldrich). The solution was chilled on ice for 5 minutes, and 500 µL of thionyl chloride (Sigma-Aldrich) was added dropwise with stirring. The mixture was kept on ice for 5 minutes, and then incubated at room temperature for 2 hours. The reaction products were diluted with chloroform (Sigma-Aldrich) and subjected to silica gel chromatography (12 g Redisep, Teledyne Isco, Lincoln, Nebr.). After washing with chloroform, the ester was eluted with 10% ethanol in chloroform.

Example 4

Synthesis of Trifluoroacetyl β Alanine (or $^{13}$C-3, $^{15}$N-1 Form) N-Hydroxysulfosuccinimide Ester 2 mmol of trifluoroacetyl β alanine (or $^{13}$C-3, $^{15}$N-1 form) oil was added to 5 mL of DMF and 2 mmol of N-hydroxysulfosuccinimide (Thermo Fisher Scientific). This was followed by the addition of 2.2 mmol diisopropylcarbodiimide (DIC, Sigma-Aldrich). The mixture was incubated at room temperature for 2 hours, followed by filtration to remove the DIC-urea. The product was precipitated by addition of chloroform and collected by vacuum filtration.

Example 5

Synthesis of Trifluoroacetyl Alanine N-hydroxysulfosuccinimide ester and Trifluoroacetyl Glycine N-hydroxysulfosuccinimide Ester 2 mmol of trifluoroacetyl alanine or trifluoroacetyl glycine oil was added to 5 mL of DMF and 2 mmol of N-hydroxysulfosuccinimide. This was followed by the addition of 2.2 mmol DIC. The mixture was incubated at room temperature for 2 hours, followed by filtration to remove the DIC-urea. Solvent removal afforded an oil.

Example 6

Synthesis of Trifluoroacetyl Proline N-hydroxysulfosuccinimide Esters 2 mmol of trifluoroacetyl proline oil was added to 5 mL of DMF and 2 mmol of N-hydroxysulfosuccinimide. This was followed by the addition of 2.2 mmol DIC. The mixture was incubated at room temperature for 2 hours, and the DIC-urea byproduct was removed by filtration. The mixture was diluted with chloroform, and purified by silica gel chromatography (12 g Redisep). Solvent removal afforded an oil.

Example 7

Synthesis of Pyridyl Acetic Acid Labeled β Alanine 0.250 mmol Fmoc-β alanine attached to Wang's resin (Novabiochem, San Diego, Calif.) was weighed into a reaction vessel with frit (Extract clean SPE tube, Grace, Deerfield, Ill.) and treated with DMF with rotation at room temperature for 10 minutes. DMF was then removed by air pressure, and the Fmoc group was removed by addition of 4 mL 20% piperidine (Sigma-Aldrich) in DMF followed by end-over-end rotation for minutes. The resin was then washed with 30 mL DMF. 3-pyridyl acetic acid (MP Biomedicals, Solon, Ohio) was coupled by addition of 1 mL DMF, 1 mmol 3-pyidyl acetic acid in 3 mL DMF, 1 mmol NMM, 1 mmol hydroxybenzotriazole (Novabiochem) in 1 mL DMF, and 1 mmol benzotriazol-1-yl-oxytripyrrolidino-phosphonium hexafluorophosphate (PyBOP, NovaBiochem) in 1 mL DMF, letting the mixture incubate one hour at room temp with end-over-end rotation. After coupling the resin was washed extensively with 30 mL DMF, 30 mL dichloromethane, 30 mL ethanol, 30 mL acetonitrile, and finally with 30 mL of DMF. The product was then cleaved by addition of 4 mL 95% TFA (Thermo Fisher Scientific)/2.5% triisopropyl silane (Sigma)/2.5% water, for 2 hours with end over end rotation. Cleavage solution was flushed from the resin, added to an equal volume 50% acetonitrile, and lyophilized overnight. The product dried to dark orange oil.

Example 8

Synthesis of Pyridyl Acetic Acid modified β Alanine N-hydroxysulfosuccinimide Ester 0.25 mmol 3-pyridyl acetic acid modified β alanine oil was dissolved in 1.5 mL dichloromethane (Sigma-Aldrich) and 400 μL DMF. 0.25 mmol N-hydroxysulfosuccinimide in 1 mL DMF, and 1 mmol DIC were then added. The reaction proceeded for 2 hours at room temperature, after which the DIC-urea was removed by filtration. Removal of solvent afforded a dark orange oil. The oil was reconstituted in 2 mL 50% dimethyl sulfoxide (DMSO, Sigma-Aldrich)/25% acetonitrile/25% water, aliquoted and frozen.

Example 9

Labeling Peptides with Trifluoroacetyl Beta Alanine NHS Ester and $^{13}$C-3, $^{15}$N-1 Trifluoroacetyl Beta Alanine NHS Ester In two separate reactions, [Glu-1]-Fibrinopeptide B (Sigma-Aldrich) or substance P (Sigma-Aldrich, 1 nmol in 1-2 μL of water) was added to a solution of 70 μL ethanol and 30 μL of 500 mM triethylammonium bicarbonate pH 8.5. Light or heavy Tfa-β alanine NHS ester was added (approximately 20 μmol in 20 μL of acetonitrile) and allowed to react for 1 hour at room temperature. After labeling, reactions were combined (or not) and either diluted with 0.1% formic acid, desalted using C18 zip tips (Millipore), and analyzed by MALDI MS (see example 20), or were first deprotected. Deprotection was achieved by adding 500 mM sodium carbonate, pH 11.3 until the pH was ~11, and incubating at 50 C for 60 minutes. This solution was then acidified with Tfa, desalted using zip tips, and analyzed by MALDI-MS (see example 20).

Example 10

Peptide Labeling Experiments with Trifluoroacetyl Glycine Sulfo NHS Ester, Trifluoroacetyl Alanine Sulfo NHS Ester, or Trifluoroacetyl Proline Sulfo NHS Ester

[Glu-1]-Fibrinopeptide B (1 nmol dissolved in 2 μL of water) was added to a solution of 70 μL ethanol and 30 μL of 500 mM 4-(2-hydroxyethyl)-1-piperazineethanesulfonic acid (HEPES, Sigma-Aldrich), pH 8.0. Either trifluoroacetyl glycine N-hydroxysulfosuccinimide ester, trifluoroacetyl alanine N-hydroxysulfosuccinimide ester, or trifluoroacetyl proline N-hydroxysulfosuccinimide ester was added (approximately 1 μmol in 20 μL of 50% acetonitrile) and allowed to react for 1 hour at room temperature. After labeling, reactions were diluted with 0.1% formic acid, desalted using zip tips, and analyzed by MALDI MS (see example 20), or were first deprotected. Deprotection was achieved by adding 1:5 ammonia/water, pH 11.5 (until the pH was ~11), and incubating at 50° C. for 60 minutes. This solution was then acidified with Tfa, desalted using zip tips, and analyzed by MALDI-MS (see example 20).

Example 11

Peptide Labeling Experiments with 3-Pyridyl Acetic Acid Modified β Alanine N-hydroxsulfosuccinimide Ester

[Glu-1]-Fibrinopeptide B (1 nmol dissolved in 2 μL of water) was added to a solution of 70 μL ethanol and 30 μL of 500 mM HEPES pH 8.0. The N-hydroxysulfosuccinimide ester of 3-pyridyl acetic acid modified β alanine was added (approximately 2.5 μmol in 2 mL 50% DMSO/25% acegtonitrile/25% water) and allowed to react for 1 hour at room temperature. After labeling, reactions were diluted with 0.1% formic acid, desalted using zip tips, and analyzed by MALDI MS (see example 20), or were first deprotected. Deprotection was achieved by adding 1:5 ammonia/water, pH 11.5 (until the pH was ~11), and incubating at 50° C. for 60 minutes. This solution was then acidified with Tfa, desalted using zip tips, and analyzed by MALDI-MS (see example 20).

Example 12

Determination of Aqueous Hydrolysis Rates

1 μmol of TFA-β alanine N-hydroxysuccinimide ester was added to 1 mL 0.1% formic acid. The solution was immediately analyzed by FI-ESI-MS (mobile phase=50% acetonitrile with 0.1% formic acid, spray voltage=4 kV, flow rate=50 μL/min) using an LCQ ion trap mass spectrometer (Thermo Fisher Scientific, San Jose, Calif.). A full loop (5 μL) injection was performed every 5 minutes for about 50 minutes. The relative intensity of the peaks was reported vs. the time of the plug. The experiment was repeated with 1 μmol commercial iTRAQ reagent.

Example 13

Millipore Ziptip Solid Phase Labeling

μC18 Millipore ziptips were equilibrated with 20 μL 80% MeCN/0.1% TFA and 30 μL 0.1% TFA. 2 picomoles [Glu-1]-fibrinopeptide B (20 μL 100 fmol/uL in 0.1% Formic acid) was loaded onto tip. Then, 10 μL of TFA-β alanine N-hydroxysulfosuccinimide ester solution (consisting of 1 μmole ester in 80 μL water and 10 μL 1 M triethylammonium bicarbonate, pH 8.5) was pipetted up and down in the ziptip ten times. A final 10 μL aliquot was drawn up into the tip, and was allowed to incubate for 10 minutes at room temperature. The tip was then washed 2 times with 10 μL 0.1% TFA, and the labeled peptide was eluted to the MALDI plate with 1.5 μL 80% acetonitrile/0.1% TFA, and subjected to MALD-MS (see example 20), or was first deprotected. Deprotection was achieved by rinsing the tip 5 times with 20 μL 100 mM potassium hydroxide, pH 13. A final 20 μL aliquot was drawn into the tip, which was then allowed to incubate for 2 hours at room temperature. The liquid was then expelled, washed 5 times with 10 μL 0.1% TFA, eluted with 1.5 μL 80% acetonitrile/0.1% TFA, and subjected to MALD MS analysis (see example 20).

Example 14

Labeling of Peptides Immobilized on C18 (Column Format)

A precolumn (360 O.D. μm×180 I.D. μm fused silica packed with 4 cm POROS10R2 Applied Biosystems, Framingham, Mass.) was equilibrated with 20 μL 80% acetonitrile/0.1% TFA followed by 30 μL 0.1% TFA. Once equilibrated, 2 μmol [glu-1] fibrinopeptide B (20 μL 100 fmol/uL in 0.1% formic acid) was loaded, and the column was washed with 20 μL 500 mM potassium phosphate, pH 8. Labeling solution was prepared by adding 5 μL Trifluoroacetyl-β alanine N-hydroxysuccinimide ester (1 μmol in 5 μL 50% MeCN) to 75 uL water and 20 uL pH 8 500 mM Phosphate buffer. It was immediately flushed over the column at a flow rate of approximately 15 μL/min for 2 minutes. The flow was stopped, and the column incubated at room temperature for 10 minutes, and then washed with 20 μL 0.1% formic acid. The precolumn was then connected via a microunion (Upchurch Scientific, Oak Harbor, Wash.) to an analytical column (360 μm O.D.×100 μm I.D. fused silica packed with 10 cm POROS10R2 with an integrated emitter tip. Peptides were eluted with an HPLC gradient (0-100% B in 30 minutes; A=0.2M acetic acid; B=70% acetonitrile with 0.2M acetic acid) into a mass spectrometer (Quantum, Thermo Fisher Scientific, San Jose, Calif., spray voltage=2.5 kV).

Example 15

Labeling of Peptides Derived From Standard Proteins

BLG (b-lactoglubulin), BSA (Albumin, Bovine), Ovalbumin (Albumin, chicken egg white), and BGAL (b-galactosidase) (all from Sigma-Aldrich) were reconstituted in 100 mM ammonium bicarbonate to 10 μg/μL. 500 μg of each protein solution was then diluted to 250 μL with 100 mM ammonium bicarbonate. After addition of 25 μL 100 mM DTT, each solution was heated for 30 minutes at 60° C. After 30 minutes, solutions were cooled. 550 mM IAA was then added, and allowed to react for 30 minutes in the dark. 20 μg of trypsin (Promega, Madison, Wis.) was then added to each tube, and allowed to incubate at 37° C. overnight.
The following solutions were prepared from the 10 pmol/uL desalted tryptic digests: Solution 1: 25 uL BSA, 12.5 uL BGAL, 50 uL BLG, 50 uL OVAL+362.5 uL 0.1% formic acid; Solution 2: 25 uL BSA, 25 uL BGAL, 10 uL BLG, 25 uL OVAL+415 uL 0.1% formic acid. 15 μL of protein solution 1 (above) was added to 15 μL 1 M triethylammonium bicarbonate (TEAB), 70 μL ethanol, and 50 μL TFA-β alanine N-hydroxysulfosuccinimide ester. In a separate reaction, 15 μL of protein solution 2 (above) was added to 15 μL 1 M TEAB, pH 8.5, 70 μL ethanol, and 50 μL $^{13}$C-3, $^{15}$N-1 TFA-β alanine N-hydroxysulfosuccinimide ester. Solutions were allowed to react for one hour at room temperature. After one hour, solutions were combined. To deprotect, 500 μL 1:5 ammonia/water was added and the reactions were heated to 50° C. for 30 minutes. Following deprotection, the reaction was acidified with TFA, and dried overnight in the speedvac. After drying, peptides were reconstituted in 0.1% formic acid and analyzed by LC-MS on a hybrid ion-trap/orbitrap mass spectrometer (ThermoFisher Scietific, San Jose, Calif.).

Example 16

Labeling of K562 Tryptic Peptides with Trifluoroacetyl β Alanine N-Hydroxysulfosuccinimide Ester and $^{13}$C-3, $^{15}$N-1 Trifluoroacetyl β Alanine N-Hydroxysulfosuccinimide Ester K562 cells were cultured in RPMI 1640 media supplemented with 10% FBS and 1% penicillin/streptomycin at 37° C. in 5% $CO_2$. Aliquots of ~5e7 cells were harvested by centrifugation during log phase. After washing twice with 20 mL phosphate buffered saline, the pellet was lysed with 3 mL of 8M urea, 100 mM ammonium bicarbonate, and 30 μL each of Sigma-Aldrich phosphatase inhibitor cocktails I and II. Protein concentration was determined using the Bradford Assay (Bio-rad laboratories, Hercules, Calif.). Proteins were reduced by adding dithiothreitol (DTT) to a final concentration of 10 mM and incubating for 30 minutes at 60° C., and alkylated with iodoacetamide (final concentration 20 mM) for 30 minutes in the dark at room temperature. Excess iodoacetamide was quenched by the addition of DTT to a final concentration of 20 mM. This solution was diluted to a final volume of 12 mL in 0.1M ammonium bicarbonate. Trypsin (150 μg, 1:50 enzyme:substrate) was added and digestion was performed at 37° C. overnight. The resulting peptide solution was acidified with 10% TFA, and desalted on a $C_{18}$ solid phase extraction cartridge. Unless noted otherwise, 25% acetonitrile with 0.1% TFA was used for peptide elution from $C_{18}$. Eluted peptides (400 μg) were lyophilized by vacuum centrifugation and stored at −80° C. To 400 μg dried tryptic peptides was added 280 μL water, 120 μL 1 M HEPES pH 8.0, and trifluoroacetyl β alanine N-hydroxysulfosuccinimide ester (approximately 4 μmol in 20 μL 50% MeCN) and allowed to react for 1 hour at room temperature. In a separate reaction, 280 μL water, 120 μL 1 M HEPES pH 8.0, and $^{13}$C-3, $^{15}$N-1 Trifluoroacetyl β alanine N-hydroxysulfosuccinimide ester (approximately 4 μmol in 20 μL 50% MeCN) were added to 400 μg dried peptides and the solution was incubated for 1 hour at room temperature. After 1 hour, samples were combined and deprotection was achieved by adding 500 μL 1:5 ammonia, pH 11.5, and 100 μL 250 mM sodium carbonate pH 11.5, and incubating at 56° C. for 60 minutes. This solution was then acidified with Tfa, and analyzed by MALDI-MS (see example 20).

Example 17

Procedure for Phosphopeptide Enrichment 1 mL Ni-NTA beads (Quiagen, Valencia, Calif.) were washed 3× with 800 μL water, and treated with 800 μL of 100 mM ethylene diamine tetraacetic acid (EDTA, Sigma-Aldrirch), pH 8.0 for 30 minutes with end-over-end rotation. EDTA solution was removed, and beads were then washed 3× with 800 µL water, and treated with 800 µL of 10 mM aqueous $FeCl_3$ (Sigma-Aldrich) 30 minutes with end-over-end rotation. After removing excess metal ions, beads were washed 3× with 800 µL water, and resuspended in 1:1:1 acetonitrile:methanol:0.01% acetic acid. Desalted peptides (800 µg peptides/200 µL Fe-NTA beads; added at a concentration of 1 µg/µL in 80% MeCN/0.1% TFA) were added to beads after supernatant removal, and incubated for minutes at room temperature with end-over-end rotation. Beads were washed 3 times with 400 µL 80% MeCN/0.1% TFA, and phosphopeptides were eluted with 50 µL 1:20 ammonia/water with 3 mM EDTA. This eluate was removed, beads were washed further with 50 µL water, that was then combined with the ammonia elution. The pooled eluates were dried by vacuum centrifugation to ~5 µL, acidified with 5 µL 10% Tfa and 20 µL 0.1% TFA, and analyzed by LC/MS on a hybrid linear ion trap/Orbitrap mass spectrometer.

Example 18

Enrichment and Analysis of Labeled Phosphopeptides from K562 and SKI-606 Treated K562 Cells To dry tryptic peptides from K562 cells (800 µg, prepared as described above) was added 560 µL water, 240 µL 1 M HEPES pH 8.0, and trifluoroacetyl β alanine N-hydroxysulfosuccinimide ester (approximately 8 µmol in 40 µL 50% MeCN) and allowed to react for 1 hour at room temperature. In a separate solution, 800 µg dried tryptic peptides from SKI-606 treated K562 cells (prepared as described above, except that K562 cells were treated with SKI-606) were added to 560 µL water, 240 µL 1 M HEPES pH 8.0, and $^{13}$C-3, $^{15}$N-1 trifluoroacetyl β alanine N-hydroxysulfosuccinimide ester (approximately 8 µmol in 40 µL 50% MeCN) and allowed to react for 1 hour at room temp. After 1 hour, samples were combined and deprotection was achieved by adding 500 µL 1:5 ammonia, pH 11.5, and 100 µL 250 mM sodium carbonate pH 11.5, and incubating at 56° C. for 60 minutes. This solution was then acidified with Tfa, and peptides were desalted. Phosphopeptides were enriched using magnetic beads and analyzed by mass spectrometry as described in Example 17.

Example 19

Quantitative Phosphoproteomics Analysis of Phosphopeptides from Pervanadate or Unstimulated Jurkat Cells Jurkat cells were cultured, and proteins harvested, digested, and desalted as described above for K562 cells. Pervanadate treatment was performed by adding $H_2O_2$ activated sodium orthovanadate to cells (1 E7/mL) to a final concentration of 500 µm for 20 minutes at 37° C. To 400 µg dried tryptic peptides from pervanadate stimulated Jurkat cells was added to 280 µL water, 120 µL 1 M HEPES pH 8.0, and trifluoroacetyl β alanine N-hydroxysulfosuccinimide ester (approximately 4 µmol in 20 µL 50% MeCN) and allowed to react for 1 hour at room temp. In a separate reaction, 400 µg dried tryptic peptides from unstimulated Jurkat cells were added to 280 µL water, 120 µL 1 M HEPES pH 8.0, and $^{13}$C-3, $^{15}$N-1 trifluoroacetyl β alanine N-hydroxysulfosuccinimide ester (approximately 4 µmol in 20 µL 50% MeCN) and allowed to react for 1 hour at room temperature. After 1 hour, samples were combined and deprotection was achieved by adding 500 µL 1:5 ammonia, pH 11.5, and 100 µL 250 mM sodium carbonate pH 11.5, and incubating at 56° C. for 60 minutes. Peptides were desalted, and phosphopeptides enriched and analyzed as described in Example 17.

Example 20

MALDI-MS and MS/MS Analysis of Phosphorylated Peptides

Matrix (5 mg/mL HCCA in 70% acetonitrile, 0.1% TFA with 120 µg/mL diammonium citrate). was applied to eluted samples on a stainless steel target plate (384 well Opti-TOF, Applied Biosystems). Samples were analyzed using a 4800 MALDI-TOF/TOF mass spectrometer (Applied Biosystems, Framingham, Mass.) in reflectron mode averaging 1500 laser shots in a random, uniform pattern (30 sub-spectra, pass or fail, 50 shots/sub-spectrum) with a laser intensity of ~3700. MS/MS experiments were performed in reflectron mode averaging 5000 laser shots in a random uniform pattern (100 sub-spectra, pass or fail, 50 shots/sub-spectrum) with CID gas on and the precursor mass window set to relative with a value of 200 (FWHM).

Example 21

Synthesis of Trifluoroacetyl Beta Alanyl-β Alanine N-Hydroxysulfosuccinimide Ester 12 mg β Alanine (~0.14 mmol) was dissolved in 2 mL acetonitrile, 1 mL water, and 1 mL 1 M triethylammonium bicarbonate. Added to this was 50 mg trifluoroacetyl β-alanine N-hydroxysulfosuccinimide ester (~0.14 mmol). The mixture was allowed to react for 1 hour at room temperature. After reacting, the solution was acidified with TFA. Removal of solvent afforded a yellow oil, which was reconstituted in 10 mL 0.1% Tfa and purified by $C_{18}$ chromatography. After removing the solvent, the product was dissolved in 1.5 mL dichloromethane and 300 µL DMF. Added to this was a 2-fold excess of N-hydroxysulfosuccinimide, followed by a 2 fold excess of di-isopropyl carbodiimide. The reaction mixture was allowed to stir for 2 hours at room temperature. The DIC-urea was removed by filterration and dried to an oil, which was solublized in 1 mL 50% acetonitrile, aliquoted, and frozen immediately.

Example 22

Synthesis of Trifluoroacetyl Beta Alanyl-$^{13}$C-3, $^{15}$N-1 β Alanine N-Hydroxysulfosuccinimide Ester 12.8 mg $^{13}$C-3, $^{15}$N-1 β alanine (~0.14 mmol) was dissolved in 2 mL acetonitrile, 1 mL water, and 1 mL 1 M triethylammonium bicarbonate. Added to this was 50 mg trifluoroacetyl β-alanine N-hydroxysulfosuccinimide ester (~0.14 mmol). The mixture was allowed to react for 1 hour at room temperature. After reacting, the solution was acidified with TFA, and dried to a yellow oil, reconstituted in 10 mL 0.1% Tfa and purified by $C_{18}$ chromatography. Following removal of solvent, the product was dissolved in 1.5 mL dichloromethane and 300 µL DMF. Added to this was a 2-fold excess of N-hydroxysulfosuccinimide, followed by a 2 fold excess of di-isopropyl carbodiimide. The reaction mixture was allowed to stir for 2 hours at room temperature.

The DIC-urea byproduct was removed by filtration, the solvent was removed, and the resulting oil was solublized in 1 mL 50% acetonitrile, aliquotted, and frozen immediately.

Example 23

Synthesis of Trifluoroacetyl $^{13}$C-3, $^{15}$N-1 Beta Alaninyl-$^{13}$C-3, $^{15}$N-1 β Alanine N-Hydroxysulfosuccinimidyl Ester 12.8 mg $^{13}$C-3, $^{15}$N-1 β alanine (~0.14 mmol) was dissolved in 2 mL acetonitrile, 1 mL water, and 1 mL 1 M triethylammonium bicarbonate. Added to this was 50 mg trifluoroacetyl $^{13}$C-3, $^{15}$N-1 β alanine N-hydroxysulfosuccinimide ester (~0.14 mmol). The mixture was allowed to react for 1 hour at room temperature. After reacting, the solution was acidified with TFA, and dried to a yellow oil, reconstituted in 10 mL 0.1% Tfa and purified by $C_{18}$ chromatography. Following removal of solvent, the product was dissolved in 1.5 mL dichloromethane and 300 μL DMF. Added to this was a 2-fold excess of N-hydroxysulfosuccinimide, followed by a 2 fold excess of di-isopropyl carbodiimide. The reaction mixture was allowed to stir for 2 hours at room temperature. The DIC-urea byproduct was removed by filtration, the solvent was removed, and the resulting oil was solublized in 1 mL 50% acetonitrile, aliquotted, and frozen immediately.

Example 24

Individual Labeling of Peptides with Trifluoroacetyl Beta Alaninyl-β Alanine N-Hydroxysulfosuccinimide Ester, Trifluoroacetyl β Alanyl-$^{13}$C-3, $^{15}$N-1 β Alanine N-Hydroxysulfosuccinimide Ester, or Trifluoroacetyl $^{13}$C-3, $^{15}$N-1 Beta Alaninyl-$^{13}$C-3, $^{15}$N-1 β Alanine N-Hydroxysulfosuccinimide Ester

[Glu-1]-Fibrinopeptide B (1 nmol dissolved in 2 μL of water) was added to a solution of 70 μL ethanol and 30 μL of 500 mM HEPES pH 8.0. 10 μL Trifluoroacetyl beta alanine-β alanine N-hydroxysulfosuccinimide ester, trifluoroacetyl beta alanine-$^{13}$C-3, $^{15}$N-1 β alanine N-hydroxysulfosuccinimide ester or trifluoroacetyl $^{13}$C-3, $^{15}$N-1 beta alanine-$^{13}$C-3, $^{15}$N-1 β alanine N-hydroxysulfosuccinimide ester was added and allowed to react for 1 hour at room temperature. After labeling, reactions were either diluted with 0.1% formic acid, desalted using zip tips, and analyzed by MALDI MS, or were first deprotected. Deprotection was achieved by adding 1:5 ammonia/water, pH 11.5, and incubating at 50 C for 60 minutes. This solution was then acidified with Tfa, desalted using zip tips, and analyzed by MALDI-MS as described in example 20.

Example 25

Combined Labeling of a Standard Peptide with Trifluoroacetyl Beta Alanine-β Alanine N-Hydroxysulfosuccinimide Ester, Trifluoroacetyl Beta Alanine-$^{13}$C-3, $^{15}$N-1 β Alanine N-Hydroxysulfosuccinimide Ester, and Trifluoroacetyl $^{13}$C-3, $^{15}$N-1 Beta Alanine-$^{13}$C-3, $^{15}$N-1 β Alanine N-Hydroxysulfosuccinimide Ester In three separate reactions, [Glu-1]-Fibrinopeptide B (1 nmol dissolved in 2 μL of water) was added to a solution of 70 μL ethanol and 30 μL of 500 mM HEPES pH 8.0. To one reaction was added 10 μL trifluoroacetyl β alanine-β alanine N-hydroxysulfosuccinimide ester and allowed to react for 1 hour at room temperature. To the second reaction was added 10 μL trifluoroacetyl $^{13}$C-3, $^{15}$N-1 β alanine-β alanine N-hydroxysulfosuccinimide ester and allowed to react for 1 hour at room temp. To the third reaction was added 10 μL trifluoroacetyl $^{13}$C-3, $^{15}$N-1 β alanine-$^{13}$C-3, $^{15}$N-1 β alanine N-hydroxysulfosuccinimide ester and allowed to react for 1 hour at room temperature. After labeling, reactions were combined and either diluted with 0.1% formic acid, desalted using zip tips, and analyzed by MALDI MS (example 20), or were first deprotected. Deprotection was achieved by adding 1:5 ammonia/water, pH 11.5, and incubating at 50° C. for 60 minutes. This solution was then acidified with Tfa, desalted using zip tips, and analyzed by MALDI-MS (Example 20).

Example 26

Synthesis of (Trifluoroacetyl-Glycyl)$_2$-Lysine 2 mmol trifluoroacetyl glycine oil was dissolved in 2 mL DMF and 2 mL water. Added to this was 0.5 mmol lysine, followed by 2 mmol NMM, 2 mmol HOBt in 2 mL DMF, and 2 mmol PyBOP in 2 mL DMF, and allowed to react for 1 hour at room temperature. After one hour, the reaction was acidified with 1 mL 10% Tfa and 3 mL water. The reaction was then lyophilized overnight. Following lypholization, 10 mL 10% Tfa was added, the solution filtered, and the filtrate frozen, thawed, re-filtered, and purified by C18 chromatography. Removal of solvent afforded an orange oil.

Example 27

Synthesis of ($^{15}$N-1 Glycyl)$_2$-$^{15}$N-2 Lysine 2 mmol TFA $^{15}$N-1 Glycine oil was dissolved in 2 mL DMF and 2 mL water. Added to this was 0.5 mmol $^{15}$N-2 lysine, followed by 2 mmol NMM, 2 mmol HOBt in 2 mL DMF, and 2 mmol PyBOP in 2 mL DMF, and allowed to react for 1 hour at room temperature. After one hour, the reaction was acidified with 1 mL 10% Tfa and 3 mL water. The reaction was then lyophilized overnight. Following lypholization, 10 mL 10% Tfa was added, the solution filtered, and the filtrate frozen, thawed, re-filtered, and purified by C18 chromatography. Removal of solvent afforded an orange oil.

Example 28

Synthesis of (Trifluoroacetyl-$^{13}$C-2 Glycyl)$_2$-Lysine 2 mmol TFA $^{13}$C-2 Glycine oil was dissolved in 2 mL DMF and 2 mL water. Added to this was 0.5 mmol lysine, followed by 2 mmol NMM, 2 mmol HOBt in 2 mL DMF, and 2 mmol PyBOP in 2 mL DMF, and allowed to react for 1 hour at room temperature. After one hour, the reaction was acidified with 1 mL 10% Tfa and 3 mL water. The solution was then lyophilized overnight. Following lypholization, 10 mL 10% Tfa was added, the solution filtered, and the filtrate frozen, thawed, re-filtered, and purified by C18 chromatography. Removal of solvent afforded an orange oil.

Example 29

Synthesis of (Trifluoroacetyl-Glycyl)$_2$-Lysine N-Hydroxysulfosuccinimide Ester, (Trifluoroacetyl $^{15}$N-1 Glycyl)$_2$-$^{15}$N-2 Lysine N-Hydroxysulfosuccinimide Ester, and (Trifluoroacetyl-$^{13}$C-2 Glycyl)$_2$-Lysine N-Hydroxysulfosuccinimide Ester (Trifluoroacetyl-Glycyl)$_2$-Lysine oil, (Trifluoroacetyl $^{15}$N-1 Glycyl)$_2$-$^{15}$N-2 Lysine oil, or (Trifluoroacetyl-$^{13}$C-2

Glycyl)$_2$-Lysine oil was dissolved in 5 mL DMF. Added to this was 0.55 mmol N-hydroxysulfosuccinimide in 1 mL DMF, followed by 0.55 mmol DIC. Reaction proceeded for 2 hours at room temperature. After reaction complete, DIC-urea byproduct was removed by filtration. Reaction was then lyophilized to clear oil.

Example 30

Labeling of a Standard Peptide with (Trifluoro-acetyl $^{15}$N-1 Glycyl)$_2$-$^{15}$N-2 Lysine N-Hydroxysul-fosuccinimide Ester, and (Trifluoroacetyl-$^{13}$C-2 Glycyl)$_2$-Lysine N-Hydroxysulfosuccinimide Ester In two separate reactions, the phosphopeptide FLApT-GDGAR (either 1 nmol dissolved in 2 µL of water or 2 nmol dissolved in 4 µL water) was added to a solution of 70 µL ethanol and 30 µL of 500 mM HEPES pH 8.0. To the one nmol reaction was added 20 µL (Trifluoroacetyl $^{15}$N-1 Glycyl)$_2$-$^{15}$N-2 Lysine N-hydroxysulfosuccinimide ester and allowed to react for 1 hour at room temperature. To the 2 nmol reaction was added 20 µL (Trifluoroacetyl-$^{13}$C-2 Glycyl)$_2$-Lysine N-hydroxysulfosuccinimide ester and allowed to react for 1 hour at room temp. After labeling, reactions were combined deprotected. Deprotection was achieved by adding 1:5 ammonia/water, pH 11.5, and incubating at 50 C for 60 minutes. This solution was then acidified with Tfa, desalted using zip tips, and analyzed by MS using a hybrid linear ion trap/Orbitrap mass spectrometer operated in high resolution mode.

Example 31

Synthesis of Fmoc-$^{15}$N-1 Glycine and Fmoc $^{13}$C-1 Glycine

To a mixture of 1 mmol $^{15}$N-1 Glycine or $^{13}$C-1 Glycine, 3 mL acetone, 4 mL water, and 1 mmol NaHCO$_3$ was added 1 mmol of Fmoc-OSu. The mixture was stirred overnight. Solvent was removed by drying with air, and 5 mL ethyl acetate was added. After acidification with HCl, the organic layer was extracted 3× with water. Air drying of the organic layer afforded a white solid.

Example 32

Synthesis of Fmoc-$^{15}$N-1 Glycine N-Hydroxysuccinimide and Fmoc-$^{13}$C-1 Glycine N-Hydroxysuccinimide To a mixture of 1 mmol N-hydroxysuccinimide, 1 mmol Fmoc-$^{15}$N-1 Glycine or Fmoc $^{13}$C-1 Glycine, 4 mL DMF was added 1 mmol DIC. The mixture was stirred for 2 hours and lyophilized to an oil.

Example 33

Synthesis of Fmoc-($^{15}$N-1 Glycyl)-$^{15}$N-1 Glycine and Fmoc-($^{13}$C-1 Glycyl)-$^{13}$C-1 Glycine 1 mmol $^{15}$N-1-Glycine or $^{13}$C-1-Glycine was soliblized in 4 mL of 50% acetonitrile/500 mM triethylammonium bicarbonate pH 8.5 and then added to 1 mmol Fmoc-$^{15}$N-1 Glycine N-hydroxysuccinimide or Fmoc-$^{13}$C-1 Glycine N-hydroxysuccinimide oil. The mixture was incubated at room temperature for 1 hour, acidified with HCl and lyophilized to a solid, and purified by reversed-phase HPLC.

Example 34

Synthesis of Fmoc-($^{15}$N-1 Glycyl)$_2$ N-hydroxysulfosuccinimide and Fmoc-($^{13}$C-1 Glycyl)$_2$ N-hydroxysulfosuccinimide ~0.4 mmol of HPLC purified Fmoc-($^{15}$N-1 Glycyl)-$^{15}$N-1 Glycine or Fmoc-($^{13}$C-1 Glycyl)-$^{13}$C-1 Glycine was dissolved in 4 mL DMF with 0.4 mmol N-hydroxysulfosuccinimide and 0.4 mmol DIC. The mixture was stirred for 2 hr, filtered to remove the urea by-product, and lyophilized to an oil. The oil was dissolved in 1 mL of 50% acetonitrile and immediately aliquotted, frozen on dry ice, and then stored at −80 C.

Example 35

Differential Labeling of Tyrptic Digests of Standard Proteins with ($^{15}$N-1 Glycyl)-$^{15}$N-1 Glycine and ($^{13}$C-1 Glycyl)-$^{13}$C-1 Glycine Peptide mixture 1 was obtained by adding 1 uL 10 µmol/uL BSA tryptic digest, 0.5 uL beta galactosidase tryptic digest, 3 uL ovalbumin tryptic digest, and 0.5 uL beta-lactoglobulin tryptic digest to 5 uL 0.1% formic acid. Peptide mixture 2 was obtained by adding 1 uL 10 pmol/uL BSA tryptic digest, 1 uL beta galactosidase tryptic digest, 1 uL ovalbumin tryptic digest, and 2.5 uL beta-lactoglobulin tryptic digest to 4.5 uL 0.1% formic acid. Peptide solutions were then evaporated to dryness, and reconstituted with 30 uL 1 M HEPES, pH 8.0 and 70 uL ethanol. To peptide solution 1 was added 50 uL of Fmoc-$^{13}$C-1-Glycyl-$^{13}$C-1-Glycine-N-hydroxysulfosuccinimide, while to peptide solution 2 was added 50 uL of Fmoc-$^{15}$N-1-Glycyl-$^{15}$N-1-Glycine-N-hydroxysulfosuccinimide. The reactions were allowed to proceed for 3 hr, and were then combined and evaporated to dryness. Fmoc was removed by adding 100 uL of 20% piperidine in DMF for 30 minutes. The mixture was diluted with 0.1% TFA to a volume of 2 mL, and peptides were desalted by vacuum SPE (C18). The eluate was evaporated to dryness, reconstituted in 0.1% TFA, and analyzed by MS.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. An isotopically enriched amino acid based compound of formula II:

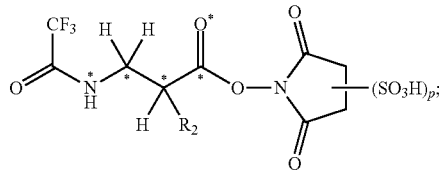

(II)

wherein,
R² is

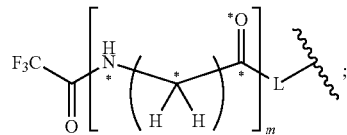

wherein L is NH—($C_1$-$C_6$ alkylene);
n is 1;
m is 1;
p is 1; and
each * represents $^{12}C$, $^{13}C$, $^{14}N$, $^{15}N$, $^{16}O$, wherein four * are $^{13}C$ or four * are $^{15}N$, and
wherein the compound has been enriched synthetically in $^{13}C$ or $^{15}N$.

2. A set of compounds, comprising two or more compounds of claim 1, wherein each of the two or more compounds has the same structure but differs in mass from each of the other compounds due to differing numbers of atoms of $^{12}C$, $^{13}C$, $^{14}N$, or $^{15}N$.

3. A set of compounds comprising two compounds represented by the structures:

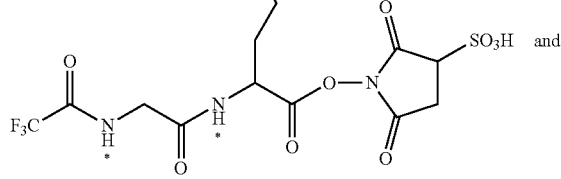

wherein each * represents $^{15}N$ or $^{13}C$, and
wherein the two compounds differ in mass by about 0.02524 Da.

4. An isotopically enriched amino acid based compound selected from the group consisting of:

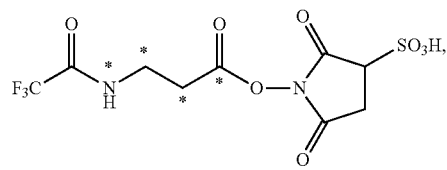

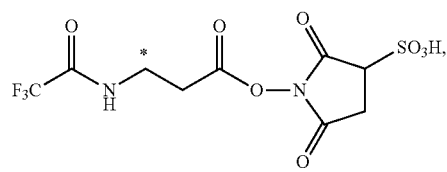

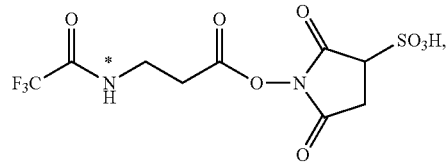

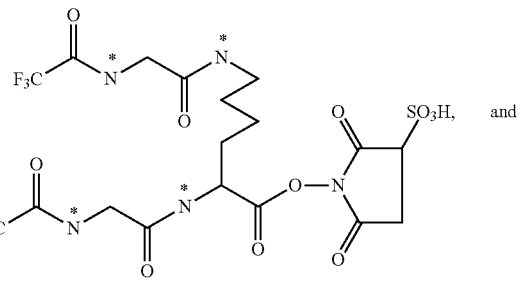

and

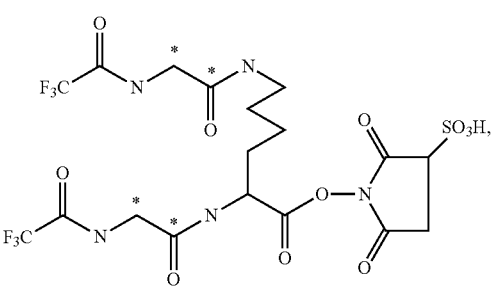

wherein the compound has been enriched synthetically in $^{13}C$ or $^{15}N$ at each *.

* * * * *